United States Patent
Shin et al.

(10) Patent No.: US 9,768,393 B2
(45) Date of Patent: Sep. 19, 2017

(54) CONDENSED-CYCLIC COMPOUND AND ORGANIC LIGHT-EMITTING DEVICE INCLUDING THE SAME

(71) Applicants: Samsung Electronics Co., Ltd., Suwon-si, Gyeonggi-do (KR); CHEIL INDUSTRIES INC., Gumi-si, Gyeongsangbuk-do (KR)

(72) Inventors: Chang-ju Shin, Uiwang-si (KR); Young-kwon Kim, Uiwang-si (KR); Hyung-sun Kim, Uiwang-si (KR); Moo-jin Park, Uiwang-si (KR); Joo-hee Seo, Uiwang-si (KR); Eun-sun Yu, Uiwang-si (KR); Byoung-ki Choi, Yongin-si (KR); Kyu-young Hwang, Ansan-si (KR)

(73) Assignees: SAMSUNG ELECTRONICS CO., LTD., Gyeonggi-Do (KR); CHEIL INDUSTRIES INC., Gyeongsangbuk-Do (KR)

(*) Notice: Subject to any disclaimer, the term of this patent is extended or adjusted under 35 U.S.C. 154(b) by 462 days.

(21) Appl. No.: 14/300,496

(22) Filed: Jun. 10, 2014

(65) Prior Publication Data

US 2015/0060791 A1  Mar. 5, 2015

(30) Foreign Application Priority Data

Sep. 4, 2013 (KR) .................. 10-2013-0106306

(51) Int. Cl.
  *H01L 51/00* (2006.01)
  *C07D 405/14* (2006.01)
  (Continued)

(52) U.S. Cl.
  CPC ........ *H01L 51/0067* (2013.01); *C07D 221/04* (2013.01); *C07D 401/04* (2013.01);
  (Continued)

(58) Field of Classification Search
  None
  See application file for complete search history.

(56) References Cited

U.S. PATENT DOCUMENTS 9,288,869 B2   3/2016  Han et al.
2011/0210318 A1†  9/2011  Bae

FOREIGN PATENT DOCUMENTS

KR  10-2011-0002156  †  1/2011
KR  1020110002156 A  1/2011
(Continued)

OTHER PUBLICATIONS

Machine English translation of Ahn et al. (KR 10-2012-0021203). Aug. 26, 2016.*

(Continued)

*Primary Examiner* — J. L. Yang
(74) *Attorney, Agent, or Firm* — Cantor Colburn LLP

(57) ABSTRACT

A condensed-cyclic compound of Formula 1:

Formula 1

(Continued)

wherein, in Formula 1, groups $X_1$, $X_{11}$ to $X_{14}$, $L_{21}$, $L_{22}$, $R_{21}$, and $R_{21}$, and variables a21, a22, b21, b22, c21, and c22 are described in the specification.

21 Claims, 5 Drawing Sheets

(51) Int. Cl.
| | | |
|---|---|---|
| *C07D 221/04* | (2006.01) | |
| *C07D 401/04* | (2006.01) | |
| *C07D 401/10* | (2006.01) | |
| *C07D 405/04* | (2006.01) | |
| *C07D 405/10* | (2006.01) | |
| *C07D 409/04* | (2006.01) | |
| *C07D 409/10* | (2006.01) | |
| *C07D 409/14* | (2006.01) | |
| *C07D 413/10* | (2006.01) | |
| *C07D 417/10* | (2006.01) | |
| *C07D 471/04* | (2006.01) | |
| *C09K 11/06* | (2006.01) | |

(52) U.S. Cl.
CPC ......... *C07D 401/10* (2013.01); *C07D 405/04* (2013.01); *C07D 405/10* (2013.01); *C07D 405/14* (2013.01); *C07D 409/04* (2013.01); *C07D 409/10* (2013.01); *C07D 409/14* (2013.01); *C07D 413/10* (2013.01); *C07D 417/10* (2013.01); *C07D 471/04* (2013.01); *C09K 11/06* (2013.01); *H01L 51/0072* (2013.01); *C09K 2211/1011* (2013.01); *C09K 2211/1014* (2013.01); *H01L 51/0081* (2013.01); *H01L 51/0085* (2013.01); *H01L 2251/308* (2013.01)

(56) References Cited

FOREIGN PATENT DOCUMENTS

| | | | |
|---|---|---|---|
| KR | 10-2011-0044587 | † | 4/2011 |
| KR | 1020110058250 A | | 6/2011 |
| KR | 1020120021203 A | | 3/2012 |
| KR | 10-2013-0051807 A | | 5/2013 |
| WO | 2010/114264 A2 | † | 10/2010 |

OTHER PUBLICATIONS

Machine English translation of Bae et al. (KR 10-2011-0002156). Aug. 26, 2016.*

* cited by examiner
† cited by third party

CONDENSED-CYCLIC COMPOUND AND ORGANIC LIGHT-EMITTING DEVICE INCLUDING THE SAME

CROSS-REFERENCE TO RELATED APPLICATIONS

This application claims priority to Korean Patent Application No. 10-2013-0106306, filed on Sep. 4, 2013, in the Korean Intellectual Property Office, and all the benefits accruing therefrom under 35 U.S.C. §119, the content of which is incorporated herein in its entirety by reference.

BACKGROUND

1. Field

One or more embodiments of relate to a condensed-cyclic compound and an organic light-emitting device including the same.

2. Description of the Related Art

Organic light emitting devices are self-emission devices that have wide viewing angles, a high contrast ratio, short response times, and excellent brightness, driving voltage, response speed characteristics, and produce full color images.

As an example, an organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, are recombined in the emission layer to produce excitons. These excitons change from an excited state to a ground state, thereby generating light.

While many organic light-emitting devices are presently known, there remains a need in a device wherein an organic layer has excellent electric characteristics and thermal stability.

SUMMARY

One or more embodiments relate to a novel condensed-cyclic compound and an organic light-emitting device including the same.

An aspect provides a condensed-cyclic compound represented by Formula 1:

Formula 1

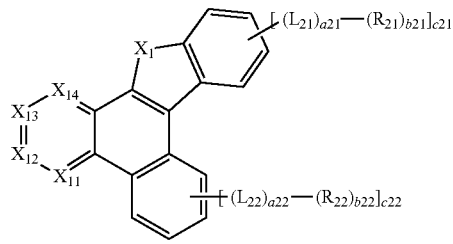

wherein in Formula 1, $X_1$ is selected from $N-[(L_1)_{a1}-(R_1)_{b1}]$, S, O, S(=O), S(=O)$_2$, C(R$_2$)(R$_3$), and Si(R$_2$)(R$_3$), provided that when $X_1$ is C(R$_2$)(R$_3$) or Si(R$_2$)(R$_3$), R$_2$ and R$_3$ do not form a ring;

$X_{11}$ is N or C-$[(L_{11})_{a11}-(R_{11})_{b11}]$,
$X_{12}$ is N or C-$[(L_{12})_{a12}-(R_{12})_{b12}]$,
$X_{13}$ is N or C-$[(L_{13})_{a13}-(R_{13})_{b13}]$, and
$X_{14}$ is N or C-$[(L_{14})_{a14}-(R_{14})_{b14}]$;

$L_1$, $L_{11}$, $L_{12}$, $L_{13}$, $L_{14}$, $L_{21}$, and $L_{22}$ are each independently selected from a substituted or unsubstituted $C_3$-$C_{10}$ cycloalkylene group, a substituted or unsubstituted $C_3$-$C_{10}$ heterocycloalkylene group, a substituted or unsubstituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic hetero-condensed polycyclic group;

a1, a11, a12, a13, a14, a21, and a22 are each independently selected from an integer of 0 to 5;

$R_1$, $R_2$, $R_3$, $R_{11}$, $R_{12}$, $R_{13}$, $R_{14}$, $R_{21}$, and $R_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ hetero aryl group, a substituted or unsubstituted monovalent non-aromatic condensed polycyclic group, a substituted or unsubstituted monovalent non-aromatic hetero-condensed polycyclic group, —N(Q$_1$)(Q$_2$), —Si(Q$_3$)(Q$_4$)(Q$_5$), and —B(Q$_6$)(Q$_7$); b1, b11, b12, b13, b14, b21, and b22 are each independently selected from an integer of 1 to 5;

c21 and c22 are each independently 1, 2, 3, or 4, provided that when c21 is two or more, groups *-$(L_{21})_{a21}$-$R_{21}$ are identical or different, and when c22 is two or more, groups *-$(L_{22})_{a22}$-$R_{22}$ are identical or different; and at least one of the substituted $C_3$-$C_{10}$ cycloalkylene group, the substituted $C_3$-$C_{10}$ heterocycloalkylene group, the substituted $C_3$-$C_{10}$ cycloalkenylene group, the substituted $C_3$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic hetero-condensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_3$-$C_{10}$ heterocycloalkyl group, the substituted $C_3$-$C_{10}$ cycloalkenyl group, the substituted $C_3$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ hetero aryl group, the substituted monovalent non-aromatic condensed polycyclic group, and the substituted monovalent non-aromatic hetero-condensed polycyclic group may be substituted with a group selected from selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a monovalent non-aromatic condensed polycyclic group, a monovalent non-aromatic hetero-condensed polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a monovalent non-aromatic condensed polycyclic group, and a monovalent non-aromatic hetero-condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a monovalent non-aromatic condensed polycyclic group, and a monovalent non-aromatic hetero-condensed polycyclic group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a C6-C60 aryloxy group, a C6-C60 arylthio group, a $C_2$-$C_{60}$ hetero aryl group, a monovalent non-aromatic condensed polycyclic group, a monovalent non-aromatic hetero-condensed polycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$); and $Q_1$ to $Q_7$, $Q_{11}$ to $C_{17}$, $C_{21}$ to $Q_{27}$, and $C_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a C3-C10 heterocycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a mon-ovalent non-aromatic condensed polycyclic group, and a monovalent non-aromatic hetero-condensed polycyclic group.

The condensed-cyclic compound may be represented by Formula 1A or 1B below:

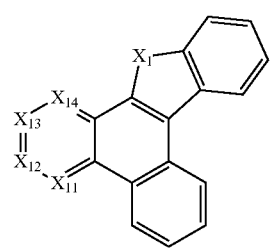

Formula 1A

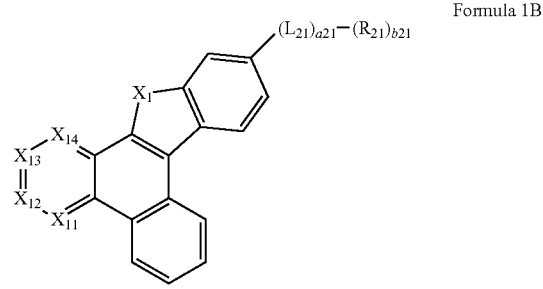

Formula 1B

According to another embodiment, the condensed-cyclic compound may be represented by Formula 1A(1) or 1B(1) below.

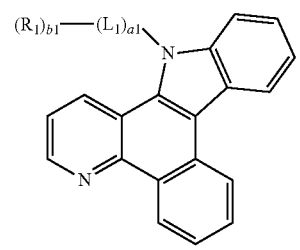

Formula 1A(1)

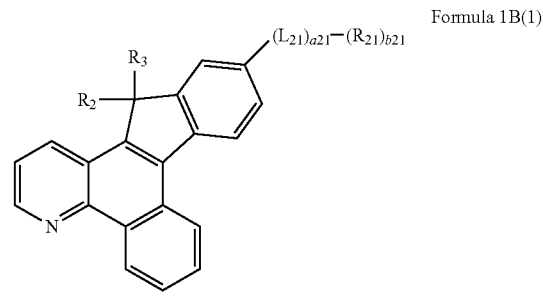

Formula 1B(1)

Another aspect provides an organic light-emitting device including:

a first electrode;

a second electrode facing the first electrode; and an organic layer that is disposed between the first and second electrodes, wherein the organic layer includes an emission layer, and has at least one of the condensed-cyclic compound represented by Formula 1.

The condensed-cyclic compound may be included in the emission layer as a host, and the emission layer may further include a dopant. Herein, the emission layer may be a green emission layer emitting green light, and the dopant may be a phosphorescent dopant that emits light according to a phosphorescent mechanism.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
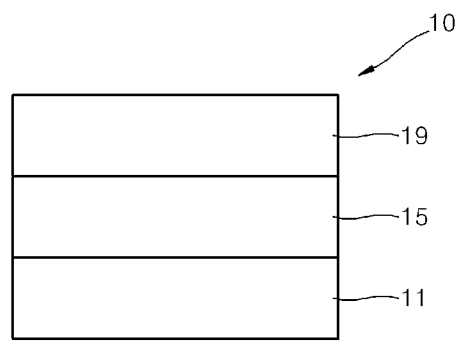
FIG. 1 is a schematic view of an organic light-emitting device according to an embodiment.
Figure 2A:
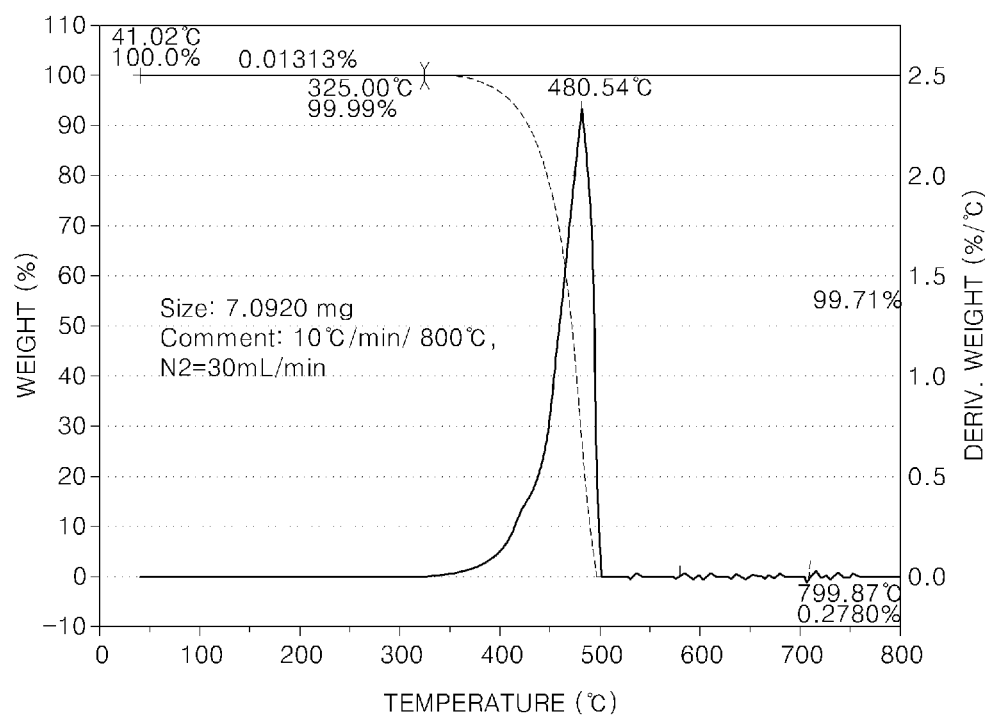
FIG. 2A is a graph of weight (percent, %) and derivative of weight (percent per degree Centigrade, ° C.) versus temperature (degrees Centigrade, ° C.) showing thermo gravimetric analysis (TGA) data of Compound 2.
Figure 2B:
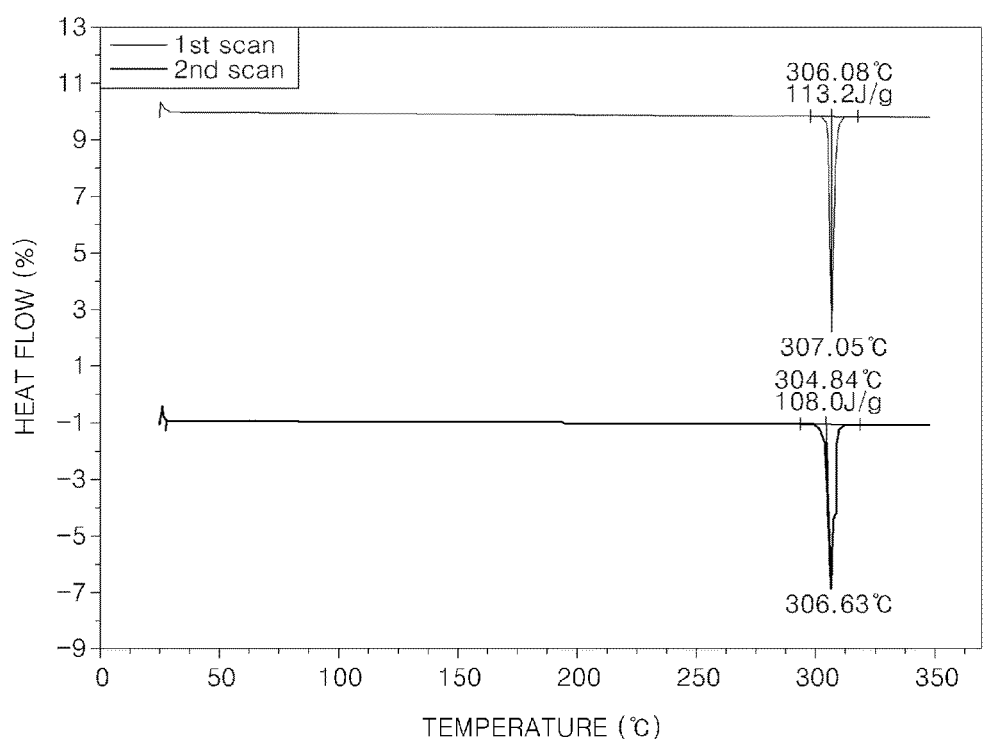
FIG. 2B is a graph of heat flow (percent, %) versus temperature (degrees Centigrade, ° C.) showing differential scanning calorimetry (DSC) data of Compound 2.
Figure 3A:
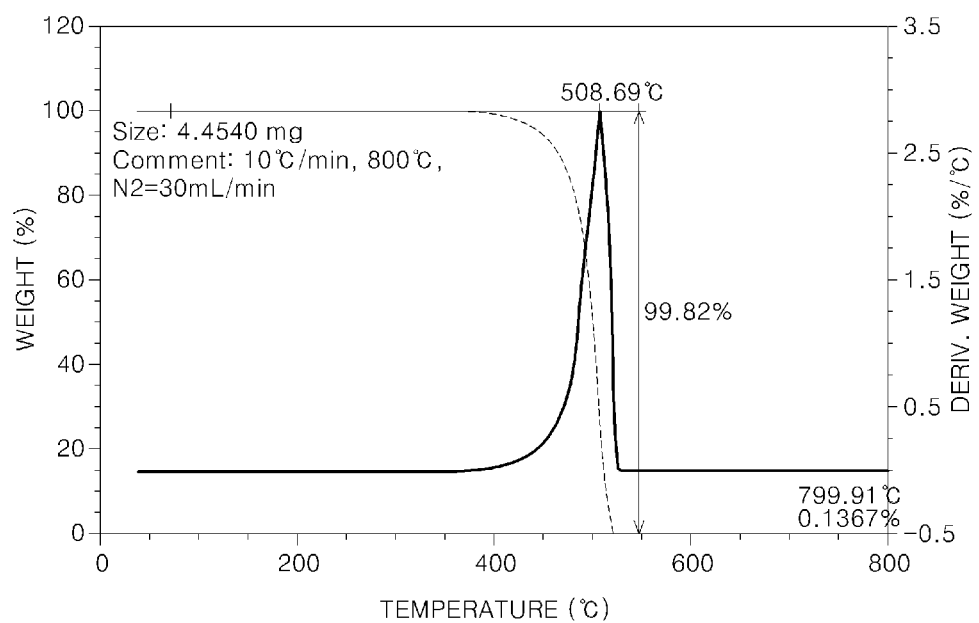
FIG. 3A is a graph of weight (percent, %) and derivative of weight (percent per degree Centigrade, ° C.) versus temperature (degrees Centigrade, ° C.) showing TGA data of Compound 4.
Figure 3B:
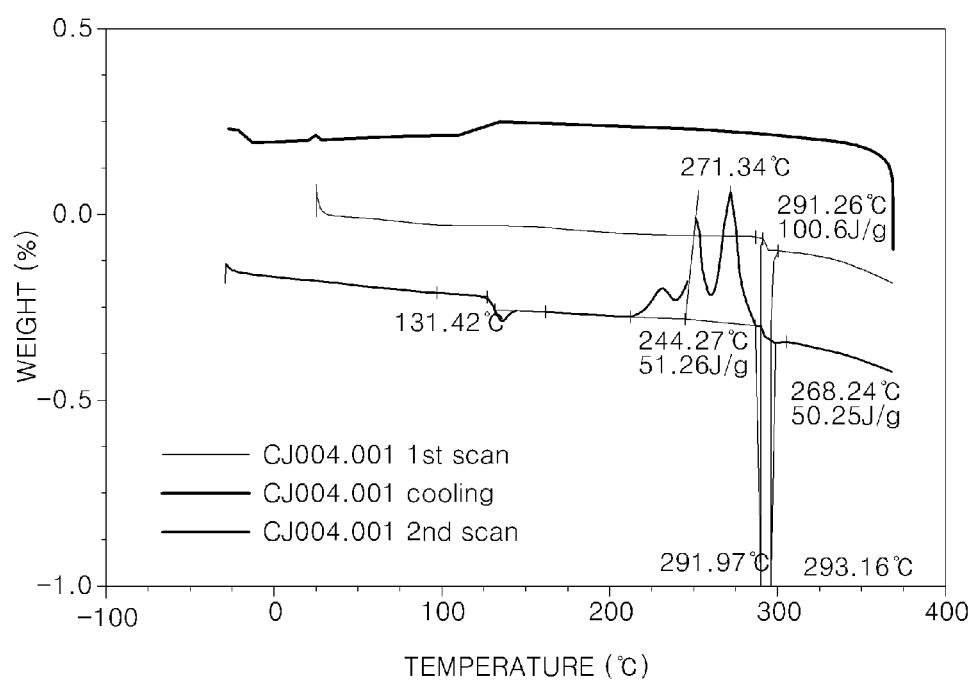
FIG. 3B shows DSC data of Compound 4.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

A condensed-cyclic compound according to an embodiment is represented by Formula 1 below:

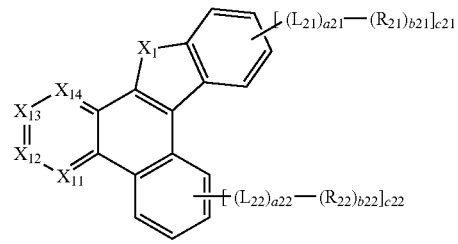

Formula 1

$X_1$ in Formula 1 is selected from N-$[(L_1)_{a1}$-$(R_1)_{b1}]$, S, O, S(=O), S(=O)$_2$, C($R_2$)($R_3$), and Si($R_2$)($R_3$), provided that when $X_1$ is C($R_2$)($R_3$) or Si($R_2$)($R_3$), $R_2$ and $R_3$ do not form a ring.

According to an embodiment, $X_1$ in Formula 1 may be N-$[(L_1)_{a1}$-$(R_1)_{b1}]$. $L_1$, a1, $R_1$, and b1 may be understood by referring to the description provided herein.

According to another embodiment, $X_1$ in Formula 1 may be C($R_2$)($R_3$), and $R_2$ and $R_3$ are each independently selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group; and a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, but are not limited thereto.

According to another embodiment, $X_1$ in Formula 1 may be S or O.

In Formula 1, $X_{11}$ is N or $C-[(L_{11})_{a11}-(R_{11})_{b11}]$, $X_{12}$ is N or $C-[(L_{12})_{a12}-(R_{12})_{b12}]$, $X_{13}$ is N or $C-[(L_{13})_{a13}-(R_{13})_{b13}]$, and $X_{14}$ is N or $C-[(L_{14})_{a14}-(R_{14})_{b14}]$.

Herein, $L_{11}$ to $L_{14}$, a11 to a14, $R_{11}$ to $R_{14}$, and b11 to b14 may be understood by referring to the description provided therein.

According to an embodiment, in Formula 1, $X_{11}$ may be N, $X_{12}$ may be $C-[(L_{12})_{a12}-(R_{12})_{b12}]$, $X_{13}$ may be $C-[(L_{13})_{a13}-(R_{13})_{b13}]$, and $X_{14}$ may be $C-[(L_{14})_{a14}-(R_{14})_{b14}]$, but they are not limited thereto.

According to another embodiment, in Formula 1, $X_{11}$ may be $C-[(L_{11})_{a11}-(R_{11})_{b11}]$, $X_{12}$ may be N, $X_{13}$ may be $C-[(L_{13})_{a13}-(R_{13})_{b13}]$, and $X_{14}$ may be $C-[(L_{14})_{a14}-(R_{14})_{b14}]$, but they are not limited thereto.

According to another embodiment, in Formula 1, $X_{11}$ may be $C-[(L_{11})_{a11}-(R_{11})_{b11}]$, $X_{12}$ may be $C-[(L_{12})_{a12}-(R_{12})_{b12}]$, $X_{13}$ may be N, and $X_{14}$ may be $C-[(L_{14})_{a14}-(R_{14})_{b14}]$, but they are not limited thereto.

According to another embodiment, in Formula 1, $X_{11}$ may be $C-[(L_{11})_{a11}-(R_{11})_{b11}]$, $X_{12}$ may be $C-[(L_{12})_{a12}-(R_{12})_{b12}]$, $X_{13}$ may be $C-[(L_{13})_{a13}-(R_{13})_{b13}]$, and $X_{14}$ may be N, but they are not limited thereto.

According to another embodiment, in Formula 1, $X_{11}$ may be N, $X_{12}$ may be $C-[(L_{12})_{a12}-(R_{12})_{b12}]$, $X_{13}$ may be N, and $X_{14}$ may be $C-[(L_{14})_{a14}-(R_{14})_{b14}]$, but they are not limited thereto.

According to another embodiment, in Formula 1, $X_{11}$ may be N, $X_{12}$ may be $C-[(L_{12})_{a12}-(R_{12})_{b12}]$, $X_{13}$ may be $C-[(L_{13})_{a13}-(R_{13})_{b13}]$, and $X_{14}$ may be N, but they are not limited thereto.

According to an embodiment, in Formula 1, $L_1$, $L_{11}$, $L_{12}$, $L_{13}$, $L_{14}$, $L_{21}$, and $L_{22}$ may be each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, a oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, a oxadiazolylene group, a triazinylene group, a dibenzofuranylene group, a dibenzothiophenylene group, a benzocarbazolylene group, a dibenzocarbazolylene group, and an imidazopyridinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, a oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, a oxadiazolylene group, a triazinylene group, a dibenzofuranylene group, a dibenzothiophenylene group, a benzocarbazolylene group, a dibenzocarbazolylene group, and an imidazopyridinylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group.

According to another embodiment, in Formula 1, $L_1$, $L_{11}$, $L_{12}$, $L_{13}$, $L_{14}$, $L_{21}$, and $L_{22}$ may be each independently selected from Formulae 2-1 to 2-33.

Formula 2-1

Formula 2-2

Formula 2-3

Formula 2-4

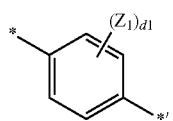

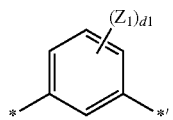

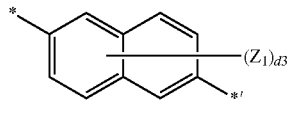

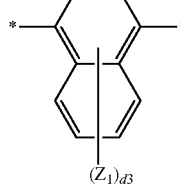

Formula 2-5

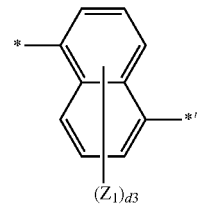

Formula 2-6

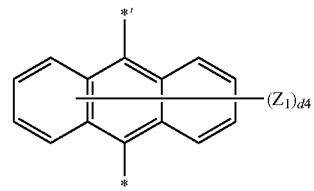

Formula 2-7

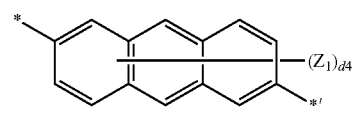

Formula 2-8

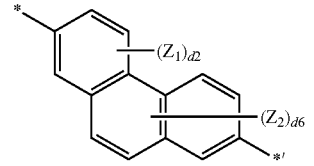

Formula 2-9

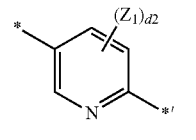

Formula 2-10

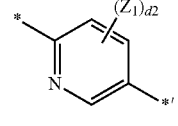

Formula 2-11

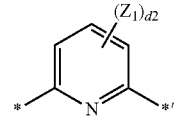

Formula 2-12

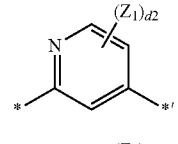

Formula 2-13

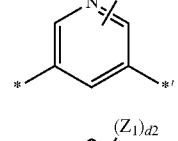

Formula 2-14

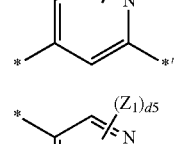

Formula 2-15

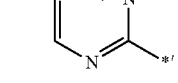

-continued

Formula 2-16
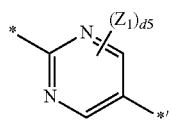

Formula 2-17
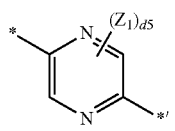

Formula 2-18
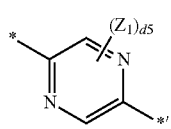

Formula 2-19
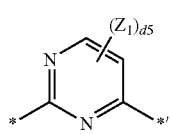

Formula 2-20
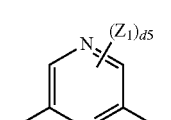

Formula 2-21
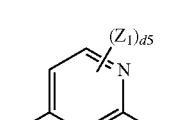

Formula 2-22
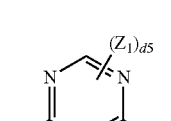

Formula 2-23
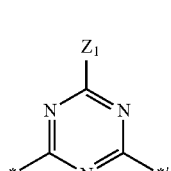

Formula 2-24
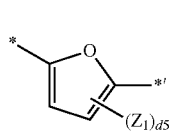

Formula 2-25
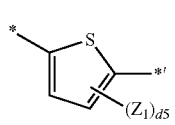

Formula 2-26
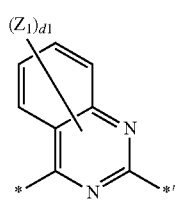

Formula 2-27
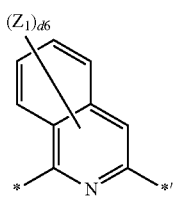

Formula 2-28
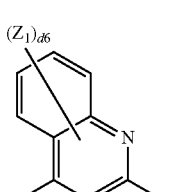

Formula 2-29
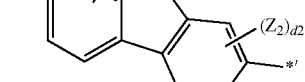

Formula 2-30
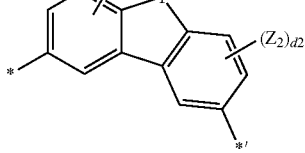

Formula 2-31
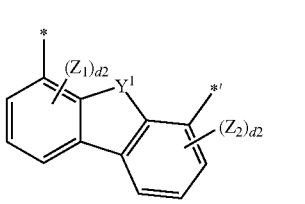

Formula 2-32
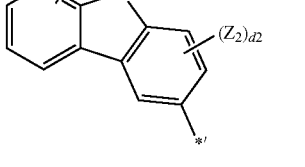

Formula 2-33
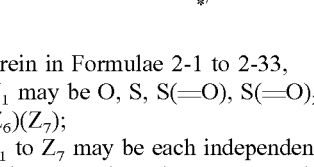

wherein in Formulae 2-1 to 2-33, $Y_1$ may be O, S, S(=O), S(=O)$_2$, C($Z_3$)($Z_4$), N($Z_5$), or Si($Z_6$)($Z_7$);

$Z_1$ to $Z_7$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a monovalent non-aromatic condensed polycyclic group, a monovalent non-aromatic hetero-condensed polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a monovalent non-aromatic condensed polycyclic group, and a monovalent non-aromatic hetero-condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a monovalent non-aromatic condensed polycyclic group, and a monovalent non-aromatic hetero-condensed polycyclic group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a C6-C60 aryloxy group, a C6-C60 arylthio group, a $C_2$-$C_{60}$ hetero aryl group, a monovalent non-aromatic condensed polycyclic group, a monovalent non-aromatic hetero-condensed polycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

d1 is an integer of 1 to 4;
d2 is an integer of 1 to 3;
d3 is an integer of 1 to 6;
d4 is an integer of 1 to 8;
d5 is 1 or 2;
d6 is an integer of 1 to 5; and
* and *' may each be a binding site to a neighboring atom.

$Q_{11}$ to $C_{17}$, $C_{21}$ to $Q_{27}$, and $C_{31}$ to $Q_{37}$ may be understood by referring to the description provided herein.

For example, in Formulae 2-1 to 2-33,
* indicates a binding site to a core of Formula 1 or a binding site to each of neighboring $L_1$, $L_{11}$, $L_{12}$, $L_{13}$, $L_{14}$, $L_{21}$, and $L_{22}$, and

*' in Formulae 2-1 to 2-33 indicates a binding site to each of neighboring $L_1$, $L_{11}$, $L_{12}$, $L_{13}$, $L_{14}$, $L_{21}$, and $L_{22}$ or each of $R_1$, $R_{11}$, $R_{12}$, $R_{13}$, $R_{14}$, $R_{21}$, and $R_{22}$.

For example, $Z_1$ to $Z_7$ in Formulae 2-1 to 2-33 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and —Si($Q_{33}$)($Q_{34}$)($Q_{35}$); and for example, $Q_{33}$ to $Q_{35}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, but are not limited thereto.

According to another embodiment, in Formula 1, $L_1$, $L_{11}$, $L_{12}$, $L_{13}$, $L_{14}$, $L_{21}$, and $L_{22}$ may be each independently selected from Formulae 3-1 to 3-38, but are not limited thereto.

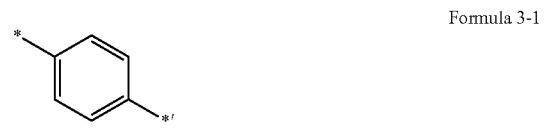

Formula 3-1

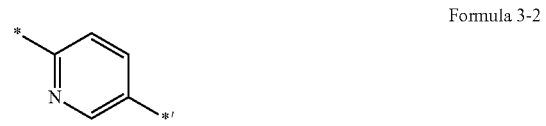

Formula 3-2

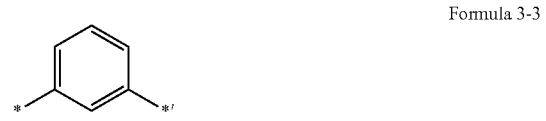

Formula 3-3

Formula 3-4

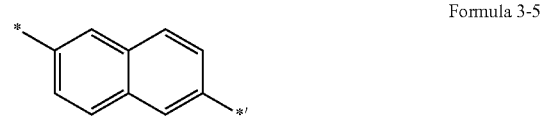

Formula 3-5

Formula 3-6

Formula 3-7

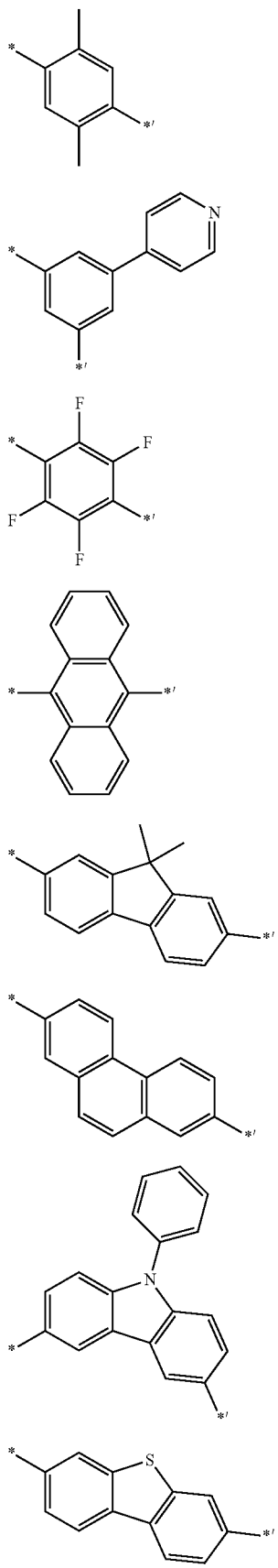
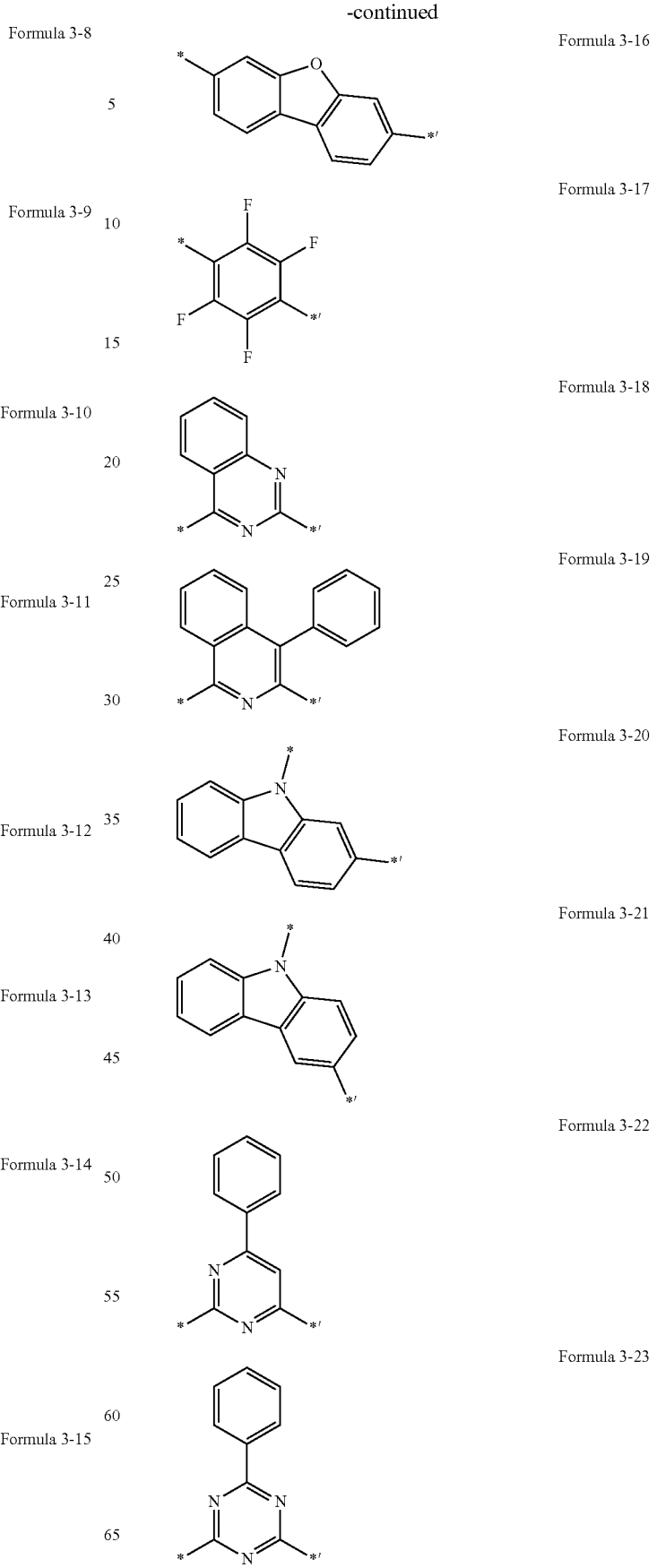

Formula 3-24
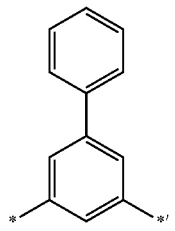
Formula 3-25
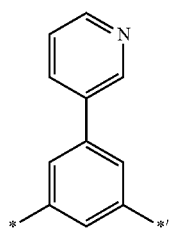
Formula 3-26
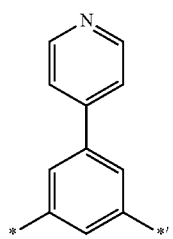
Formula 3-27
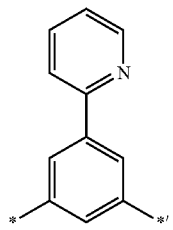
Formula 3-28
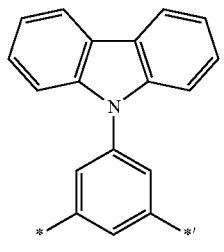
Formula 3-29
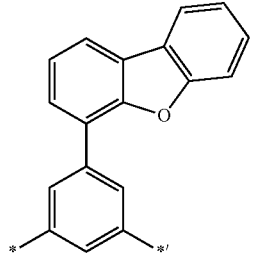
Formula 3-30
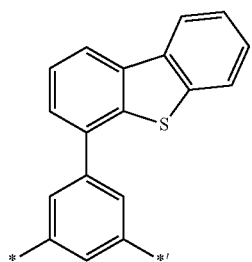
Formula 3-31
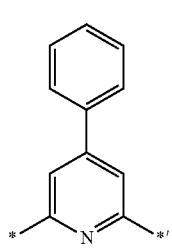
Formula 3-32
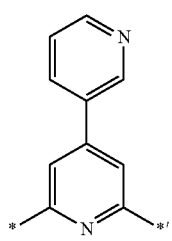
Formula 3-33
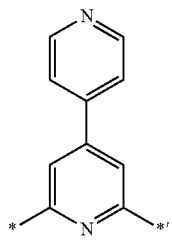
Formula 3-34
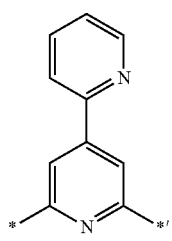
Formula 3-35
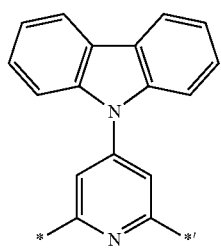

Formula 3-36

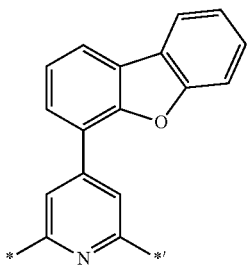

Formula 3-37

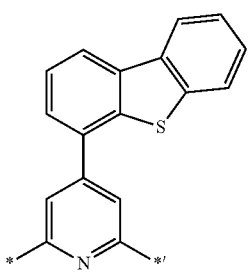

Formula 3-38

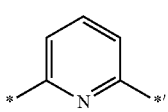

a1 in Formula 1 indicates the number of groups $L_1$, and may be 0, 1, 2, 3, 4, or 5, for example, 0, 1, or 2, or for example, 0 or 1. When a1 is 0, $R_1$ may directly bind to N. When a1 is 2 or more, a plurality of groups $L_1$ may be identical or different.

a11 in Formula 1 indicates the number of groups $L_{11}$, and may be 0, 1, 2, 3, 4, or 5, for example, 0, 1, or 2, or for example, 0 or 1. When a11 is 0, $R_{11}$ may directly bind to a carbon of the core of Formula 1. When a11 is 2 or more, a plurality of groups $L_{11}$ may be identical or different.

a12 in Formula 1 indicates the number of groups $L_{12}$, and may be 0, 1, 2, 3, 4, or 5, for example, 0, 1, or 2, or for example, 0 or 1. When a12 is 0, $R_{12}$ may directly bind to a carbon of the core of Formula 1. When a12 is 2 or more, a plurality of groups $L_{12}$ may be identical or different.

a13 in Formula 1 indicates the number of groups $L_{13}$, and may be 0, 1, 2, 3, 4, or 5, for example, 0, 1, or 2, or for example, 0 or 1. When a13 is 0, $R_{13}$ may directly bind to a carbon of the core of Formula 1. When a13 is 2 or more, a plurality of groups $L_{13}$ may be identical or different.

a14 in Formula 1 indicates the number of groups $L_{14}$, and may be 0, 1, 2, 3, 4, or 5, for example, 0, 1, or 2, or for example, 0 or 1. When a14 is 0, $R_{14}$ may directly bind to a carbon of the core of Formula 1. When a14 is 2 or more, a plurality of groups $L_{14}$ may be identical or different.

a21 in Formula 1 indicates the number of groups $L_{21}$, and may be 0, 1, 2, 3, 4, or 5, for example, 0, 1, or 2, or for example, 0 or 1. When a21 is 0, $R_{21}$ may directly bind to a carbon of the core of Formula 1. When a21 is 2 or more, a plurality of groups $L_{21}$ may be identical or different.

a22 in Formula 1 indicates the number of groups $L_{22}$, and may be 0, 1, 2, 3, 4, or 5, for example, 0, 1, or 2, or for example, 0 or 1. When a22 is 0, $R_{22}$ may directly bind to a carbon of the core of Formula 1. When a22 is 2 or more, a plurality of groups $L_{22}$ may be identical or different.

According to an embodiment, $R_1$ may be selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, an imidazopyridinyl group, each substituted with at least one groups selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_{33}$)($Q_{34}$)($Q_{35}$), a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, an benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group; wherein $Q_{33}$ to $C_{35}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, but are not limited thereto.

$R_2$, $R_3$, $R_{11}$, $R_{12}$, $R_{13}$, $R_{14}$, $R_{21}$, and $R_{22}$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkenyl group, and a $C_1$-$C_{20}$ alkoxy group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —$Si(Q_{33})(Q_{34})(Q_{35})$, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group; and —$Si(Q_3)(Q_4)(Q_5)$; wherein $Q_{33}$ to $Q_{35}$ and $Q_3$ to $Q_5$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, but are not limited thereto.

According to another embodiment, regarding Formula 1, $R_1$ may be selected from Formulae 4-1 to 4-31 below; $R_2$, $R_3$, $R_{11}$, $R_{12}$, $R_{13}$, $R_{14}$, $R_{21}$, and $R_{22}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkenyl group, and a $C_1$-$C_{20}$ alkoxy group; Formulae 4-1 to 4-31; and —Si($Q_3$)($Q_4$)($Q_5$); wherein $Q_3$ to $Q_5$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group:

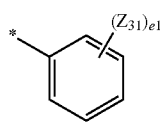

Formula 1-1

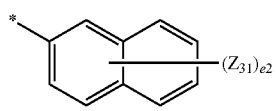

Formula 4-2

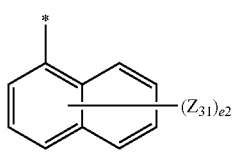

Formula 4-3

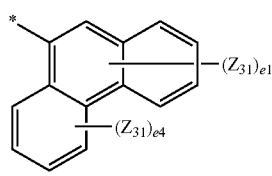

formula 4-4

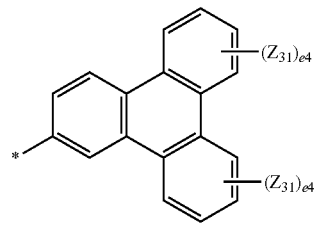

Formula 4-5

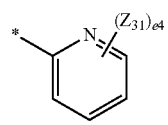

Formula 4-6

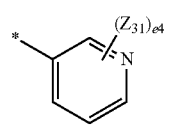

Formula 4-7

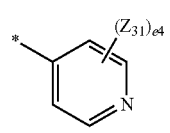

Formula 4-8

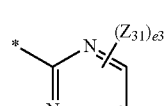

Formula 4-9

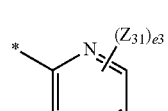

Formula 4-10

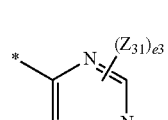

Formula 4-11

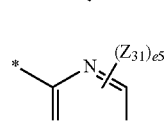

Formula 4-13

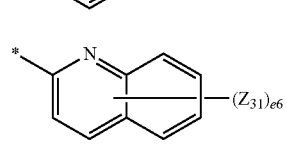

Formula 4-14

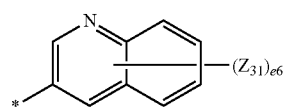

Formula 4-15

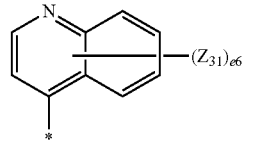

Formula 4-16

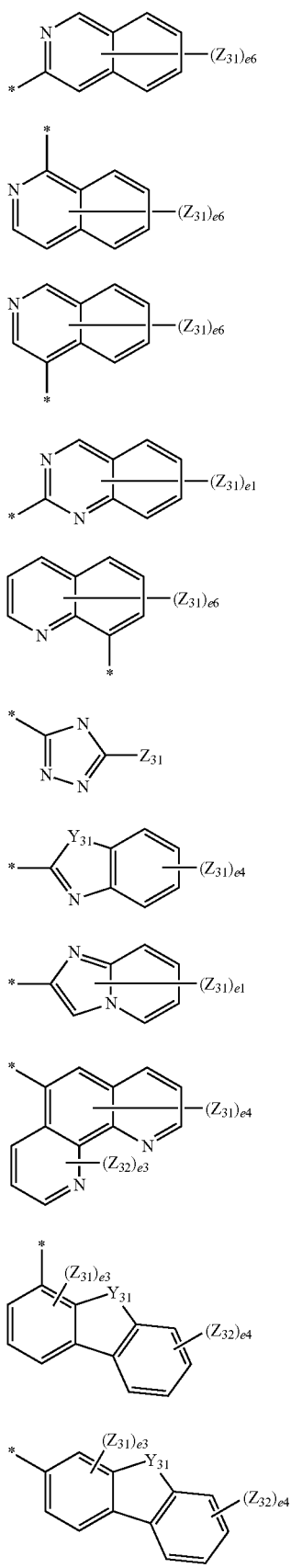

Formula 4-17
Formula 4-18
Formula 4-19
Formula 4-20
Formula 4-21
Formula 4-22
Formula 4-23
Formula 4-24
Formula 4-25
Formula 4-26
Formula 4-27

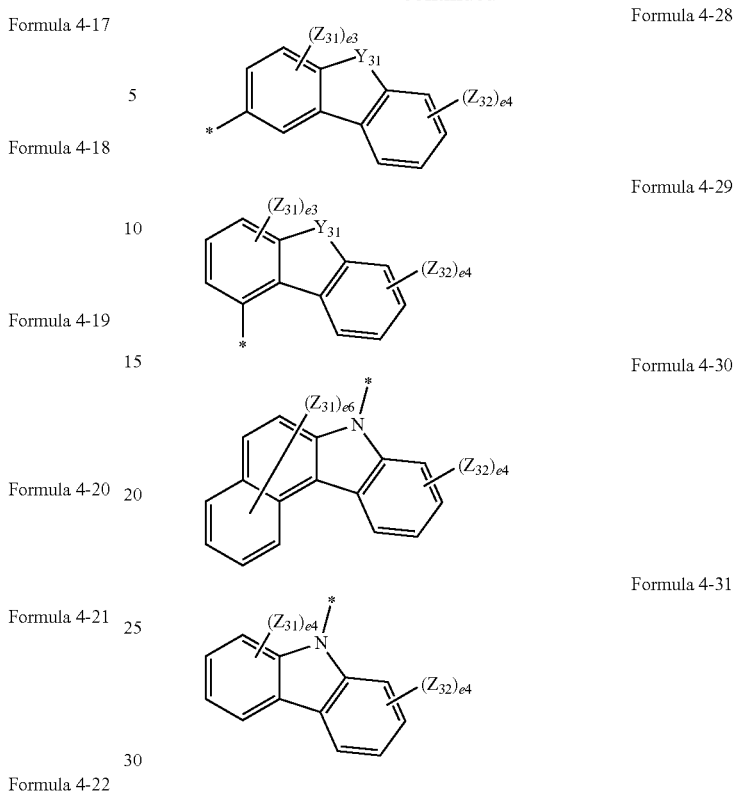

Formula 4-28
Formula 4-29
Formula 4-30
Formula 4-31 wherein in Formulae 4-1 to 4-31, $Y_{31}$ may be O, S, $C(Z_{33})(Z_{34})$, $N(Z_{35})$, or $Si(Z_{36})(Z_{37})$;

$Z_{31}$ to $Z_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a C3-C10 cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a monovalent non-aromatic condensed polycyclic group, a monovalent non-aromatic hetero-condensed polycyclic group, —$N(Q_{31})(Q_{32})$, —$Si(Q_{33})(Q_{34})(Q_{35})$, and —$B(Q_{36})(Q_{37})$;

e1 may be an integer of 1 to 5;
e2 may be an integer of 1 to 7;
e3 may be an integer of 1 to 3;
e4 may be an integer of 1 to 4;
e5 may be 1 or 2;
e6 may be an integer of 1 to 6; and
* indicates a binding site to a neighboring atom.

$Q_{31}$ to $Q_{37}$ may be understood by referring to the description provided herein.

For example, $Z_{31}$ to $Z_{37}$ in Formulae 4-1 to 4-31 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and —Si(Q$_{33}$)(Q$_{34}$)(Q$_{35}$); and Q$_{33}$ to Q$_{35}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, but are not limited thereto.

For example, e1, e2, e3, e4, e5, and e6 in Formulae 4-1 to 4-31 may be each independently 1 or 2.

According to another embodiment, regarding Formula 1, $R_1$ may be selected from Formulae 5-1 to 5-80;

$R_2$, $R_3$, $R_{11}$, $R_{12}$, $R_{13}$, $R_{14}$, $R_{21}$, and $R_{22}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group; a $C_1$-$C_{20}$ alkyl and a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group; Formula 5-1 to 5-80 below; and —Si(Q$_3$)(Q$_4$)(Q$_5$); and Q$_3$ to Q$_5$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group:

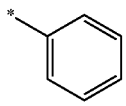

Formula 5-1

-continued

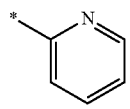

Formula 5-2

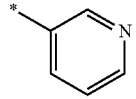

Formula 5-3

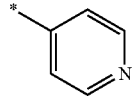

Formula 5-4

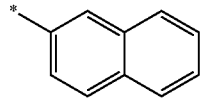

Formula 5-5

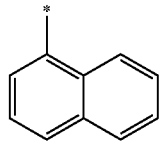

Formula 5-6

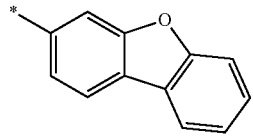

Formula 5-7

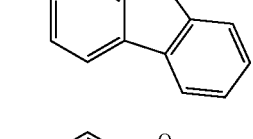

Formula 5-8

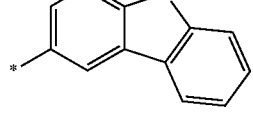

Formula 5-9

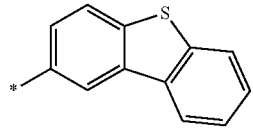

Formula 5-10

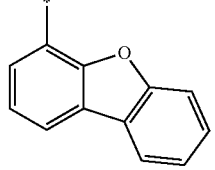

Formula 5-11

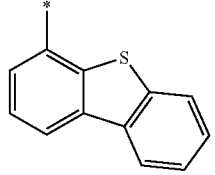

Formula 5-12

-continued
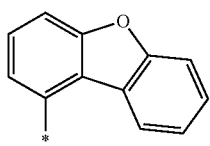
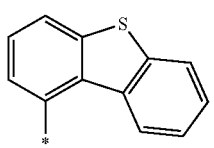
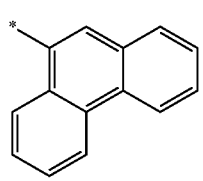
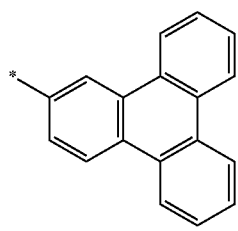
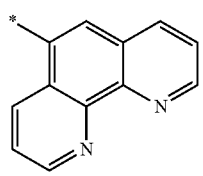
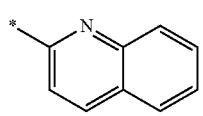
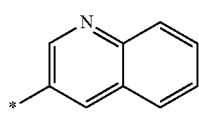
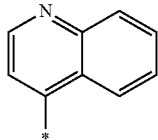
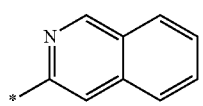
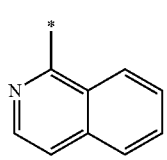
-continued
Formula 5-13
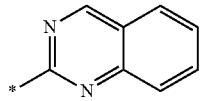
Formula 5-14
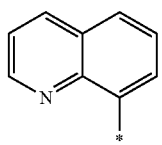
Formula 5-15
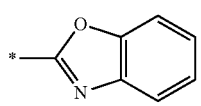
Formula 5-16
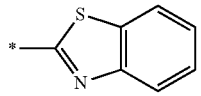
Formula 5-17
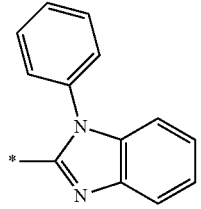
Formula 5-18
Formula 5-19
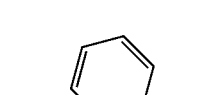
Formula 5-20
Formula 5-21
Formula 5-22
Formula 5-23
Formula 5-24
Formula 5-25
Formula 5-26
Formula 5-27
Formula 5-28
Formula 5-29
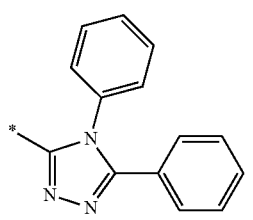
Formula 5-30
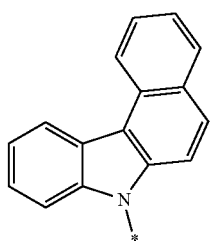
Formula 5-31
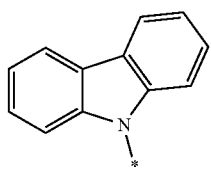

Formula 5-32
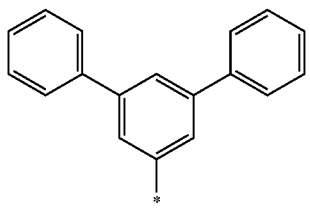
Formula 5-33
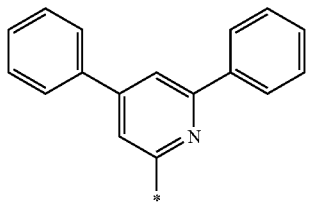
Formula 5-34
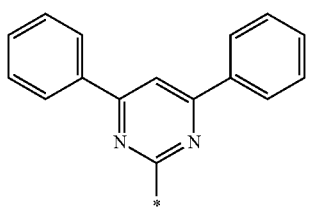
Formula 5-35
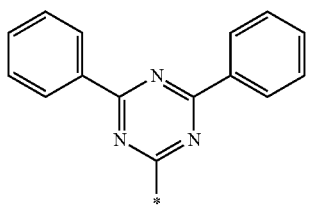
Formula 5-36
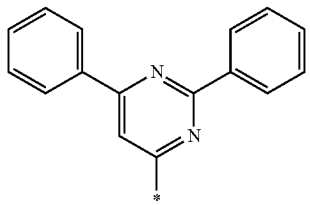
Formula 5-37
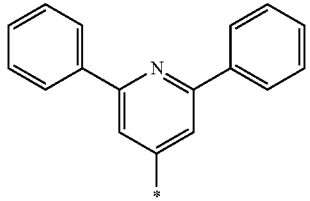
Formula 5-38
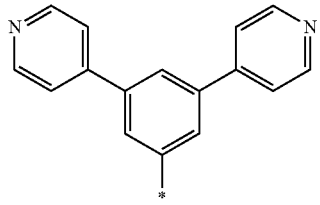
Formula 5-39
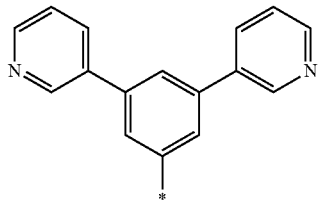
Formula 5-40
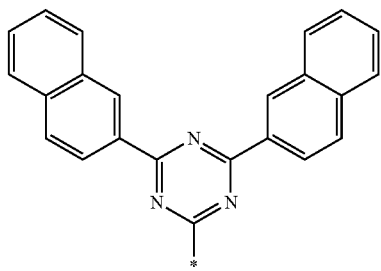
Formula 5-41
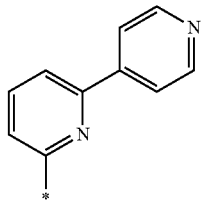
Formula 5-42
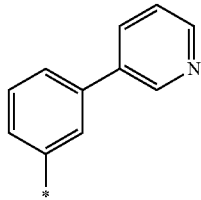
Formula 5-43
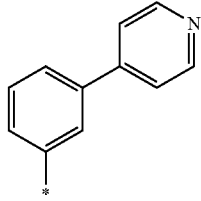
Formula 5-44
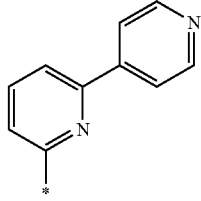
Formula 5-45
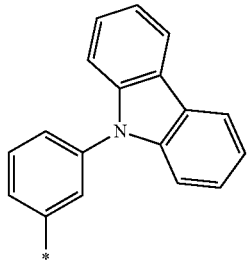

Formula 5-46
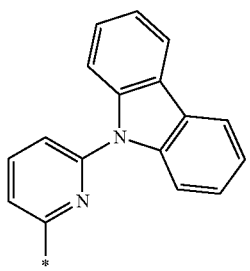
Formula 5-47
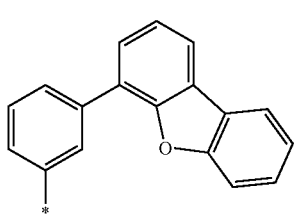
Formula 5-48
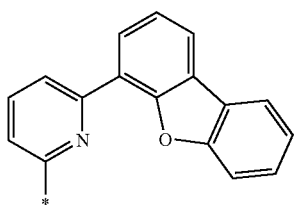
Formula 5-49
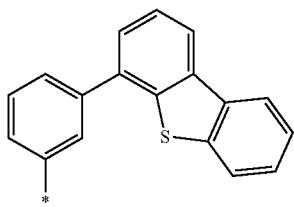
Formula 5-50
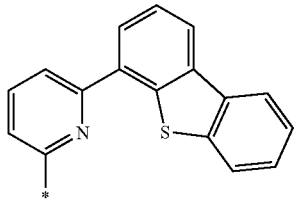
Formula 5-51
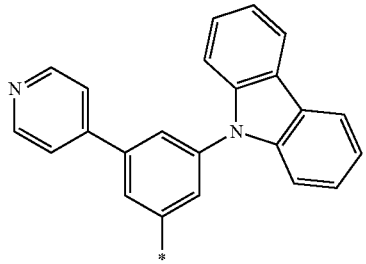
Formula 5-52
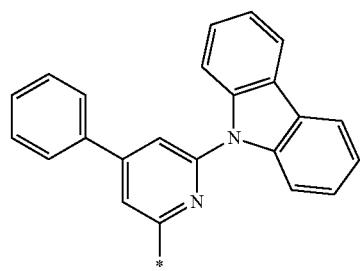
Formula 5-53
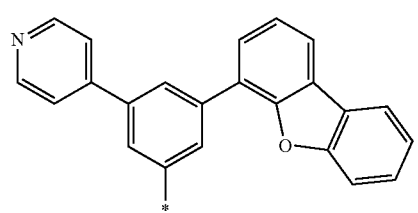
Formula 5-54
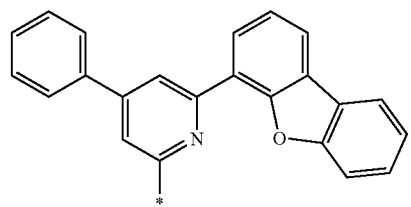
Formula 5-55
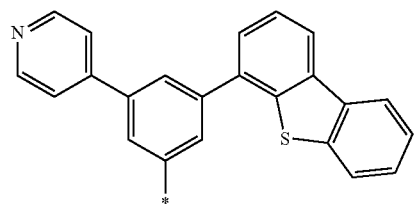
Formula 5-56
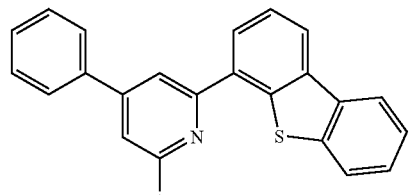
Formula 5-57
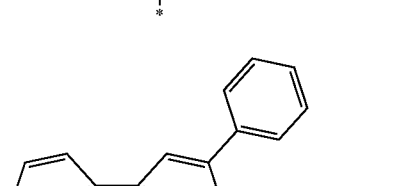

Formula 5-58
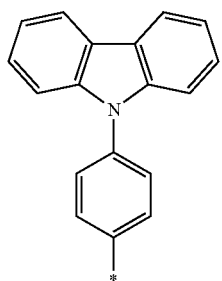
Formula 5-59
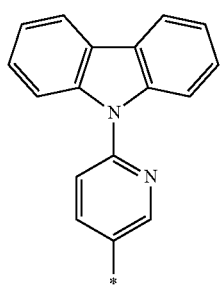
Formula 5-60
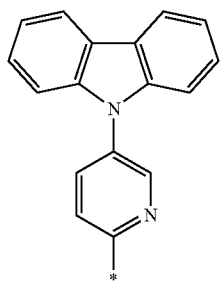
Formula 5-61
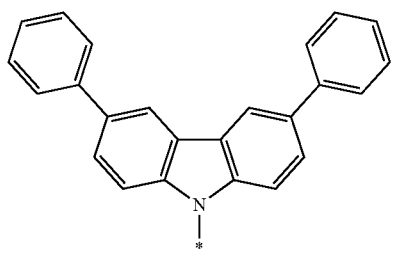
Formula 5-62
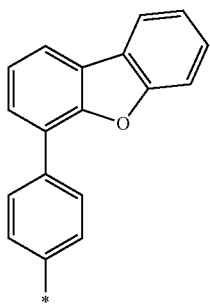
Formula 5-63
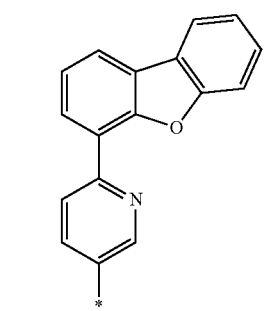
Formula 6-64
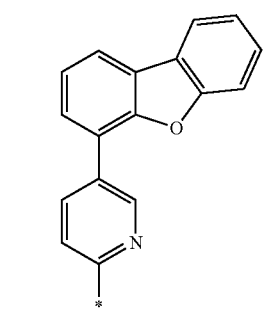
Formula 5-65
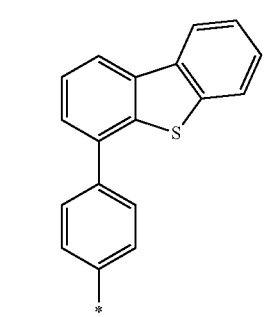
Formula 5-66
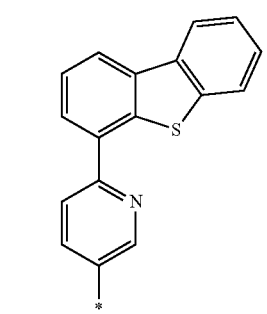
Formula 6-67
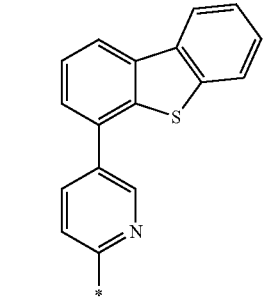

-continued
Formula 5-68
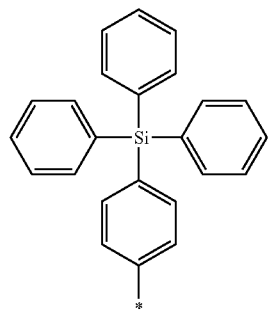
Formula 5-69
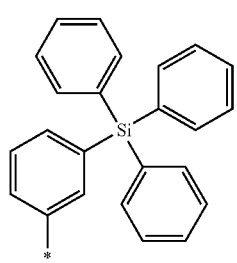
Formula 5-70
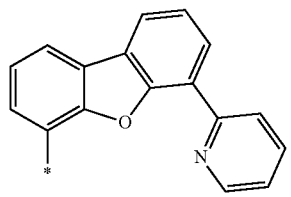
Formula 5-71
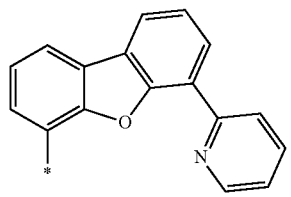
Formula 5-72
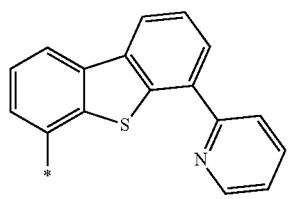
Formula 5-73
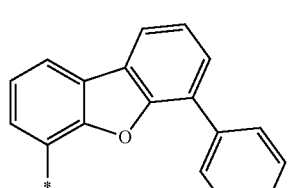
-continued
Formula 5-74
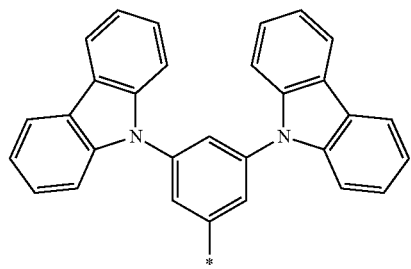
Formula 5-75
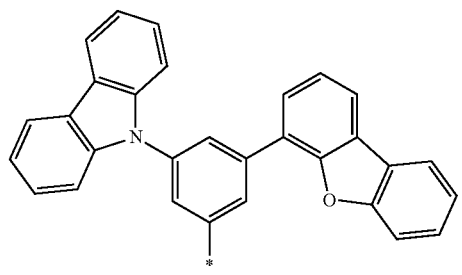
Formula 5-76
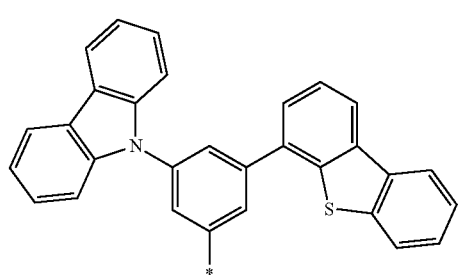
Formula 5-77
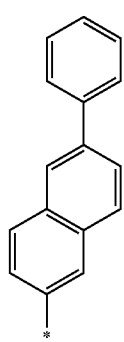
Formula 5-78
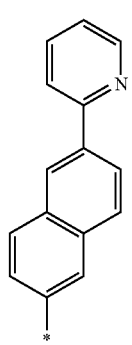

-continued

Formula 5-79

Formula 5-80 b1 in Formula 1 indicates the number of groups $R_1$, and may be an integer of 1 to 5, for example, an integer of 1 to 3. b1 may be 1 or 2, or 1. When b1 is 2 or more, a plurality of groups $R_1$ may be identical or different.

b11 in Formula 1 indicates the number of groups $R_{11}$, and may be an integer of 1 to 5, for example, an integer of 1 to 3. b11 may be 1 or 2, or 1. When b11 is 2 or more, a plurality of groups $R_{11}$ may be identical or different.

b12 in Formula 1 indicates the number of groups $R_{12}$, and may be an integer of 1 to 5, for example, an integer of 1 to 3. b12 may be 1 or 2, or 1. When b12 is 2 or more, a plurality of groups $R_{12}$ may be identical or different.

b13 in Formula 1 indicates the number of groups $R_{13}$, and may be an integer of 1 to 5, for example, an integer of 1 to 3. b13 may be 1 or 2, or 1. When b13 is 2 or more, a plurality of groups $R_{13}$ may be identical or different.

b14 in Formula 1 indicates the number of groups $R_{14}$, and may be an integer of 1 to 5, for example, an integer of 1 to 3. b14 may be 1 or 2, or 1. When b14 is 2 or more, a plurality of groups $R_{14}$ may be identical or different.

b21 in Formula 1 indicates the number of groups $R_{21}$, and may be an integer of 1 to 5, for example, an integer of 1 to 3. b21 may be 1 or 2, or 1. When b21 is 2 or more, a plurality of groups $R_{21}$ may be identical or different.

b22 in Formula 1 indicates the number of groups $R_{22}$, and may be an integer of 1 to 5, for example, an integer of 1 to 3. b22 may be 1 or 2, or 1. When b22 is 2 or more, a plurality of groups $R_{22}$ may be identical or different.

c21 in Formula 1 indicates the number of moieties represented by *-$(L_{21})_{a21}$-$(R_{21})$, and may be selected from an integer of 1 to 4. c21 may be 1 or 2. When c21 is 2 or more, groups *-$(L_{21})_{a21}$-$(R_{21})$ may be identical or different.

c22 in Formula 1 indicates the number of moieties represented by *-$(L_{22})_{a22}$-$(R_{22})$, and may be selected from an integer of 1 to 4. c22 may be 1 or 2. When c22 is 2 or more, groups *-$(L_{22})_{a22}$-$(R_{22})$ may be identical or different.

The condensed-cyclic compound may be represented by Formula 1A or 1B:

Formula 1A

Formula 1B $X_1$, $X_{11}$, $X_{12}$, $X_{13}$, $X_{14}$, $L_{21}$, a21, $R_{21}$, and b21 in Formulae 1A and 1B may be understood by referring to the description provided herein.

According to an embodiment, $X_1$ in Formulae 1A and 1B may be N-[$(L_1)_{a1}$-$(R_1)_{b1}$]. $L_1$, a1, $R_1$, and b1 may be understood by referring to the description provided herein.

According to another embodiment, $X_1$ in Formulae 1A and 1B may be C($R_2$)($R_3$), and $R_2$ and $R_3$ do not form a ring. $R_2$ to $R_3$ may be understood by referring to the description provided herein.

According to another embodiment, $X_1$ in Formulae 1 A and 1B may be S or O.

According to another embodiment, in Formulae 1A and 1B, $X_{11}$ may be N or C-[$(L_{11})_{a11}$-$(R_{11})_{b11}$],
$X_{12}$ may be N or C-[$(L_{12})_{a12}$-$(R_{12})_{b12}$],
$X_{13}$ may be N or C-[$(L_{13})_{a13}$-$(R_{13})_{b13}$], and
$X_{14}$ may be N or C-[$(L_{14})_{a14}$-$(R_{14})_{b14}$].

Herein, $L_{11}$ to $L_{14}$, a11 to a14, $R_{11}$ to $R_{14}$, and b11 to b14 may be understood by referring to the description provided therein.

According to an embodiment, in Formulae 1 A and 1B,
$X_{11}$ may be N,
$X_{12}$ may be C-[$(L_{12})_{a12}$-$(R_{12})_{b12}$],
$X_{13}$ may be C-[$(L_{13})_{a13}$-$(R_{13})_{b13}$], and
$X_{14}$ may be C-[$(L_{14})_{a14}$-$(R_{14})_{b14}$].

According to another embodiment, in Formulae 1A and 1B,
$X_{11}$ may be C-[$(L_{11})_{a11}$-$(R_{11})_{b11}$],
$X_{12}$ may be N,
$X_{13}$ may be C-[$(L_{13})_{a13}$-$(R_{13})_{b13}$], and
$X_{14}$ may be C-[$(L_{14})_{a14}$-$(R_{14})_{b14}$].

According to another embodiment, in Formulae 1A and 1B,
$X_{11}$ may be C-[$(L_{11})_{a11}$-$(R_{11})_{b11}$],
$X_{12}$ may be C-[$(L_{12})_{a12}$-$(R_{12})_{b12}$],
$X_{13}$ may be N, and
$X_{14}$ may be C-[$(L_{14})_{a14}$-$(R_{14})_{b14}$].

According to another embodiment, in Formulae 1A and 1B,
$X_{11}$ may be C-[$(L_{11})_{a11}$-$(R_{11})_{b11}$],
$X_{12}$ may be C-[$(L_{12})_{a12}$-$(R_{12})_{b12}$], $X_{13}$ may be C-[(L$_{13}$)$_{a13}$-(R$_{13}$)$_{b13}$], and
$X_{14}$ may be N.
According to another embodiment, in Formulae 1A and 1B,
$X_{11}$ may be N,
$X_{12}$ may be C-[(L$_{12}$)$_{a12}$-(R$_{12}$)$_{b12}$],
$X_{13}$ may be N, and
$X_{14}$ may be C-[(L$_{14}$)$_{a14}$-(R$_{14}$)$_{b14}$].
According to another embodiment, in Formulae 1A and 1B,
$X_{11}$ may be N,
$X_{12}$ may be C-[(L$_{12}$)$_{a12}$-(R$_{12}$)$_{b12}$],
$X_{13}$ may be C-[(L$_{13}$)$_{a13}$-(R$_{13}$)$_{b13}$], and
$X_{14}$ may be N.
According to another embodiment, the condensed-cyclic compound may be represented by Formula 1A(1) or 1B(1) below:

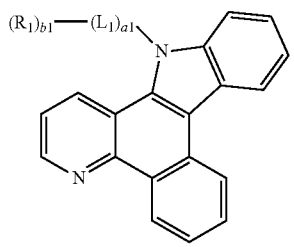

Formula 1A(1)

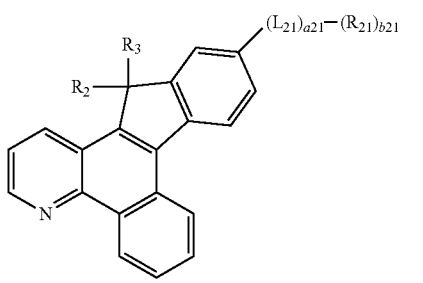

Formula 1B(1)

$L_1$, $L_{21}$, a1, a21, $R_1$ $R_2$, $R_3$, $R_{21}$, b1, and b21 in Formulae 1A(1) and 1B(1) may be understood by referring to the description provided herein.
In Formulae 1A(1) and 1B(1),
$L_1$ and $L_{21}$ may be each independently selected from Formulae 2-1 to 2-33 (for example, Formulae 3-1 to 3-38);
a1 and a21 may be each independently 0 or 1;
$R_1$ may be selected from Formulae 4-1 to 4-31 (for example, Formulae 5-1 to 5-80);
$R_{21}$ may be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group; Formulae 4-1 to 4-31 below (for example, Formulae 5-1 to 5-80); and —Si(Q$_3$)(Q$_4$)(Q$_5$);
$Q_3$ to $Q_5$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group; and
b1 and b21 may be each independently 1 or 2, but they are not limited thereto. According to an embodiment, in the present specification, at least one of the substituted $C_3$-$C_{10}$ cycloalkylene group, the substituted $C_3$-$C_{10}$ heterocycloalkylene group, the substituted $C_3$-$C_{10}$ cycloalkenylene group, the substituted $C_3$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic hetero-condensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_3$-$C_{10}$ heterocycloalkyl group, the substituted $C_3$-$C_{10}$ cycloalkenyl group, the substituted $C_3$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ hetero aryl group, the substituted monovalent non-aromatic condensed polycyclic group, and the substituted monovalent non-aromatic hetero-condensed polycyclic group may be substituted with a group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a cyclopentyl group, a cyclohexyl group, a cycloheptyl group, a cyclopentenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, an imidazopyridinyl group, —N($Q_{11}$)($Q_{12}$), —Si($Q_{13}$)($Q_{14}$)($Q_{15}$), and —B($Q_{16}$)($Q_{17}$);

a cyclopentyl group, a cyclohexyl group, a cycloheptyl group, a cyclopentenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group;

a cyclopentyl group, a cyclohexyl group, a cycloheptyl group, a cyclopentenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, an imidazopyridinyl group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$); wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group.

The condensed-cyclic compound may be one of Compounds 1 to 117 below, but is not limited thereto.

1

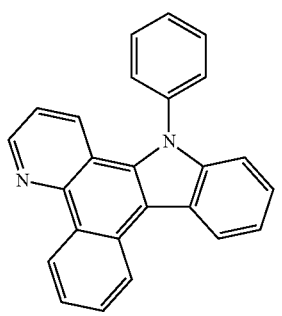

2

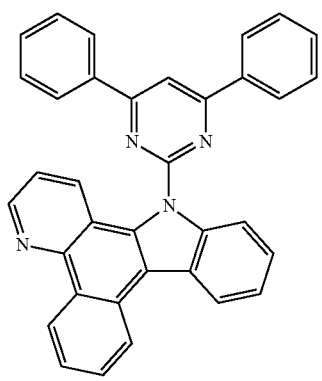

3

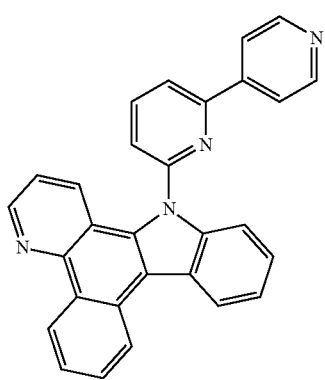

4

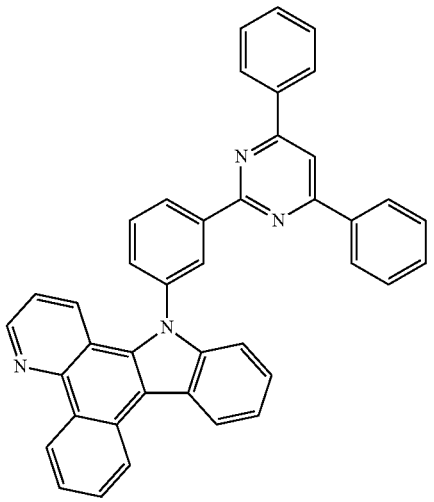

5

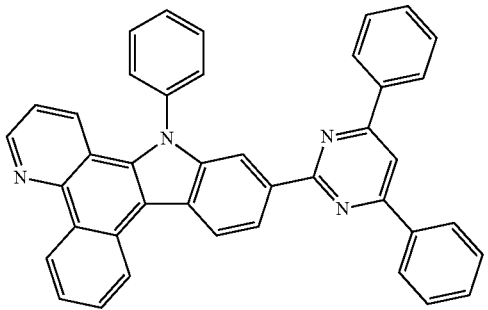

6

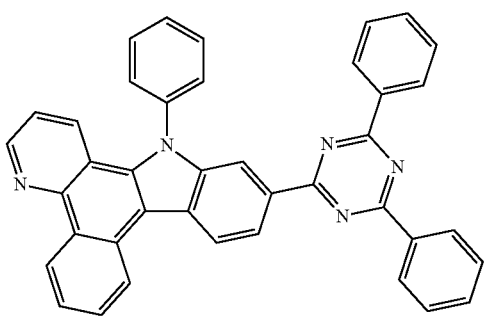

7

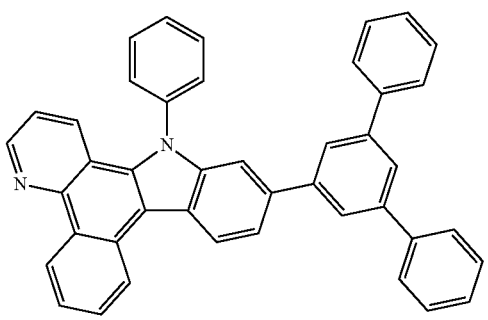

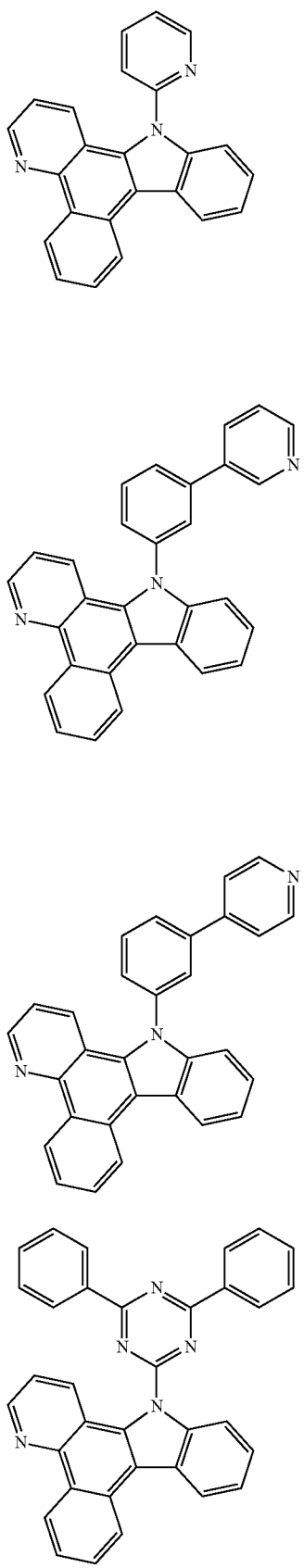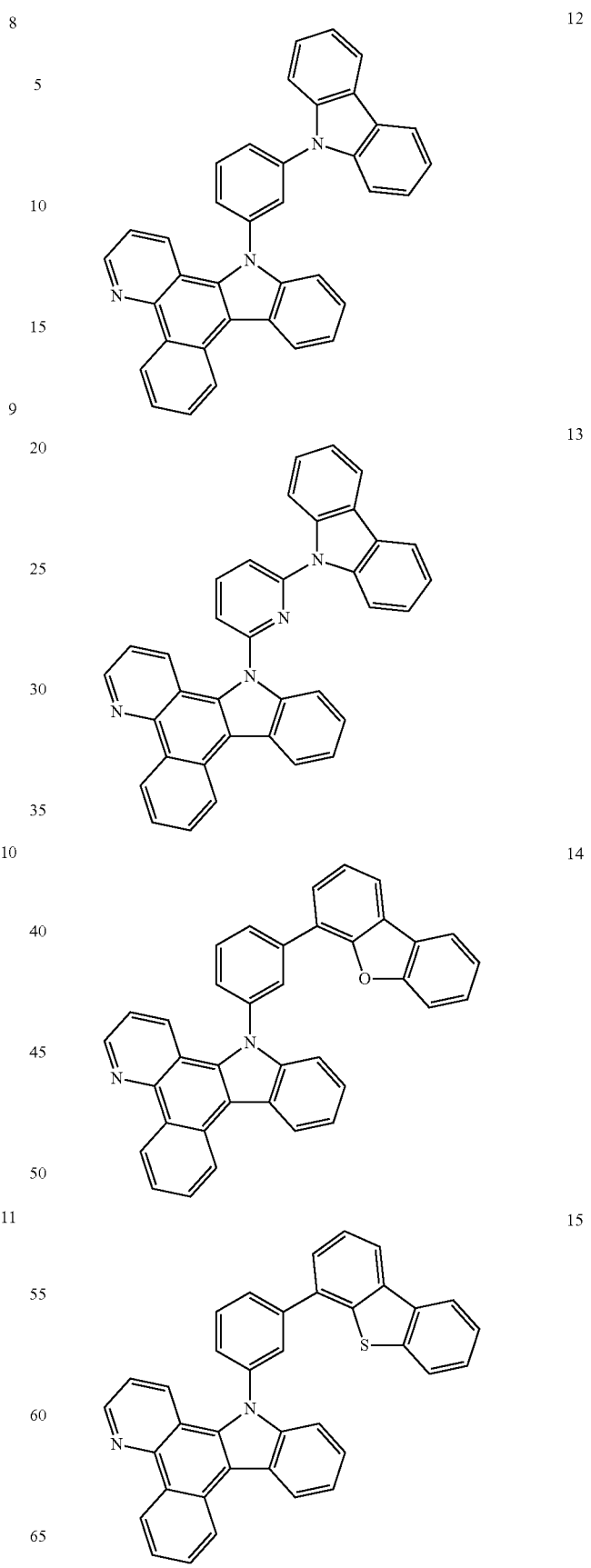

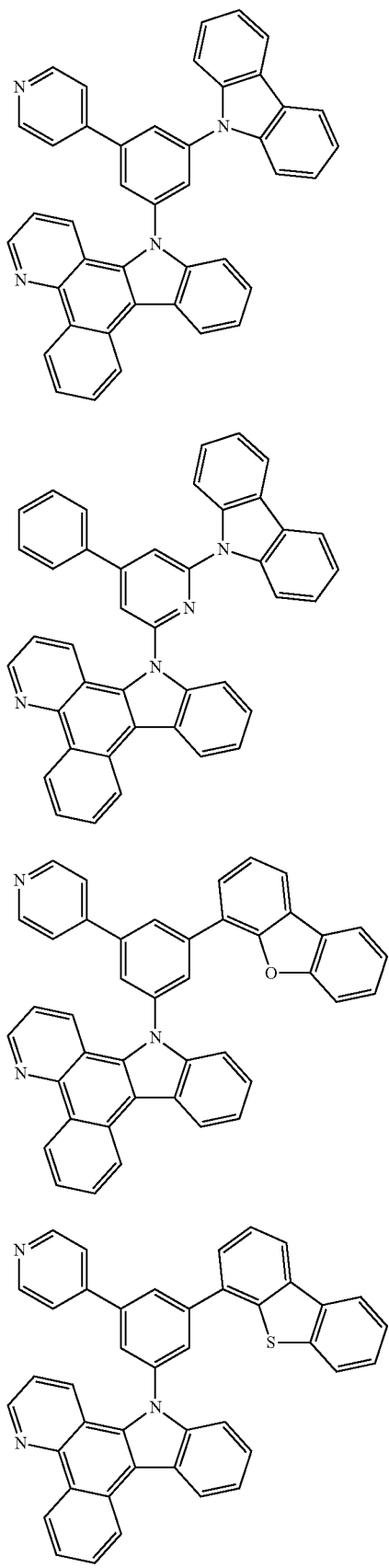
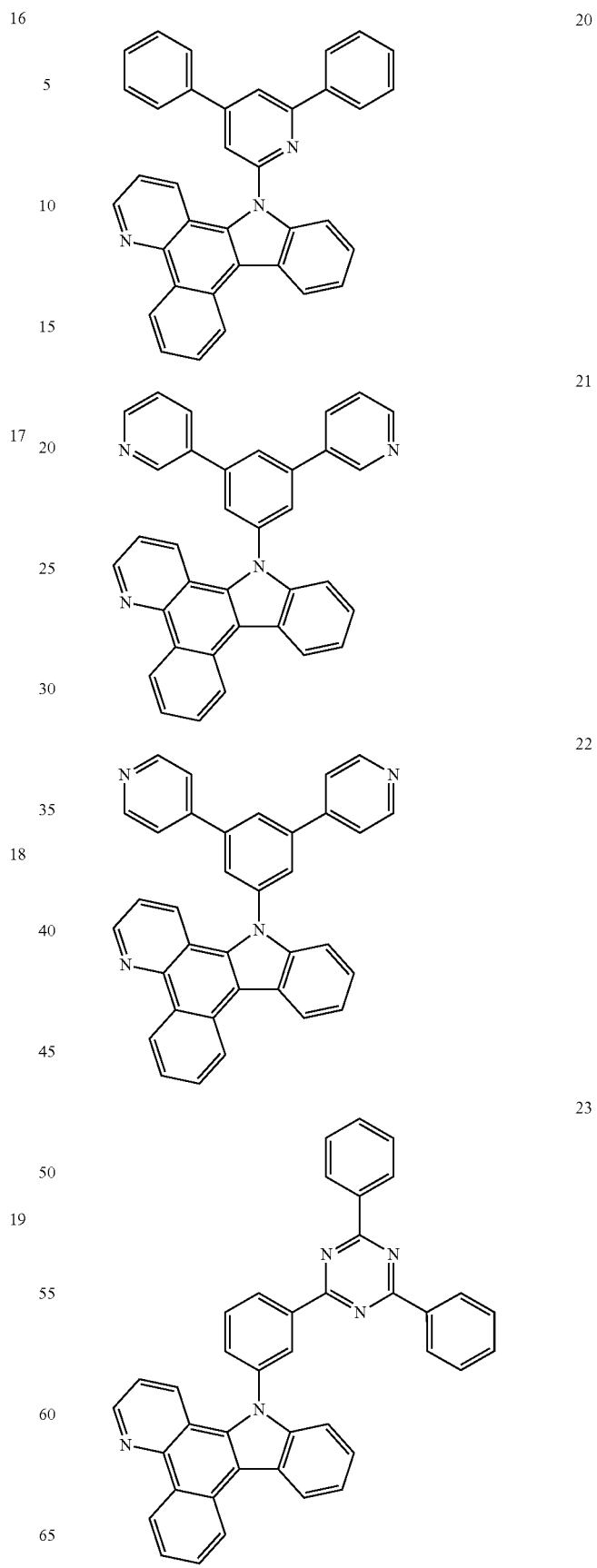

24
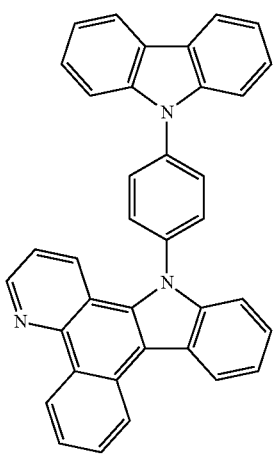
25
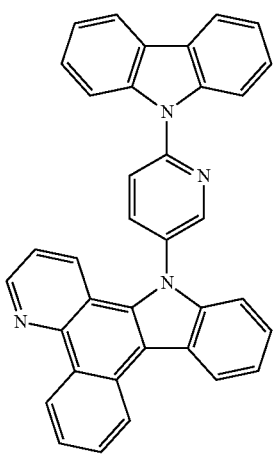
26
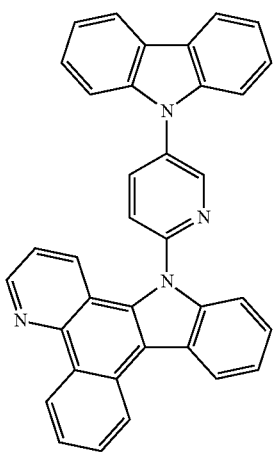
27
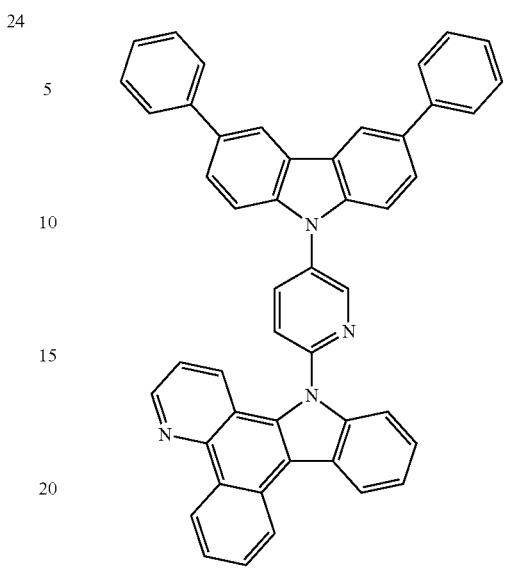
28
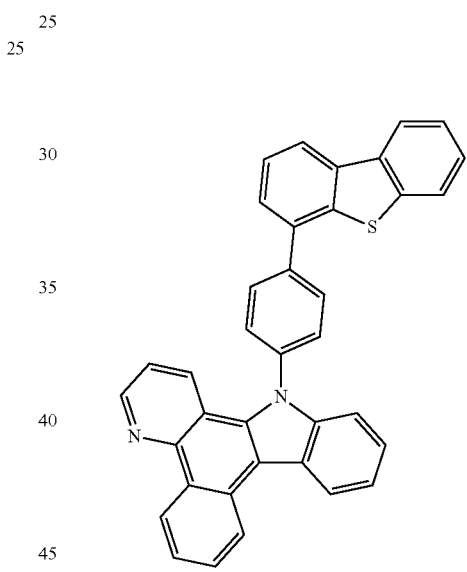
29
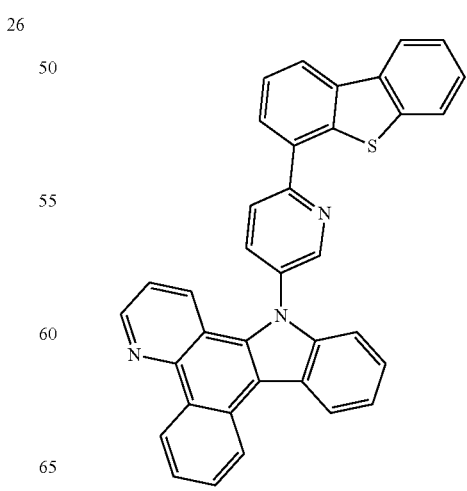

30
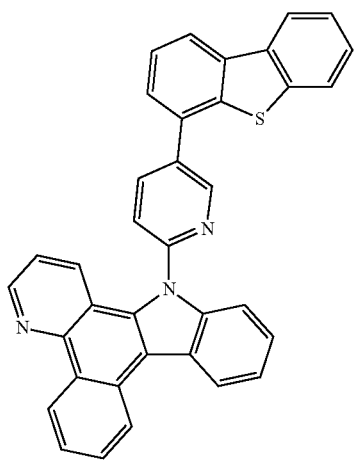
31
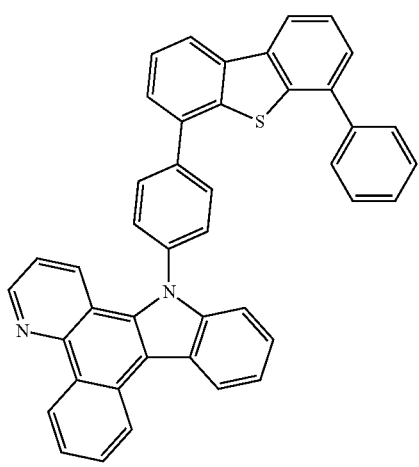
32
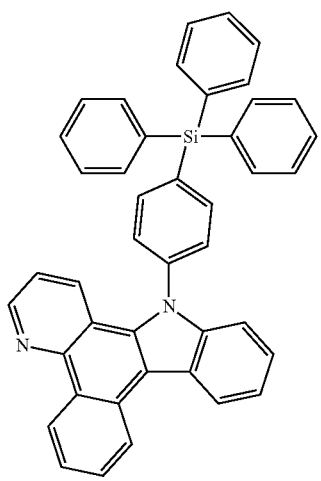
33
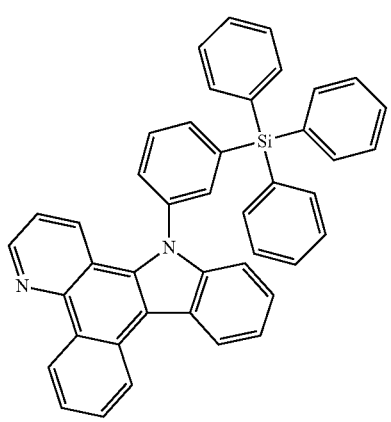
34
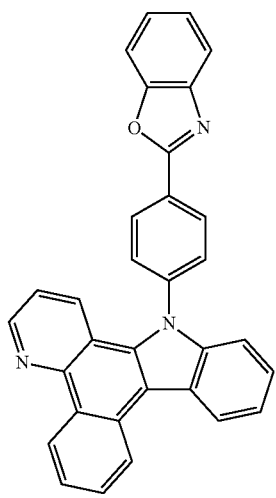
35
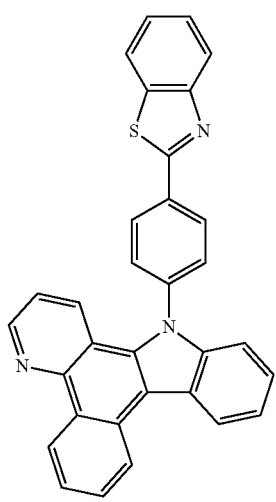

36
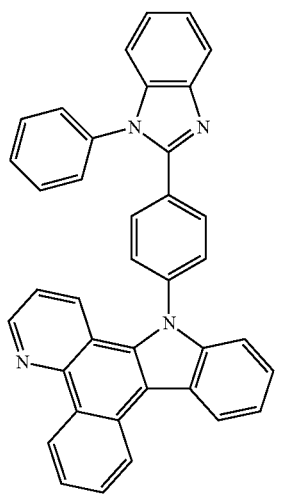
37
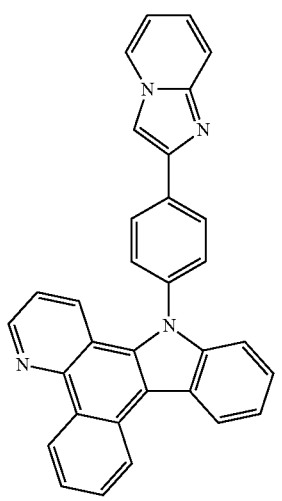
38
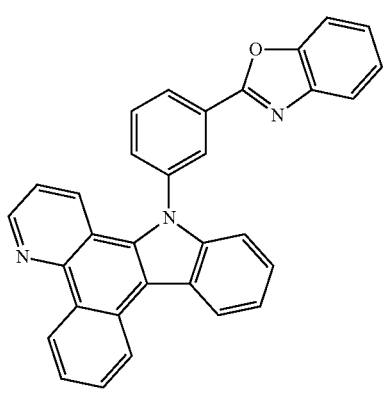
39
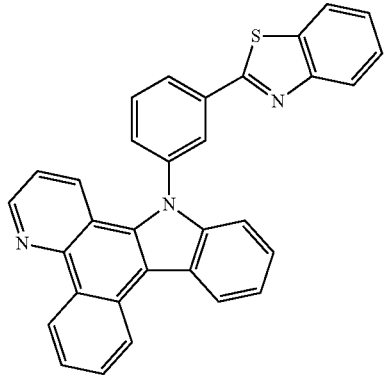
40
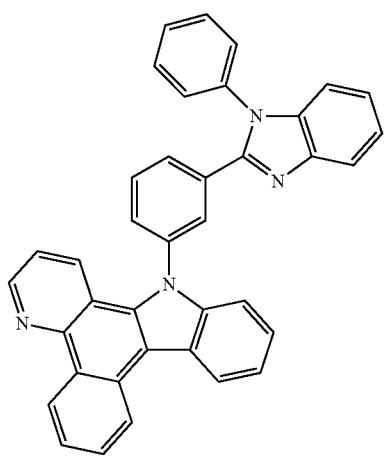
41
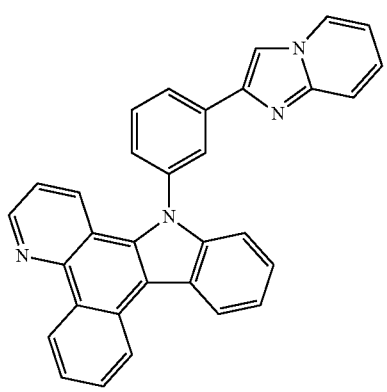
42
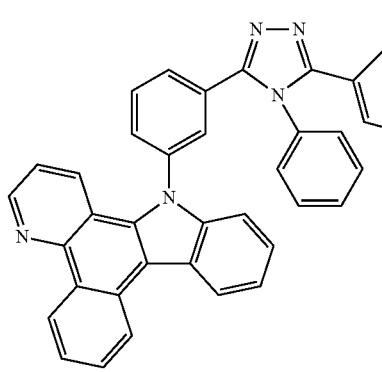

43
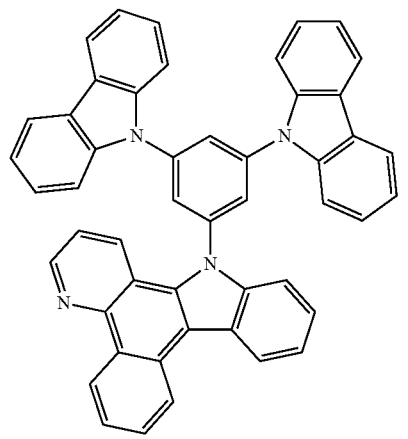
44
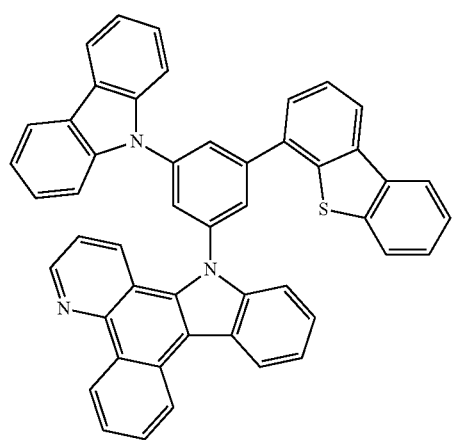
45
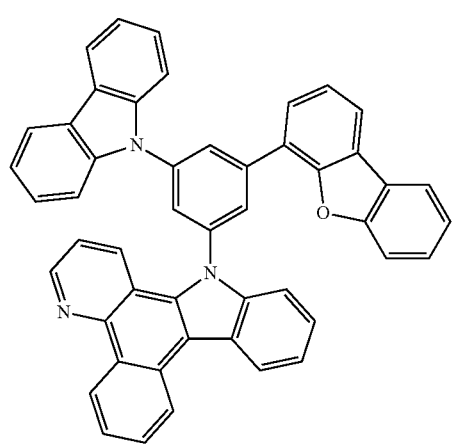
46
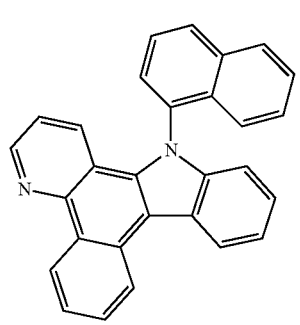
47
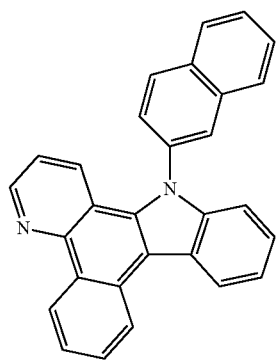
48
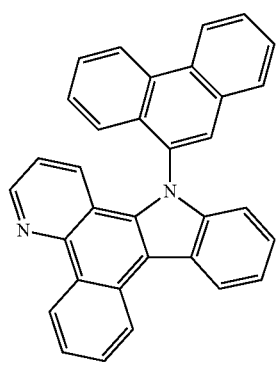
49
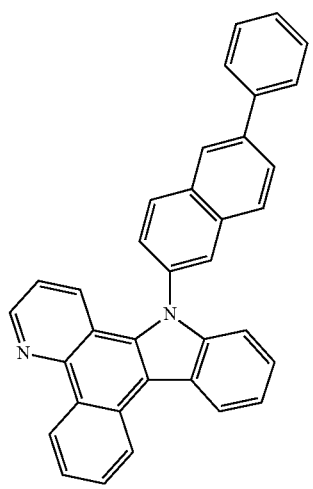

50
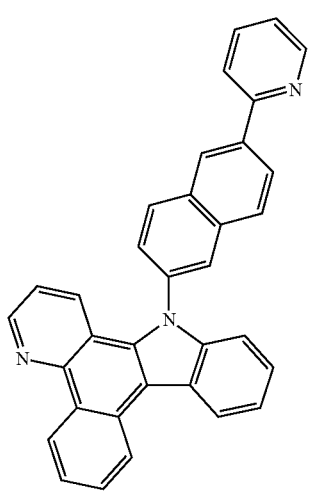
51
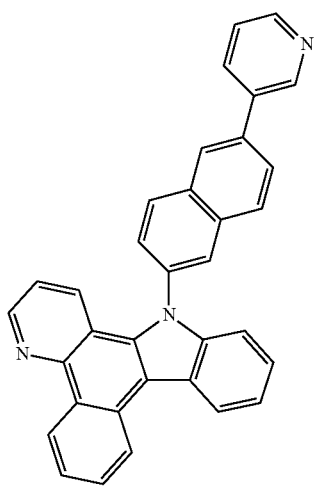
52
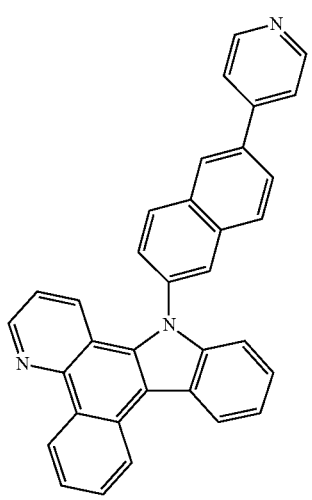
53
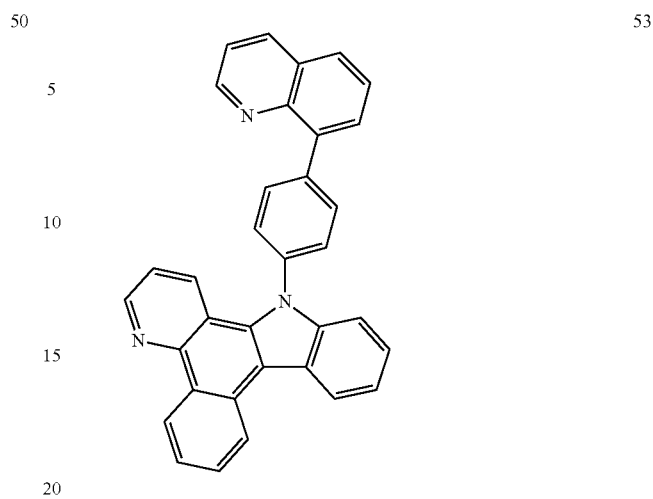
54
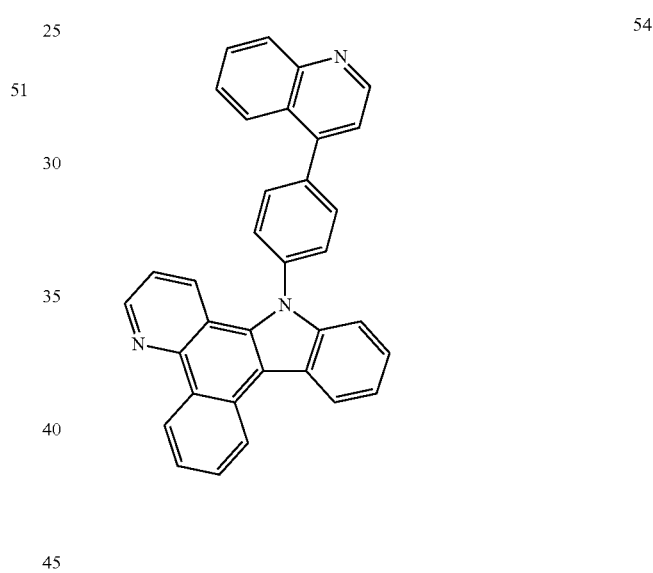
55
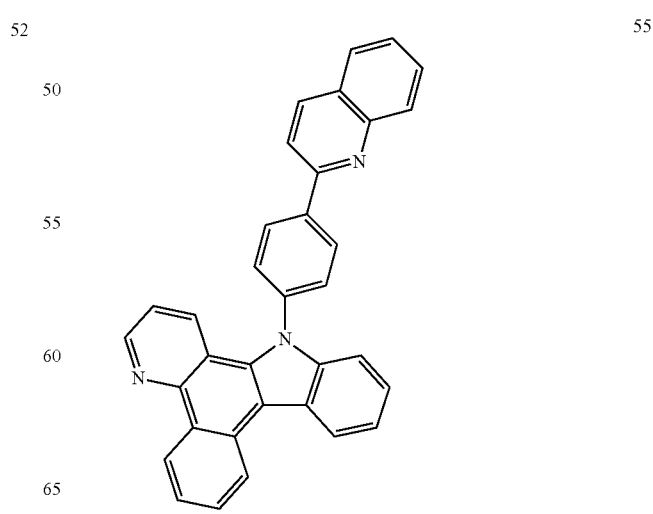

56
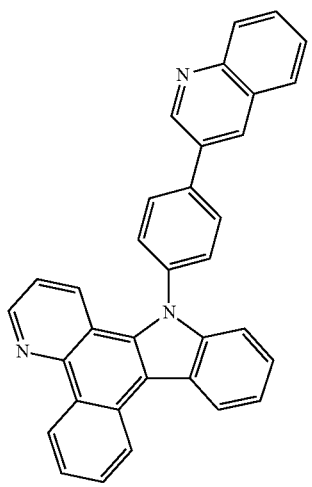
57
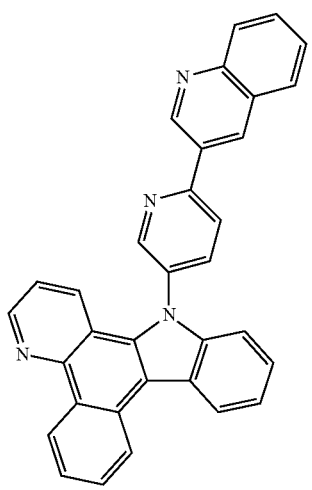
58
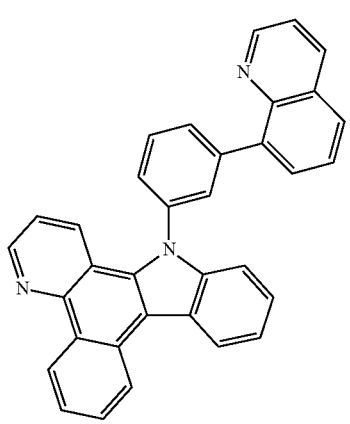
59
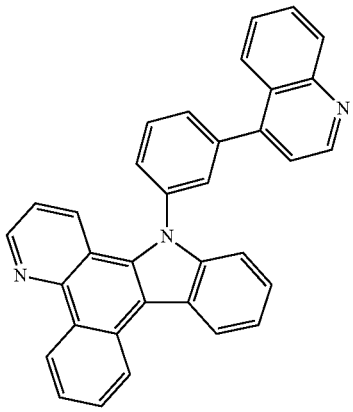
60
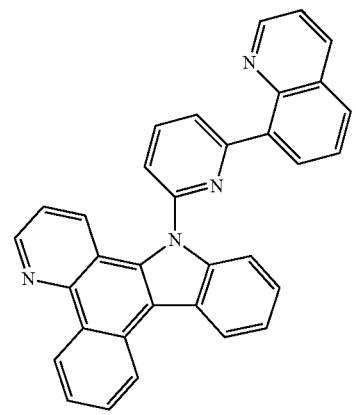
61
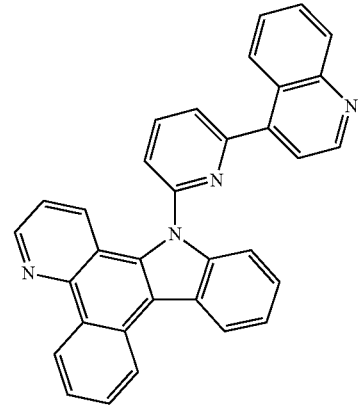
62
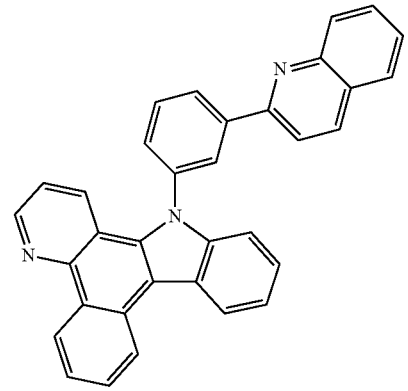

63
-continued
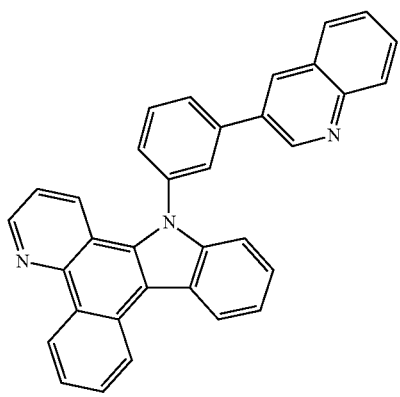
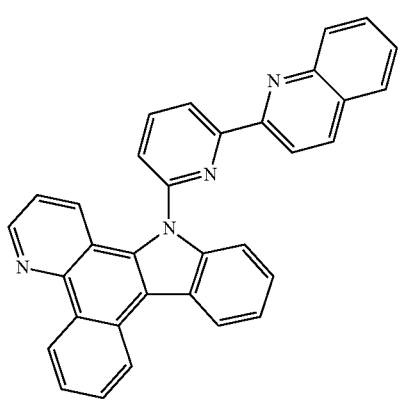
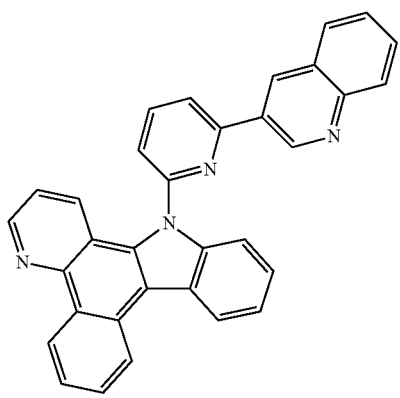
64
-continued
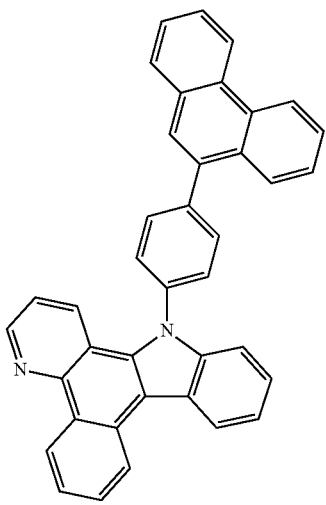
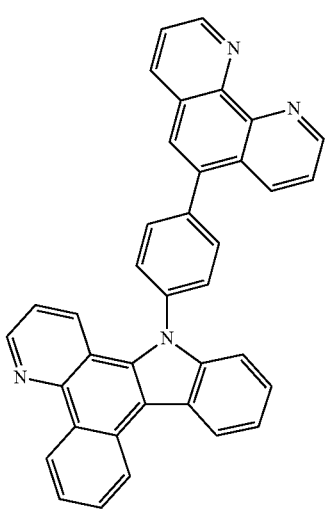
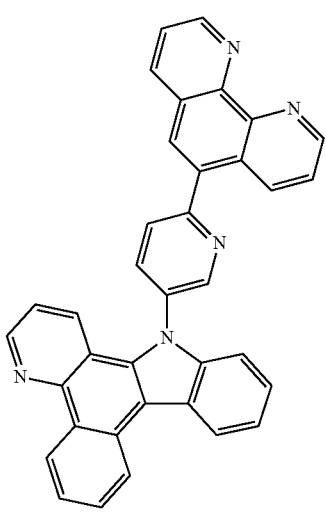

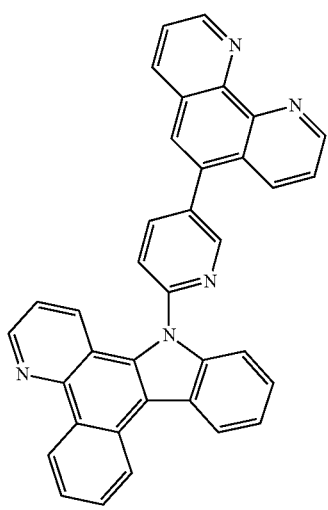
69
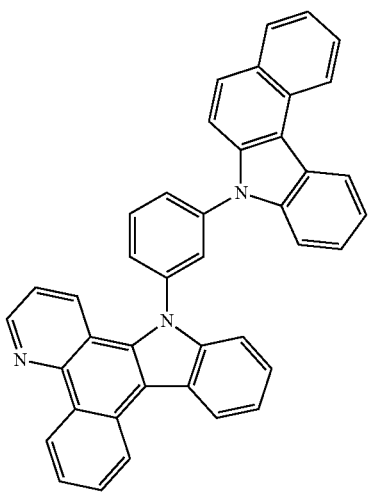
72
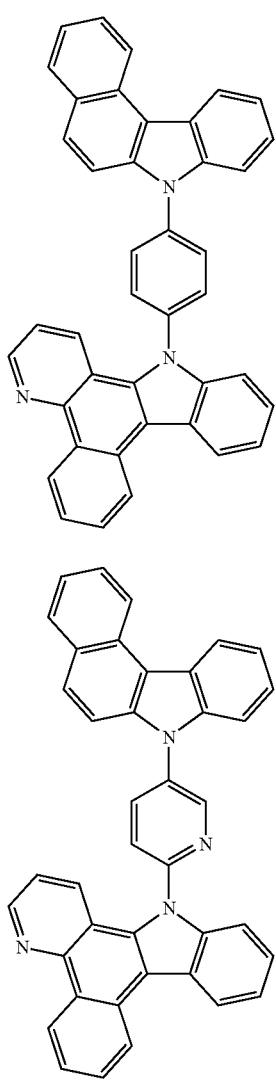
70
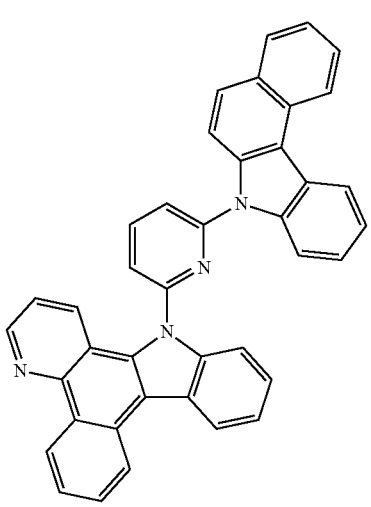
73
71
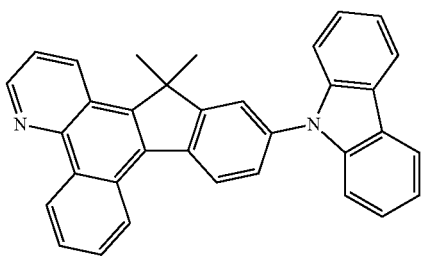
74
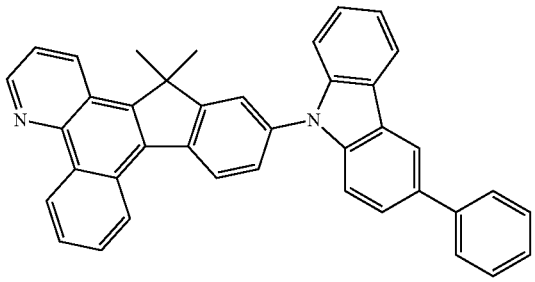
75

76
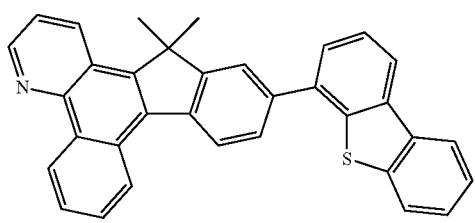
77
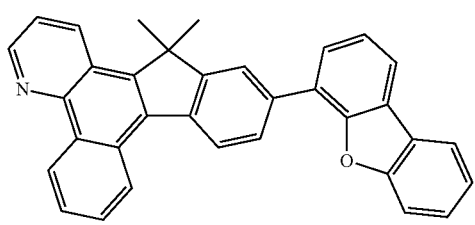
78
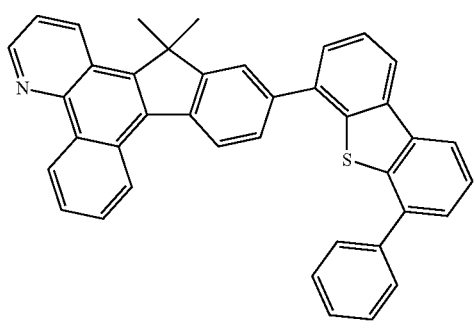
79
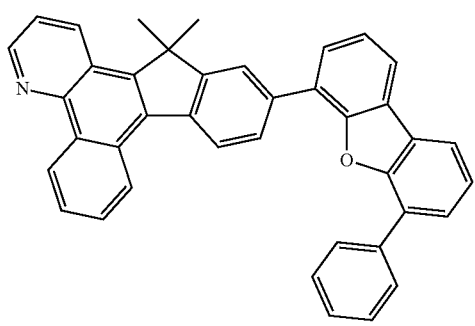
80
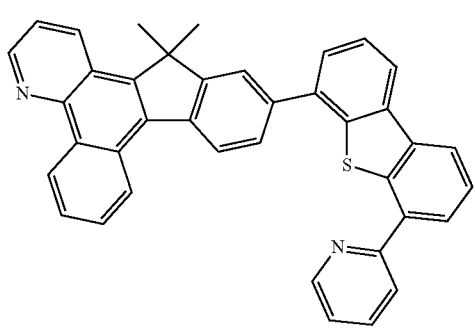
81
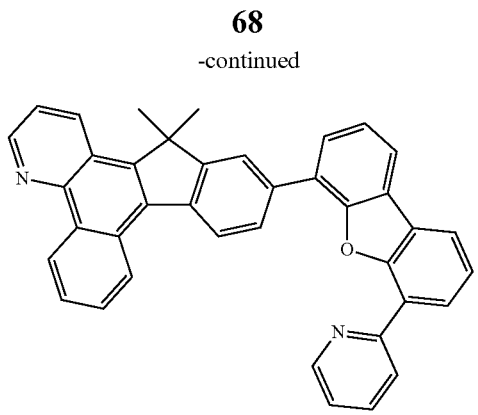
82
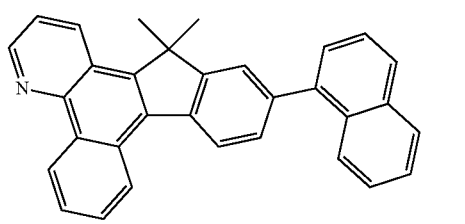
83
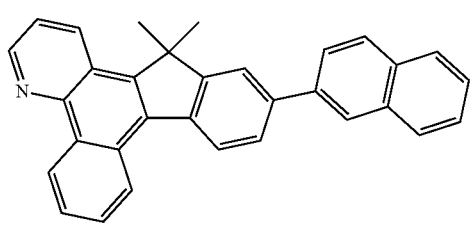
84
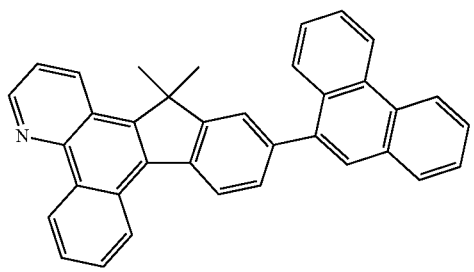
85
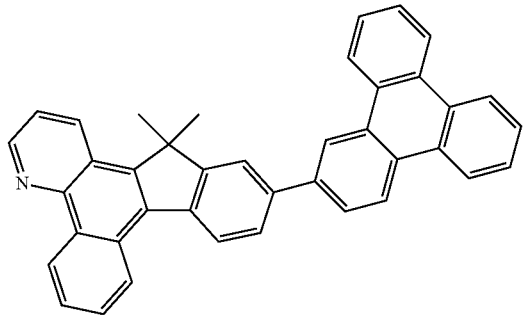

86
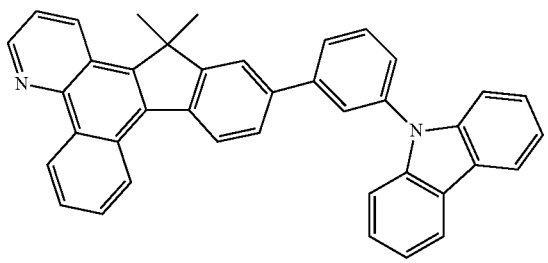
87
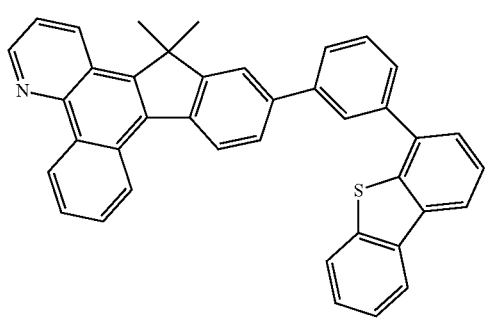
88
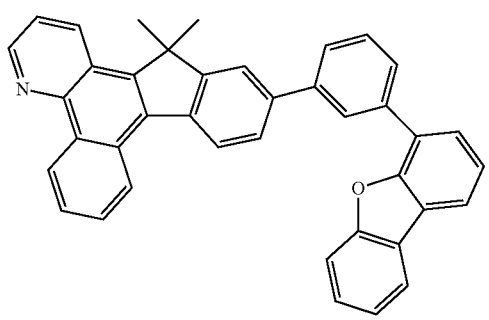
89
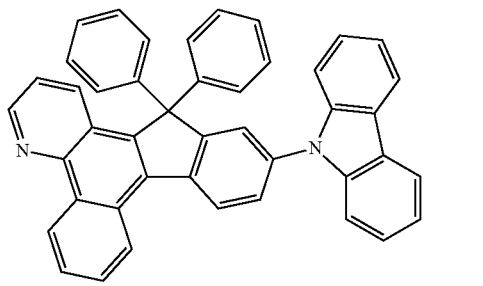
90
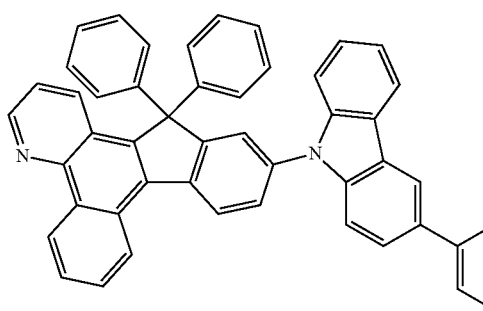
91
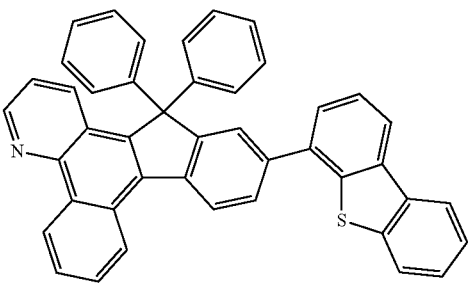
92
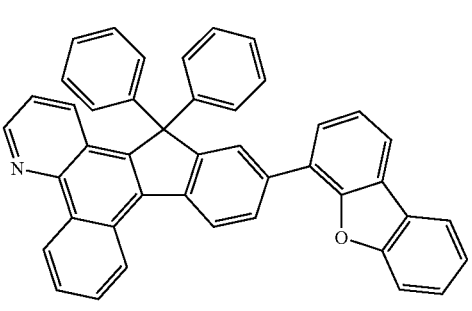
93
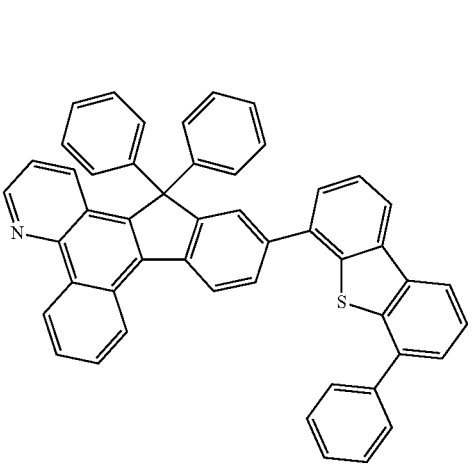
94
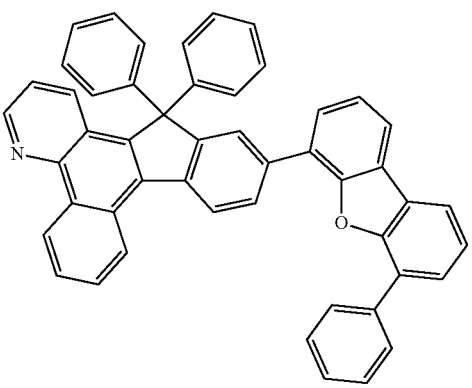

95
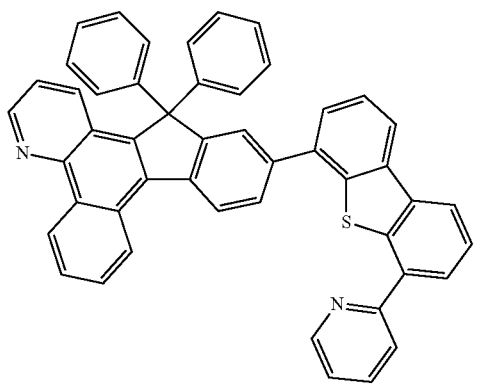
96
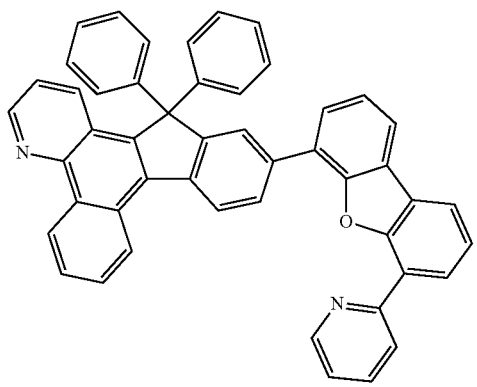
97
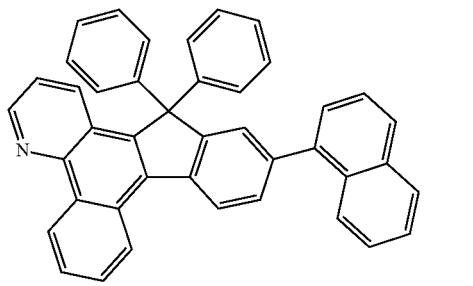
98
99
100
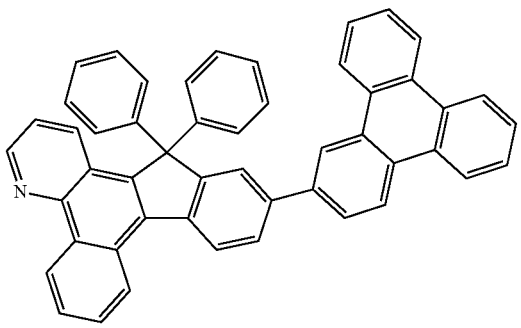
101
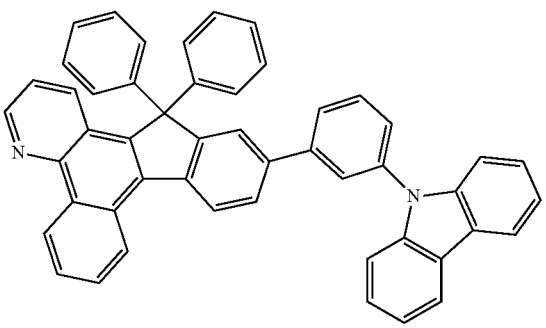
102
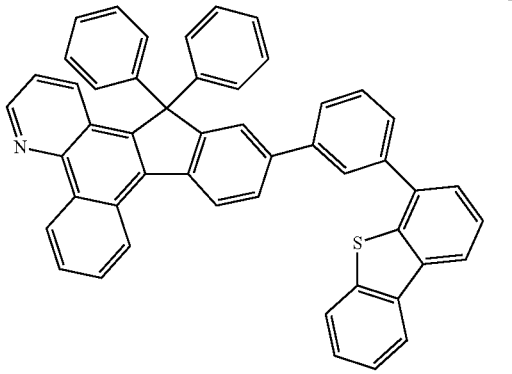
103
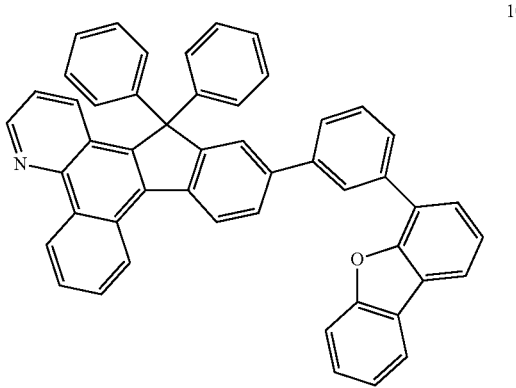

-continued
104
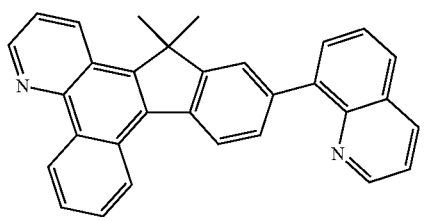
105
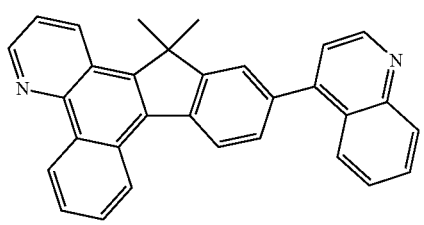
106
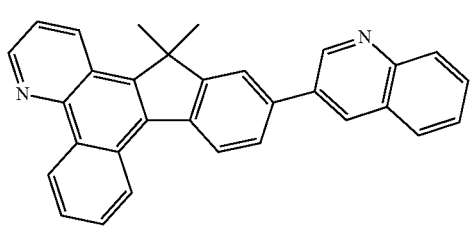
107
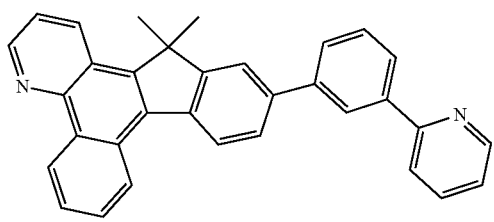
108
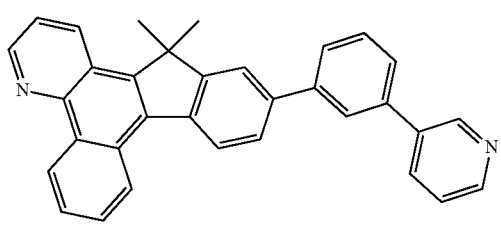
109
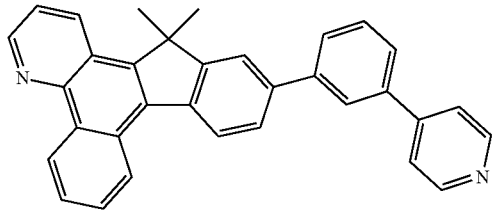
-continued
110
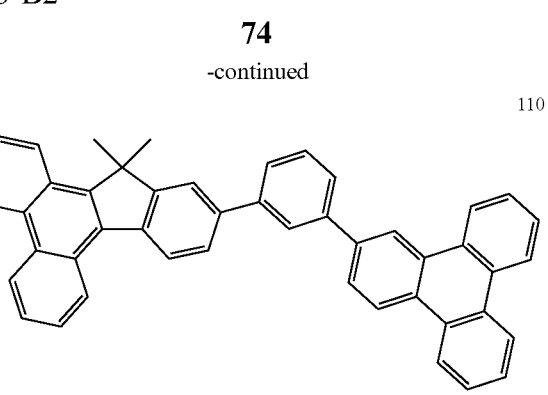
111
112
113
114
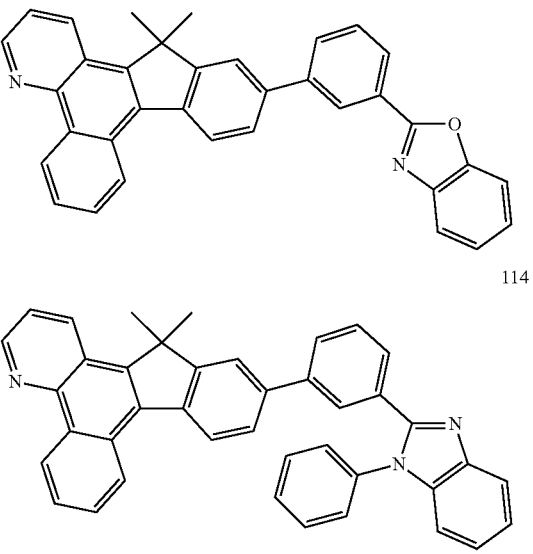

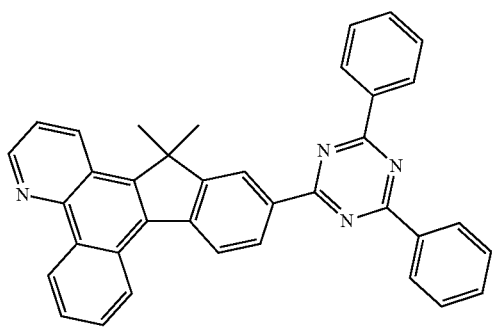

115

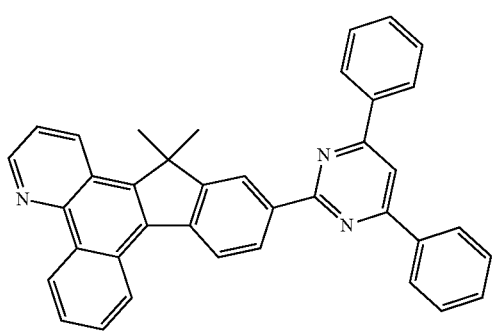

116

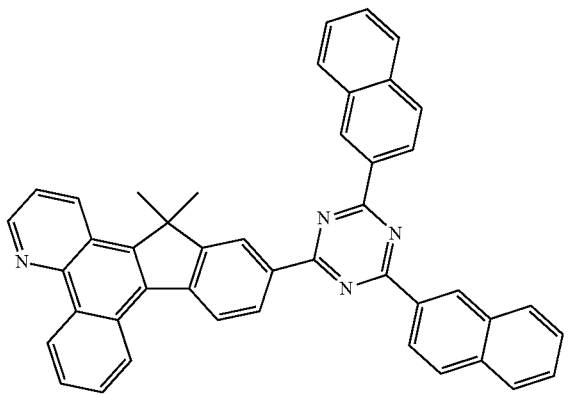

117

The condensed-cyclic compound includes at least one N as a ring-forming element in Ring A and includes only C as a ring-forming element in Ring B (see Formula 1'), thus making it possible to control HOMO and LUMO in the condensed-cyclic compound represented by Formula 1. Accordingly, an organic light-emitting device including the condensed-cyclic compound may have improved efficiency. Also, since $R_2$ and $R_3$ are not connected to form a ring (see Formula 1" below), when $X_2$ in the condensed-cyclic compound is $C(R_2)(R_3)$ or $Si(R_2)(R_3)$, it is possible to control a T1 energy level of the condensed-cyclic compound repre-sented by Formula 1. Accordingly, an organic light-emitting device including the condensed-cyclic compound may have a low driving voltage and high efficiency.

Formula 1'

Ring A

Ring B

Formula 1"

$R_2$ and $R_3$ do not bind to each other to form a ring

HOMO, LUMO, and $T_1$ energy level of Compounds A, B, and C were evaluated by using density functional theory (DFT) of the Gaussian program at the level of B3LYP/6-31 G(d,p), and results thereof are shown in Table 1:

Compound A

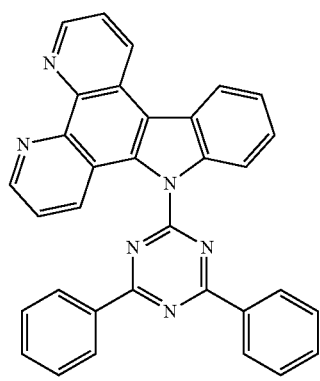

-continued

Compound B

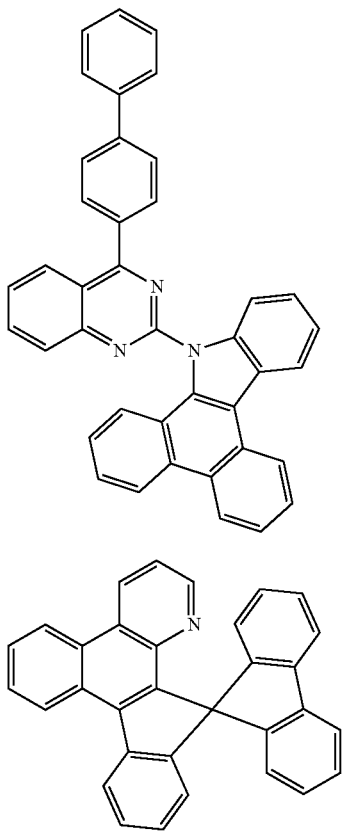

Compound C

TABLE 1

|  | HOMO (eV) | LUMO (eV) | T₁ energy level (eV) |
| --- | --- | --- | --- |
| Compound A | −5.653 | −2.119 | 2.519 |
| Compound B | −5.130 | −2.092 | 2.374 |
| Compound C | −5.500 | −1.486 | 2.389 |

Referring to Table 1, Compound A has a low LUMO energy level (negative value). A light-emission zone of an organic light-emitting device including Compound A is shifted to the interface between a hole transport region and an emission layer, and accordingly, the lifespan of the organic light-emitting device may decrease.

Also, referring to Table 1, Compounds B and C have low T1 energy levels. Accordingly, Compound B or C may be not suitable for use as a phosphorescent host that is to be used together with a green phosphorescent dopant. Also, since Compound C has a very high LUMO energy level (negative value), in an organic light-emitting device including Compound C, the movement of charges from an electron transport region to an emission layer may not be easy, leading to a decrease in efficiency of an organic light-emitting device and an increase in a driving voltage.

A synthesis method of the condensed-cyclic compound represented by Formula 1 may be understandable to one of ordinary skill in the art by referring to Synthesis Examples 1 to 3.

Accordingly, the condensed-cyclic compound represented by Formula 1 is suitable for use in an organic layer of an organic light-emitting device, for example, for use as a host in an emission layer of the organic layer. Thus, another aspect provides an organic light-emitting device that includes:
a first electrode;
a second electrode; and
an organic layer that is disposed between the first and second electrodes, including an emission layer and at least one of the condensed-cyclic compound represented by Formula 1.

The organic light-emitting device may have a low driving voltage, high efficiency, high brightness, and a long lifespan, due to the inclusion of an organic layer including the condensed-cyclic compound represented by Formula 1.

The condensed-cyclic compound of Formula 1 may be used between a pair of electrodes of an organic light-emitting device. For example, the condensed-cyclic compound may be included in at least one region selected from
i) a hole transport region (including, for example, at least one of a hole injection layer, a hole transport layer, a buffer layer, and an electron blocking layer) that is disposed between the first electrode and the emission layer, and
ii) an electron transport region (including, for example, at least one region selected from a hole blocking layer, an electron transport layer, and an electron injection layer) that is disposed between the emission layer and the second electrode.

For example, the condensed-cyclic compound represented by Formula 1 may be included in the emission layer. The emission layer may be a green emission layer that emits green light, and the dopant may be a phosphorescent dopant.

The expression "(an organic layer) includes at least one condensed-cyclic compound", as used herein, may refer to an organic layer including one condensed-cyclic compound of Formula 1 and an organic layer including two or more different condensed-cyclic compounds of Formula 1.

For example, the organic layer may include, as the condensed-cyclic compound, only Compound 1. In this regard, Compound 1 may exist in an emission layer of the organic light-emitting device. In another embodiment, the organic layer may include, as the condensed-cyclic compound, Compound 1 and Compound 2. In this regard, Compound 1 and Compound 2 may exist in either the same layer (for example, Compound 1 and Compound 2 all may exist in an emission layer), or different layers.

For example, the first electrode is an anode, and the second electrode is a cathode, and the organic layer includes
i) a hole transport region that is disposed between the first electrode and the emission layer and includes at least one of a hole injection layer, a hole transport layer, and an electron blocking layer, and
ii) an electron transport region that is disposed between the emission layer and the second electrode and includes at least one region selected from a hole blocking layer, an electron transport layer, and an electron injection layer.

The expression "organic layer", as used herein, refers to a single layer and/or a plurality of layers interposed between the first and second electrodes of an organic light-emitting device. The "organic layer" may include, in addition to an organic compound, an organometallic complex including metal.

FIG. 1 is a schematic view of an organic light-emitting device 10 according to an embodiment. Hereinafter, the structure of an organic light-emitting device according to an embodiment and a method of manufacturing an organic light-emitting device, according to an embodiment, will be described in connection with FIG. 1. The organic light-emitting device 10 includes a first electrode 11, an organic layer 15, and a second electrode 19, which are sequentially stacked.

In FIG. 1, a substrate may be additionally disposed under the first electrode 11 or above the second electrode 19. For use as the substrate, any substrate that is used in general organic light-emitting devices may be used, and the substrate may be a glass substrate or transparent plastic substrate, each with excellent mechanical strength, thermal stability, transparency, surface smoothness, ease of handling, and water repellency.

The first electrode 11 may be formed by depositing or sputtering a material for forming the first electrode 11 on the substrate. The first electrode 11 may be an anode. The material for the first electrode 11 may be selected from materials with a high work function to make holes be easily injected. The first electrode 13 may be a reflective electrode or a transmissive electrode. The material for the first electrode 13 may be an indium tin oxide (ITO), indium zinc oxide (IZO), tin oxide ($SnO_2$), or zinc oxide (ZnO). According to another embodiment, the material for the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layer structure or a multi-layer structure including two or more layers.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one of a hole injection layer, a hole transport layer, an electron blocking layer, and a buffer layer.

The hole transport region may include only either a hole injection layer or a hole transport layer. According to another embodiment, the hole transport region, may have a structure of hole injection layer/hole transport layer or hole injection layer/hole transport layer/electron blocking layer, which are sequentially stacked in this stated order from the first electrode 11.

When the hole injection region includes a hole injection layer, the hole injection layer may be formed on the first electrode 11 by using any one of various methods, for example, by vacuum deposition, spin coating, casting, or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Angstrom per second (Å/sec). However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for a hole transport layer and an electron blocking layer may be understood by referring to conditions for forming the hole injection layer.

The hole transport region may include at least one compound selected from m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

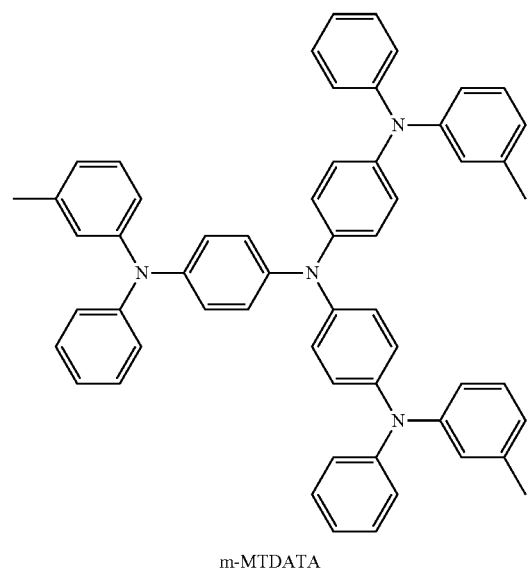

m-MTDATA

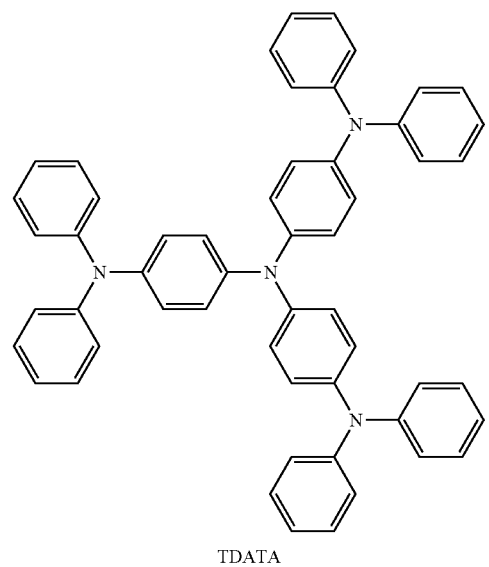

TDATA

-continued
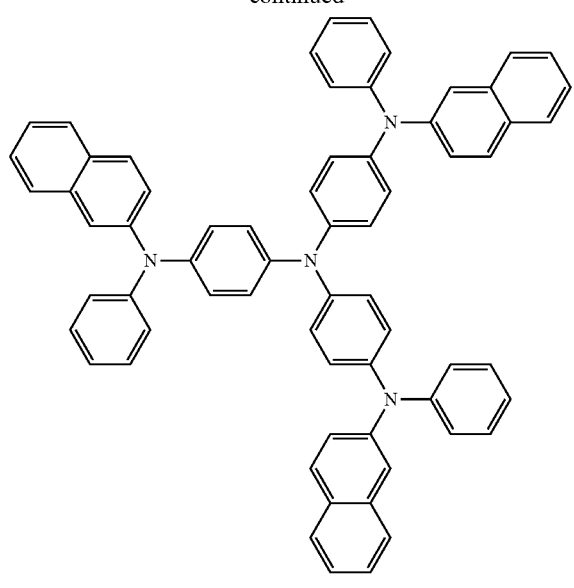
2-TNATA
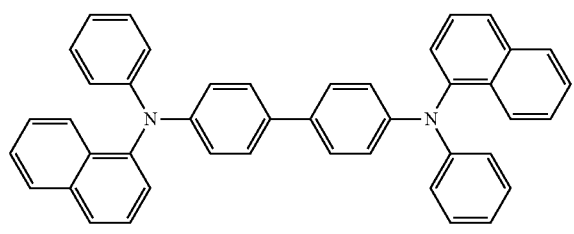
NPB
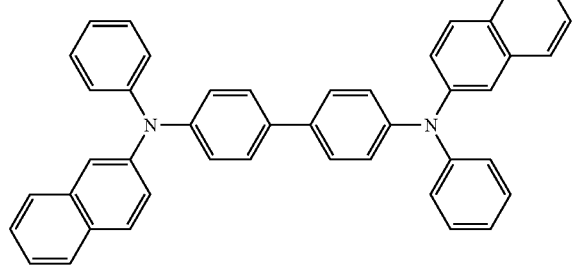
β-NPB
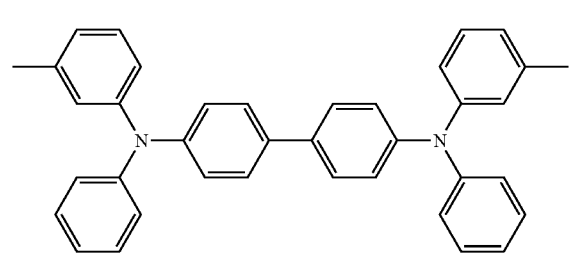
TPD
-continued
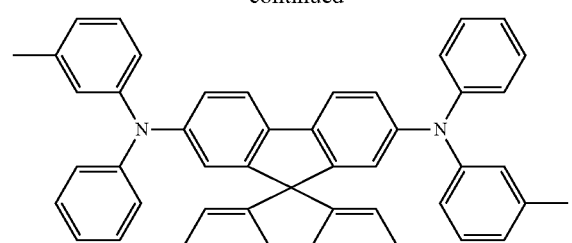
Spiro-TPD
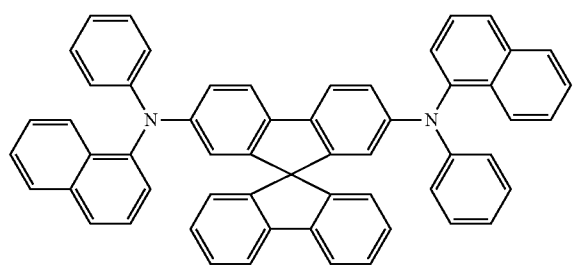
Spiro-NPB
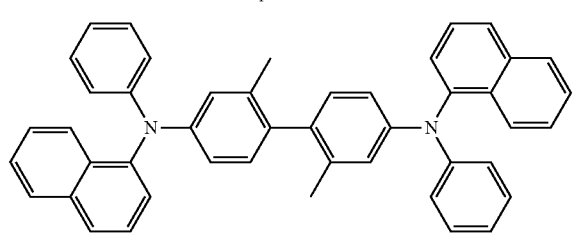
α-NPB
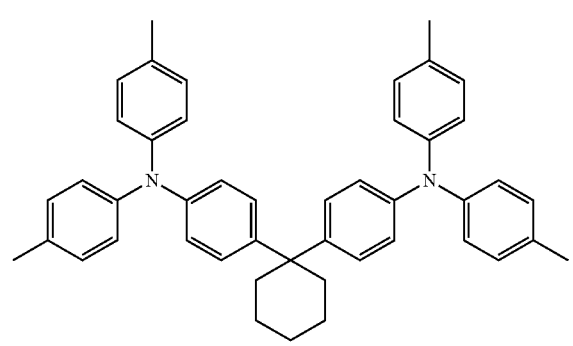
TAPC
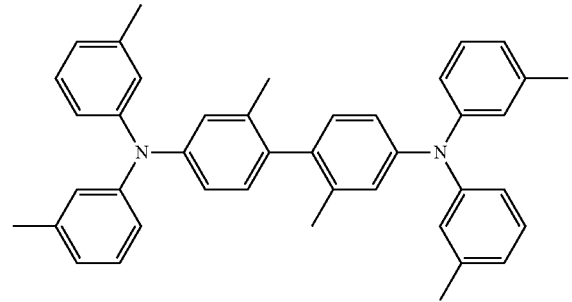
HMTPD -continued Formula 201

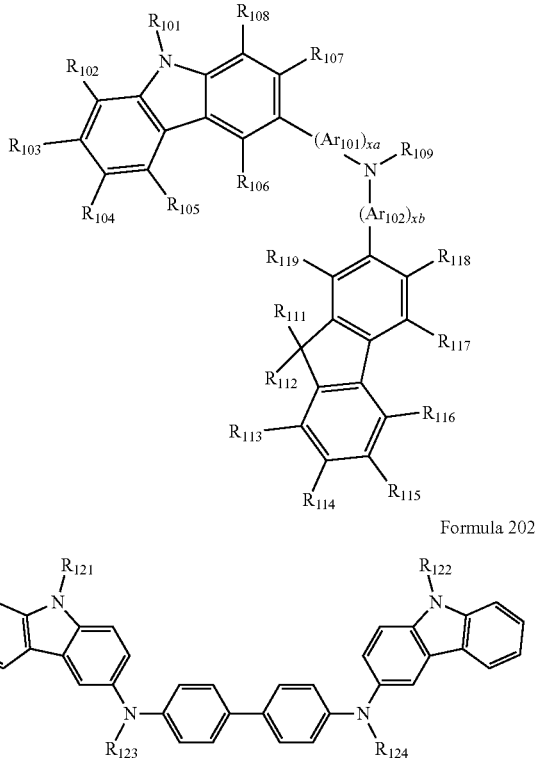

Formula 202

Ar$_{101}$ and Ar$_{102}$ in Formula 201 may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a C3-C10 heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ hetero aryl.

xa and xb in Formula 201 may be each independently an integer of 0 to 5, or 0, 1, or 2. xa and xb in Formula 201 may be each independently an integer of 0 to 5, or 0, 1, or 2. For example, xa may be 1 and xb may be 0, but are not limited thereto.

R$_{101}$ to R$_{108}$, R$_{111}$ to R$_{119}$, and R$_{121}$ to R$_{124}$ in Formulae 201 and 202 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl (for example, a methyl group, an ethyl group, a propyl group, a butyl group, a pentyl group, or a hexyl group), and a $C_1$-$C_{10}$ alkoxy (for example, a methoxy group, an ethoxy group, a propoxy group, a butoxy group, or a pentoxy group);

a $C_1$-$C_{10}$ alkyl and a $C_1$-$C_{10}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof and a phosphoric acid or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, and a $C_1$-$C_{10}$ alkoxy group, but they are not limited thereto.

R$_{109}$ in Formula 201 may be a group selected from a phenyl group, a naphthyl group, an anthracenyl group, a biphenyl group, and pyridinyl group, each substituted with at least one group selected from phenyl group, a naphthyl group, an anthracenyl group, a biphenyl group, and a pyridinyl group; and a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{29}$ alkoxy.

According to an embodiment, the compound represented by Formula 201 may be represented by Formula 201A below, but is not limited thereto:

Formula 201A

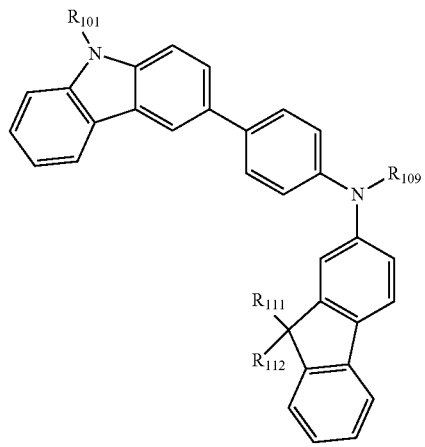

R$_{101}$, R$_{111}$, R$_{112}$, and R$_{109}$ in Formula 201A may be understood by referring to the description provided herein.

For example, the compound represented by Formula 201, and the compound represented by Formula 202 may include compounds HT1 to HT20 illustrated below, but are not limited thereto.

HT1
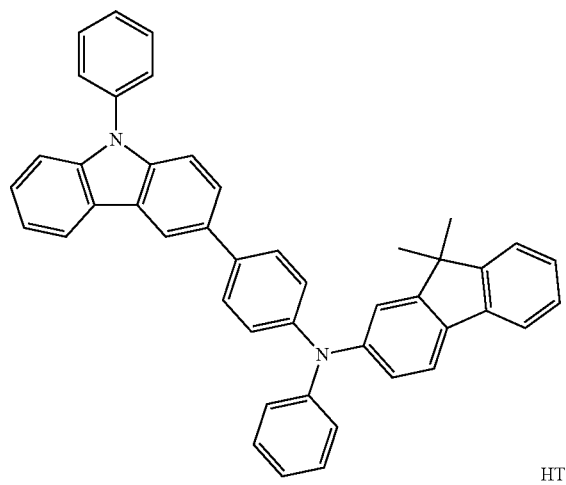
HT2
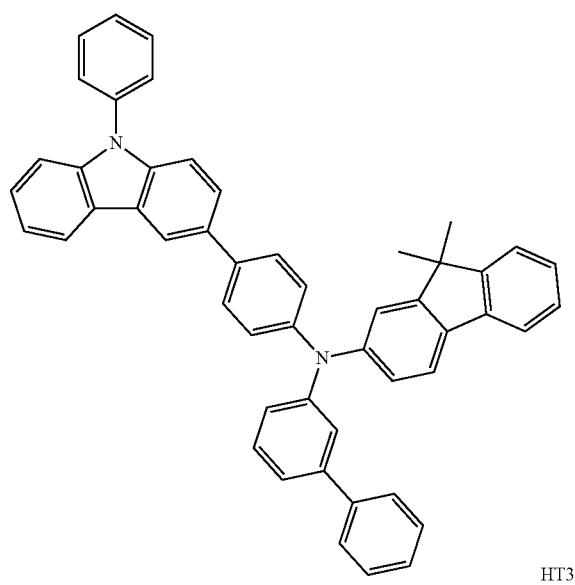
HT3
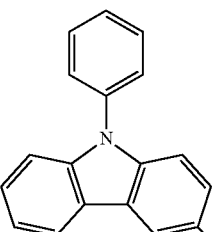
HT4
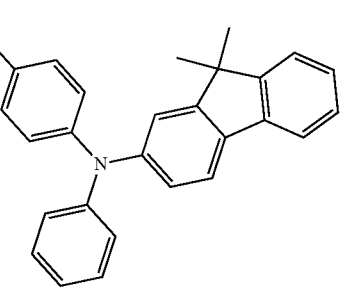
HT5
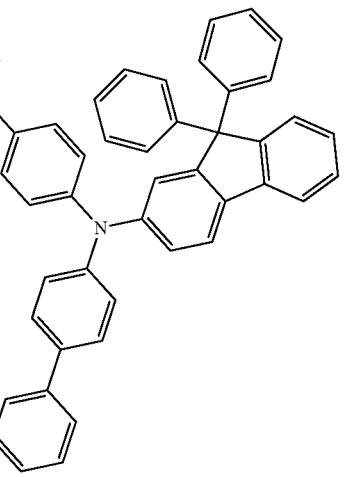

HT6
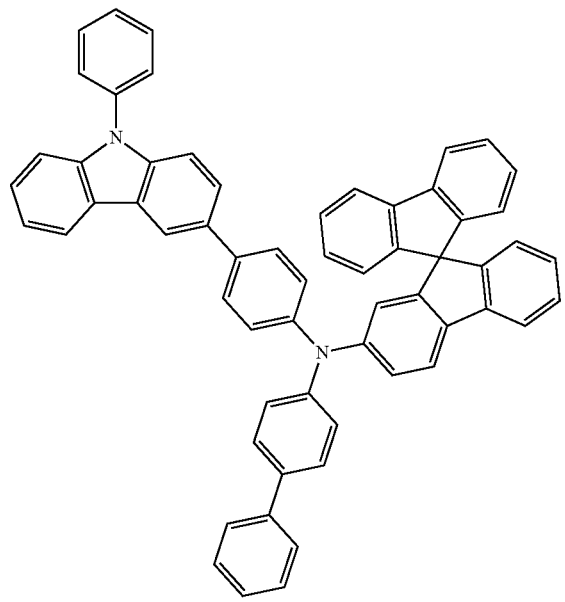
HT7
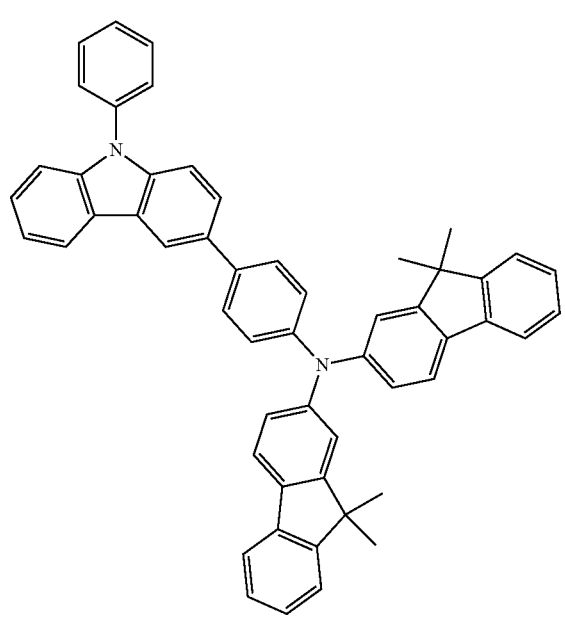
HT8
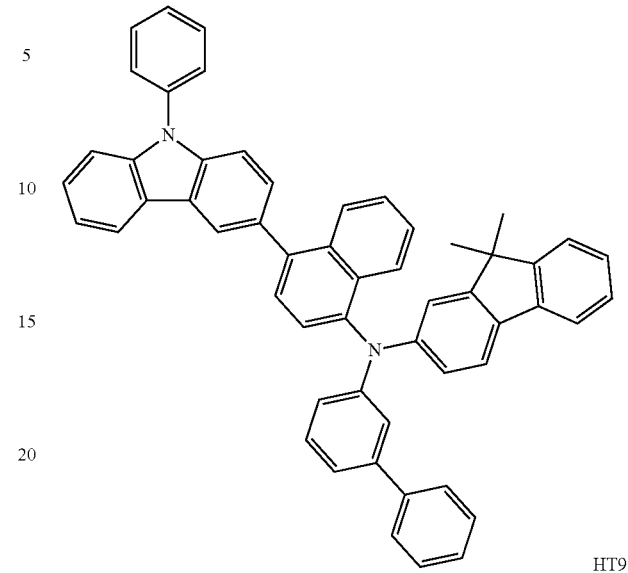
HT9
HT10
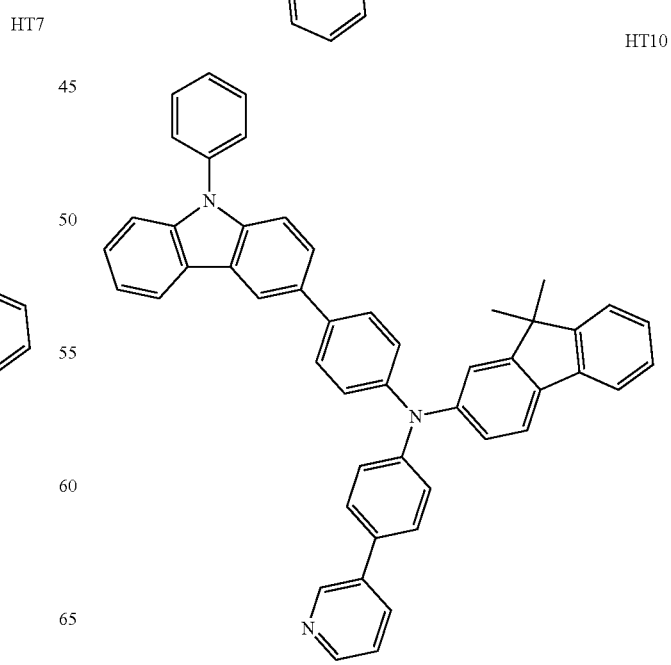

HT11
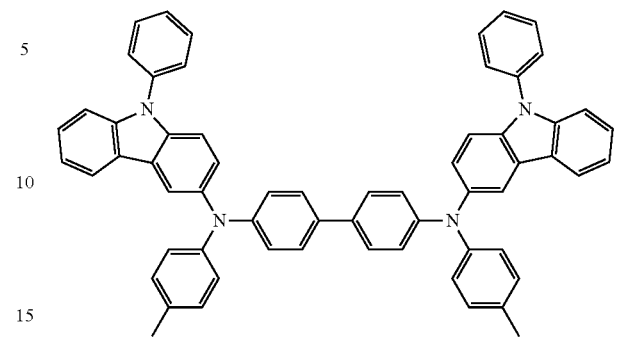
HT14
HT15
HT12
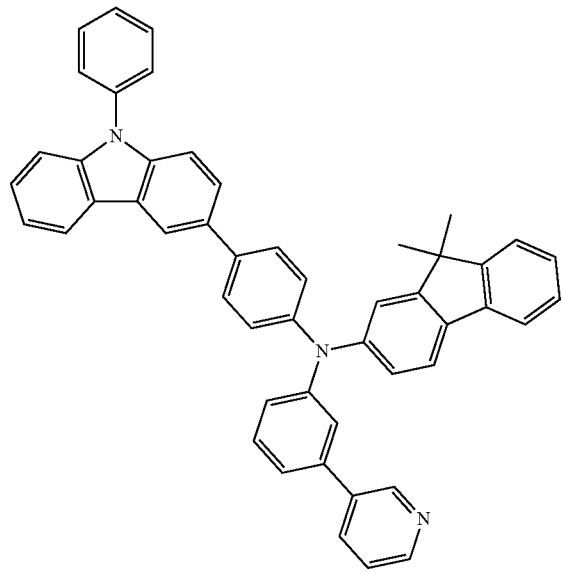
HT16
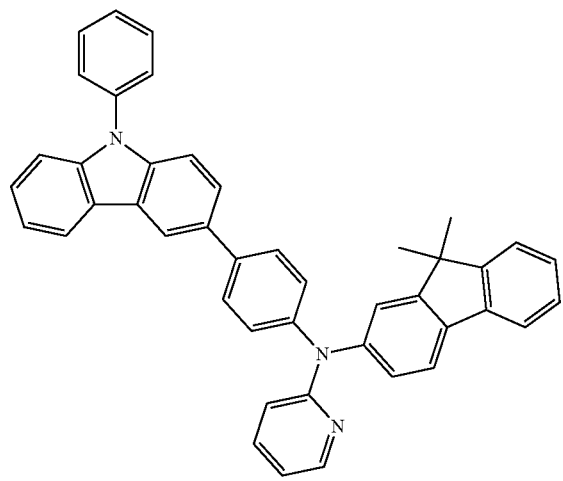
HT13
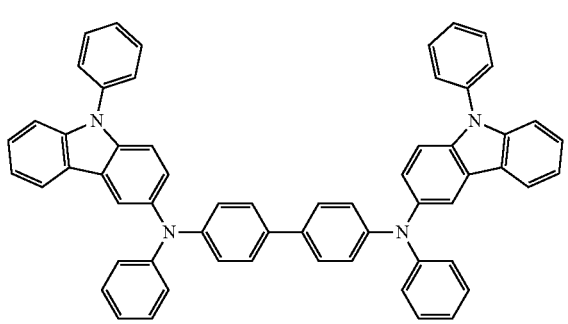
HT17
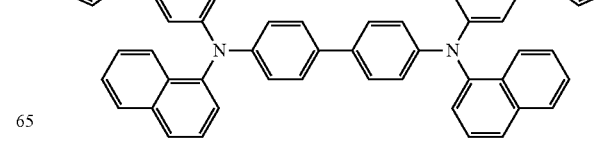

-continued

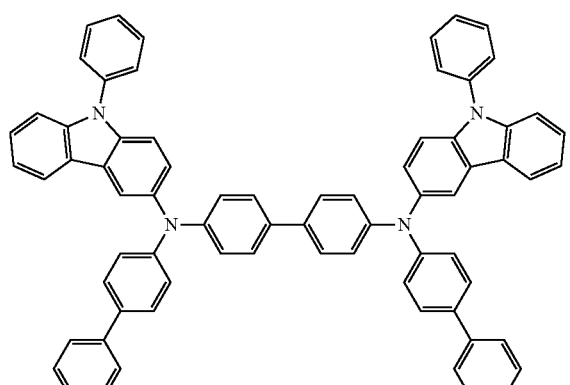
HT18

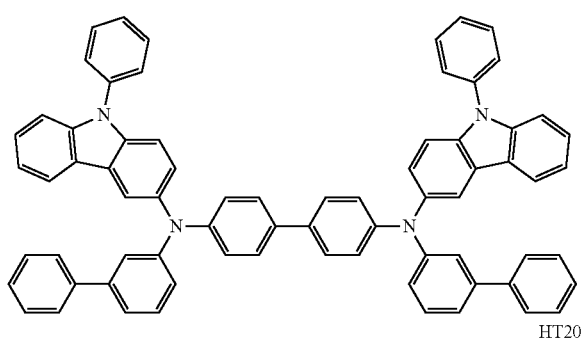
HT19

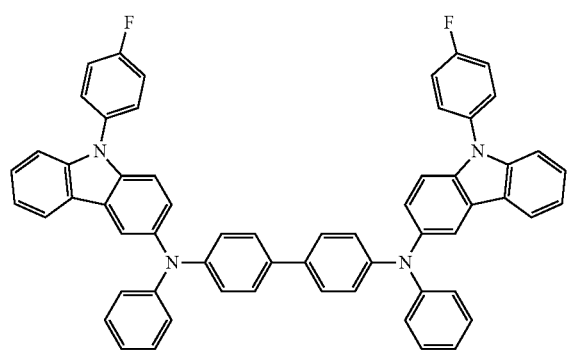
HT20

A thickness of the hole transport region may be in a range of about 100 Angstrom (Å) to about 10,000 Å, for example, about 100 Å to about 1,000 Å. When the hole transport region includes both a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one of a quinone derivative, a metal oxide, and a cyano group-containing compound, but is not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-CTNQ); a metal oxide, such as tungsten oxide or molybdenium oxide; and a cyano group-containing compound, such as Compound HT-D1 below, but are not limited thereto.

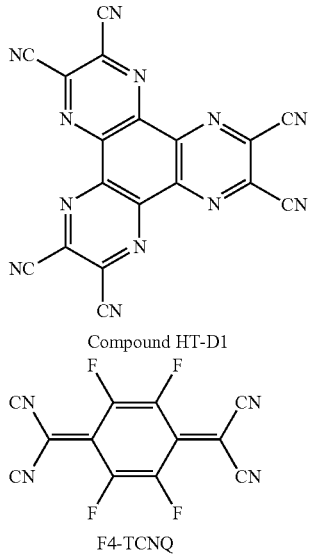

Compound HT-D1

F4-TCNQ

The hole transport region may include a buffer layer.

Also, the buffer layer may compensate for an optical resonance distance according to a wavelength of light emitted from the emission layer, and thus, an efficiency of a formed organic light-emitting device may be improved.

Then, an emission layer may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

The emission layer may include a host and a dopant. The host may include at least one condensed-cyclic compound represented by Formula 1.

The host may further include, in addition to the condensed-cyclic compound represented by Formula 1, at least one of TPBi, TBADN, AND (also referred to as "DNA"), CBP, CDBP, and TCP.

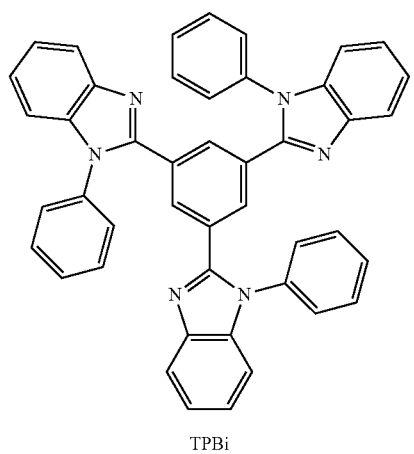
TPBi

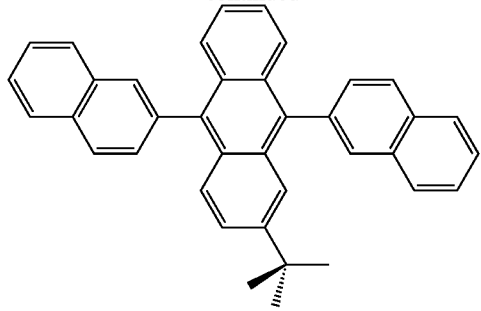

TBADN

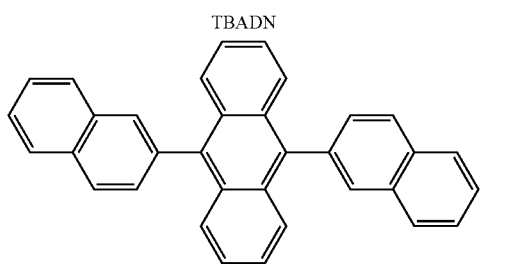

ADN

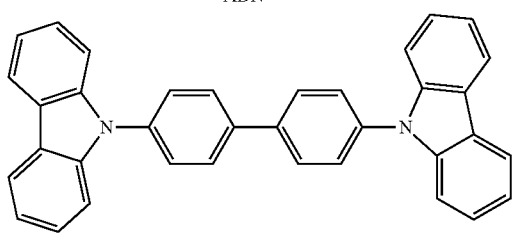

CBP

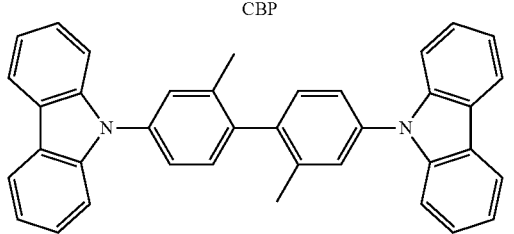

CDBP

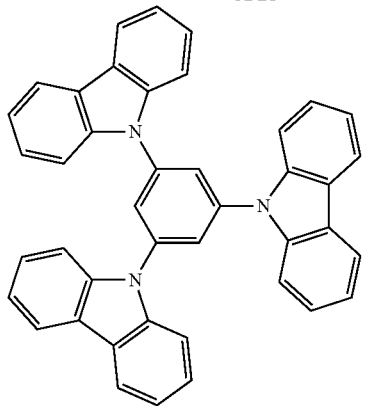

TCP

According to another embodiment, the host may further include, in addition to the condensed-cyclic compound represented by Formula 1, a compound represented by Formula 301 below:

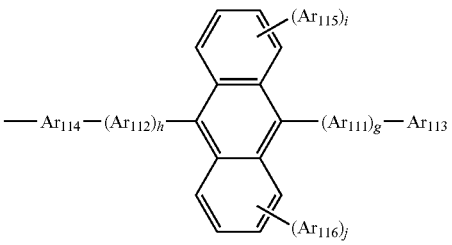

Formula 301

$Ar_{111}$ and $Ar_{112}$ in Formula 301 may be each independently selected from a phenylene group, a naphthylene group, a phenanthrenylene group, and a pyrenylene group; and a phenylene group, a naphthylene group, a phenanthrenylene group, a fluorenyl group, and a pyrenylene group, each substituted with at least one group selected from a phenyl group, a naphthyl group, and an anthracenyl group.

$Ar_{113}$ to $Ar_{116}$ in Formula 301 may be each independently selected from a C1-C10 alkyl; a phenyl group, a naphthyl group, a phenanthrenyl group, and a pyrenyl group; and a phenyl group, a naphthyl group, a phenanthrenyl group, a fluorenyl group, and a pyrenyl group, each substituted with at least one group selected from a phenyl group, a naphthyl group, and an anthracenyl group.

g, h, I, and j in Formula 301 may be each independently an integer of 0 to 4, for example, an integer of 0, 1, or 2.

$Ar_{113}$ and $Ar_{116}$ in Formula 301 may be each independently selected from a $C_1$-$C_{10}$ alkyl substituted with at least one group selected from a phenyl group, a naphthyl group, and an anthracenyl group;

a phenyl group, a naphthyl group, an anthracenyl group, a pyrenyl group, a phenanthrenyl group, and a fluorenyl group; and a phenyl group, a naphthyl group, an anthracenyl group, a pyrenyl group, a phenanthrenyl group, and a fluorenyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group, and

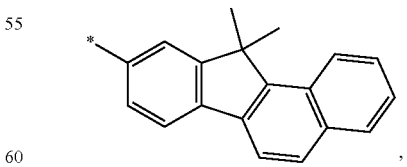

, but are not limited thereto.

According to another embodiment, the host may further include, in addition to the condensed-cyclic compound represented by Formula 1, a compound represented by Formula 302 below:

Formula 302

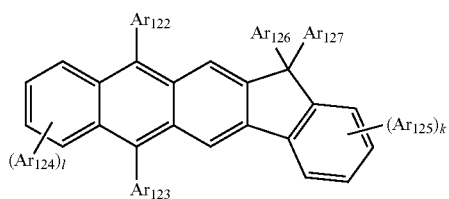

Ar$_{122}$ to Ar$_{125}$ in Formula 302 are the same as described in detail in connection with Ar$_{113}$ in Formula 301.

Ar$_{126}$ and Ar$_{127}$ in Formula 302 may each be independently a C$_1$-C$_{10}$ alkyl group (for example, a methyl group, an ethyl group, or a propyl group).

k and l in Formula 302 may be each independently an integer of 0 to 4. For example, k and l may each be 0, 1, or 2.

The compound represented by Formula 301, and the compound represented by Formula 302 may include Compounds H1 to H42 illustrated below, but are not limited thereto.

H1

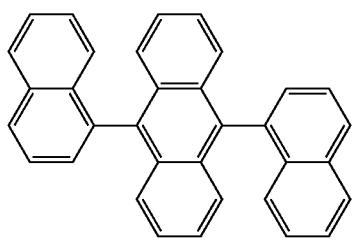

H2

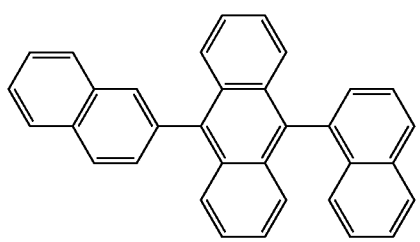

H3

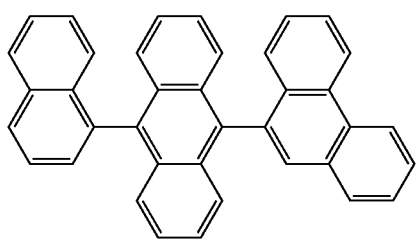

H4

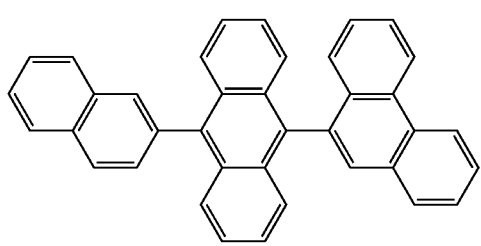

H5

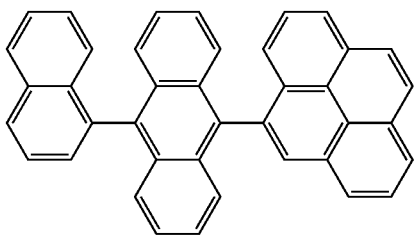

H6

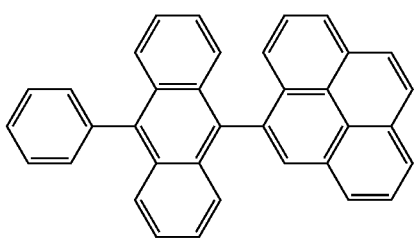

H7

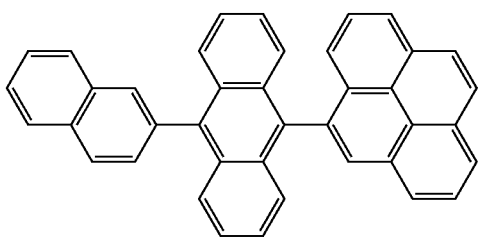

H8

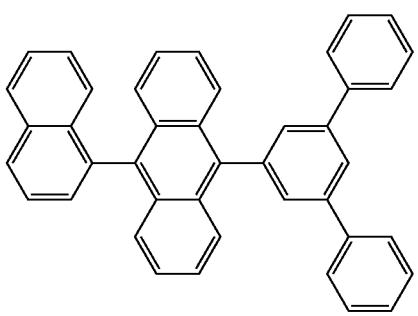

H9

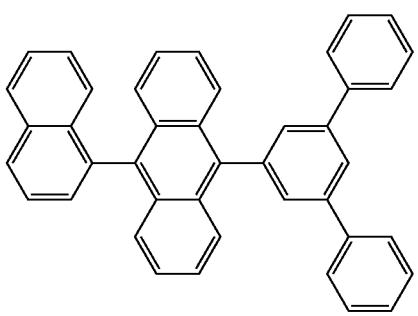

H10

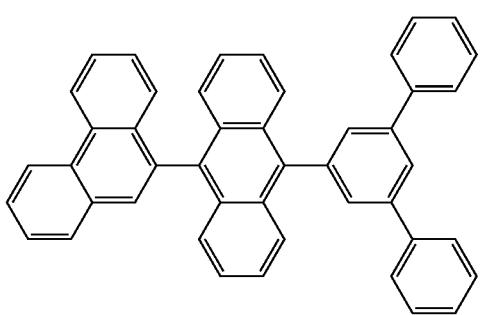

H11
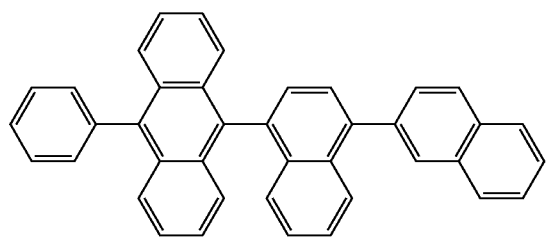
H12
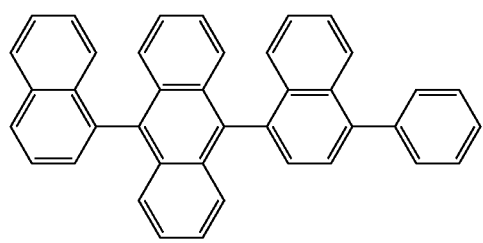
H13
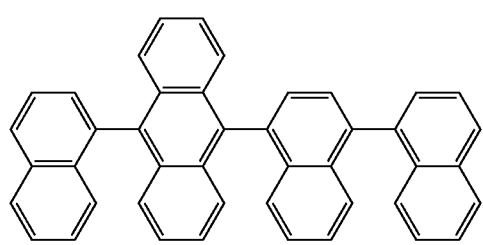
H14
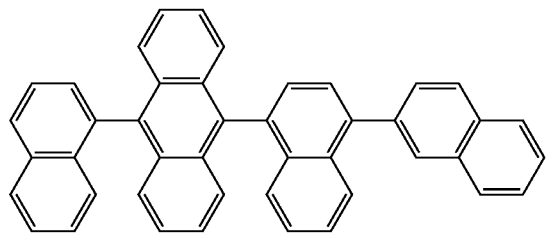
H15
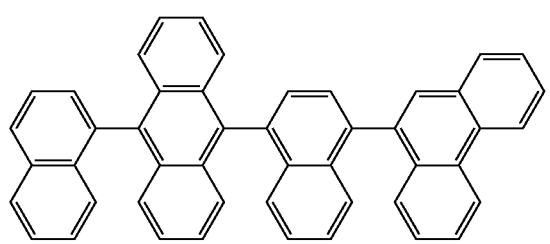
H16
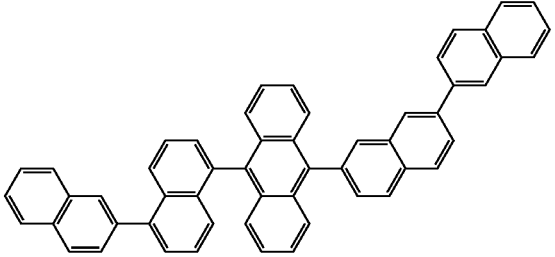
H17
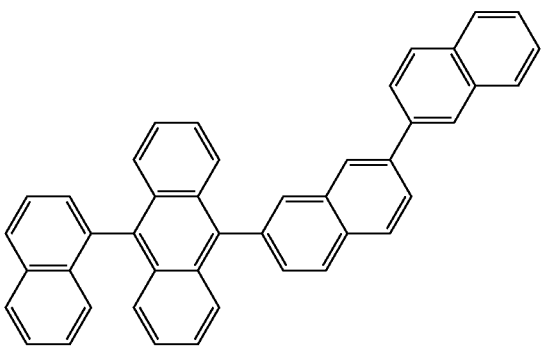
H18
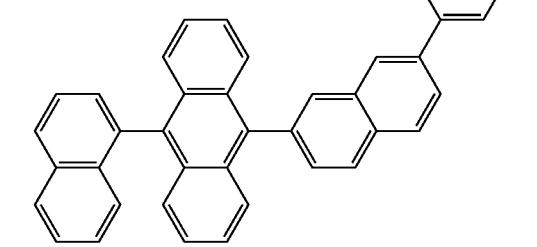
H19
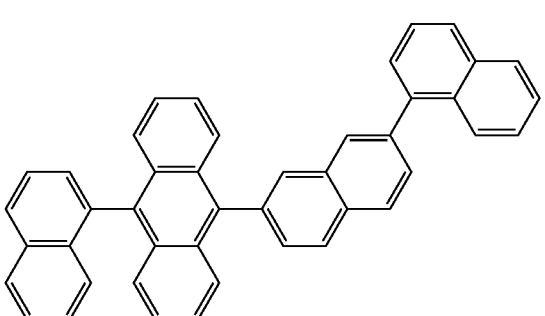
H20
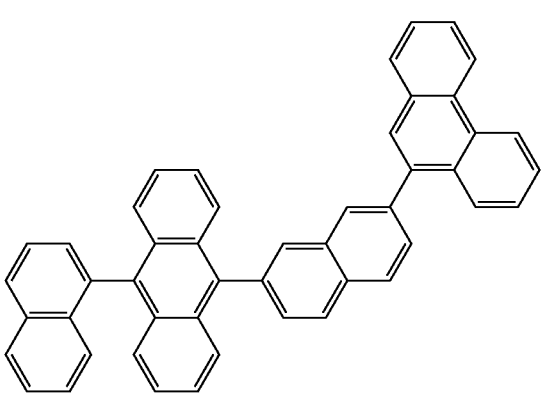

H21
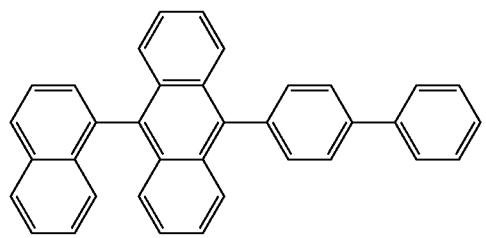
H22
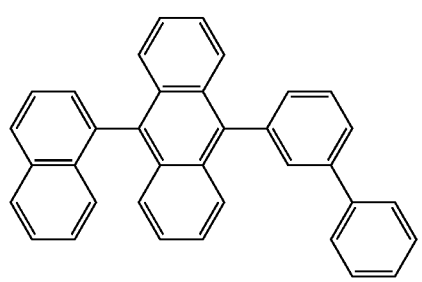
H23
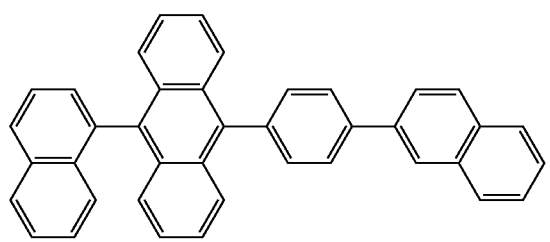
H24
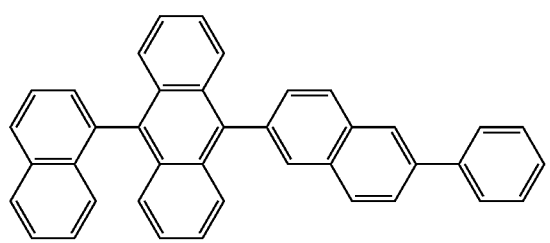
H25
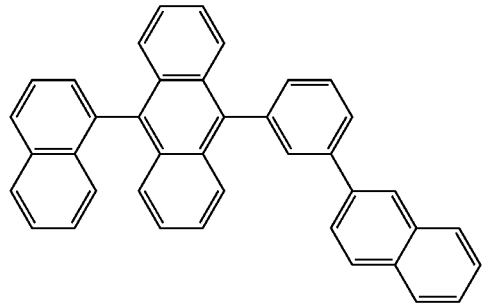
H26
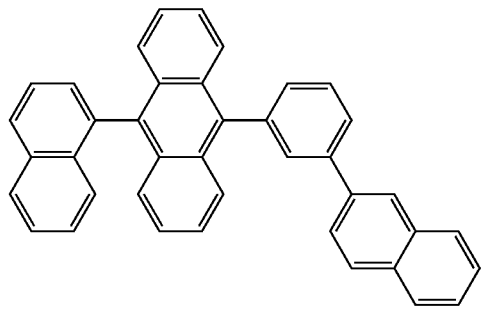
H27
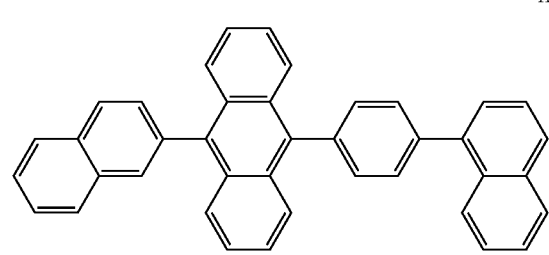
H28
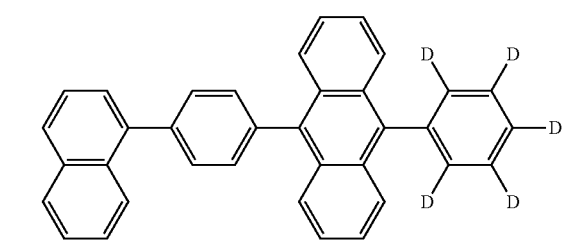
H29
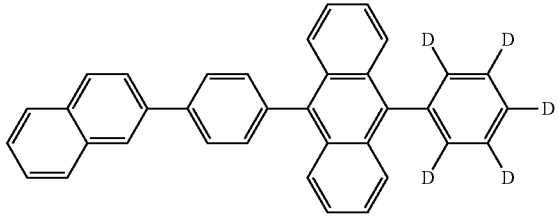
H30
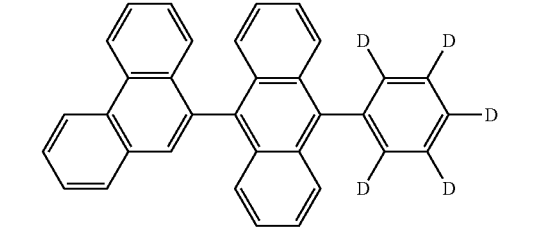
H31
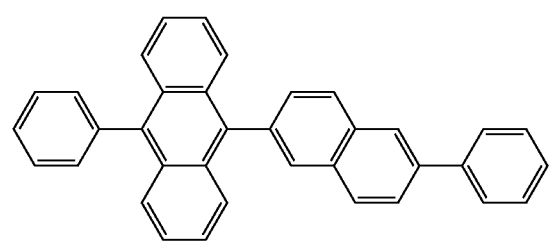

101
-continued
H32
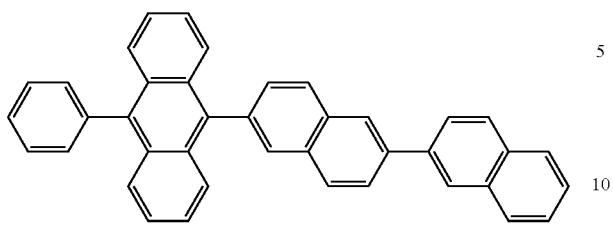
H33
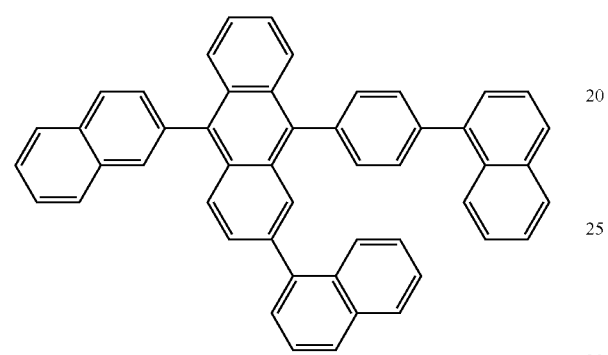
H34
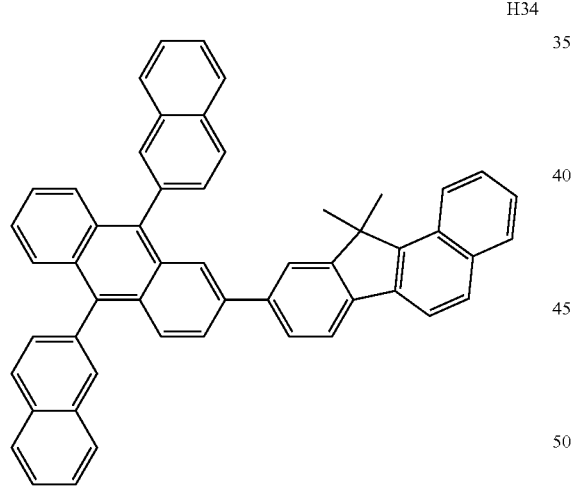
H35
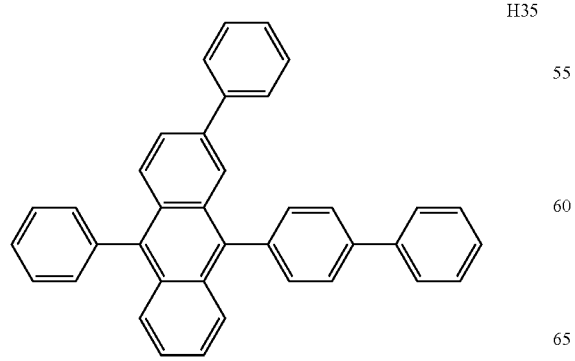
102
-continued
H36
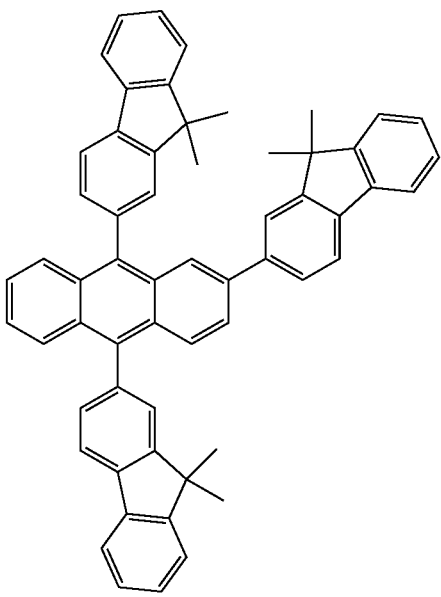
H37
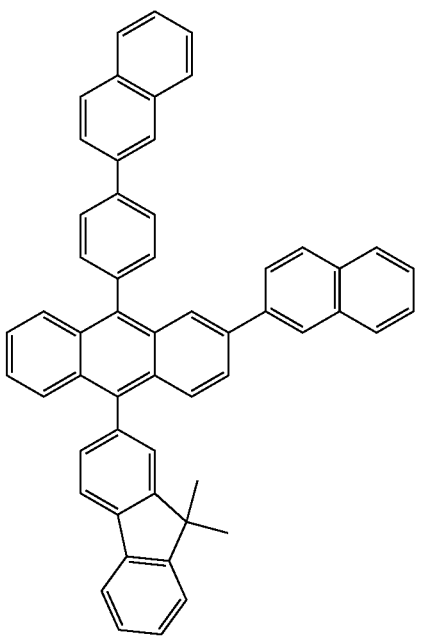
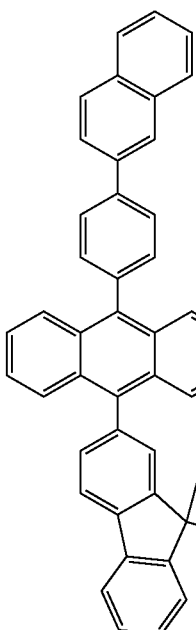
H38

H39
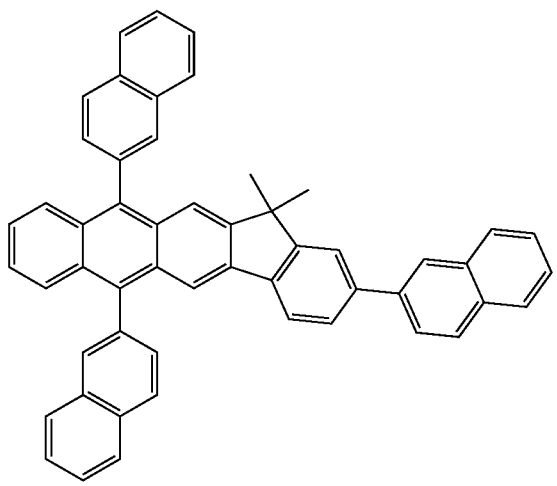
H40
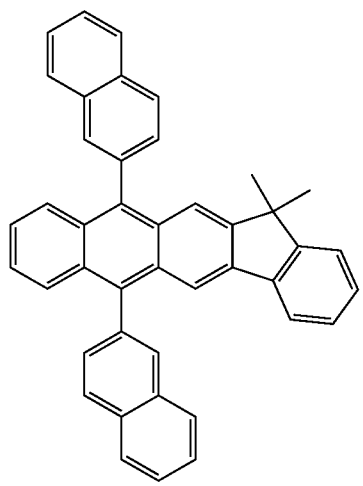
H41
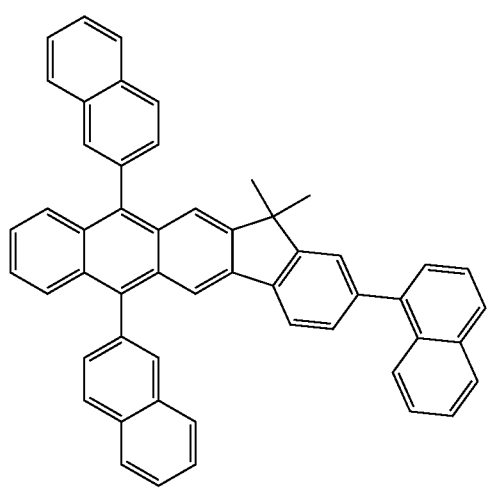
H42
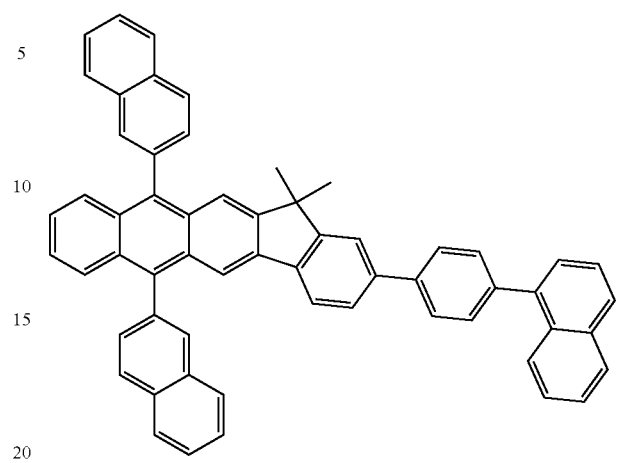
According to another embodiment, the host may include, in addition to the condensed-cyclic compound represented by Formula 1, at least one of Compounds H43 to H49 below, but are not limited thereto:
H43
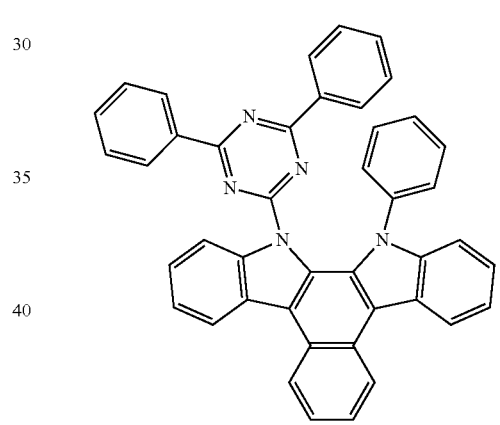
H44
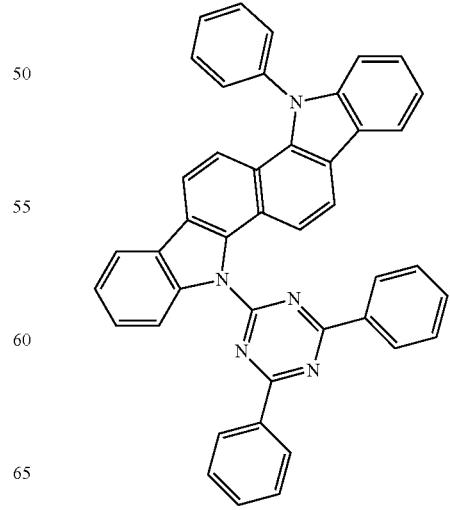

H45

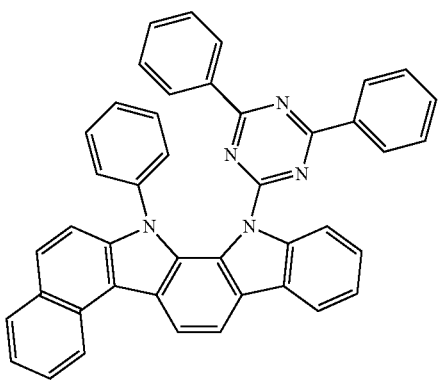

H46

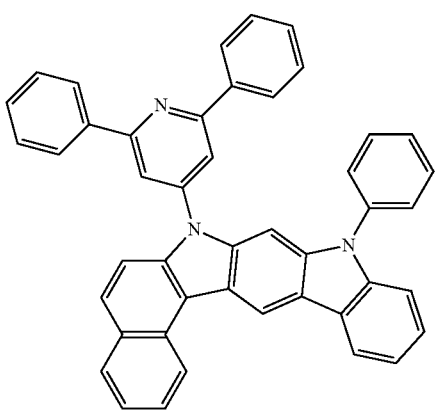

H47

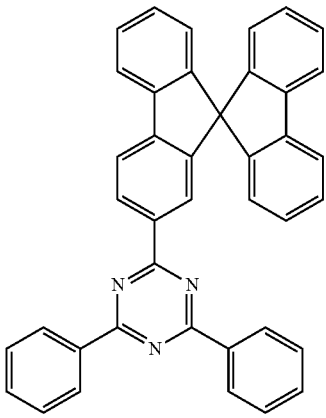

H48

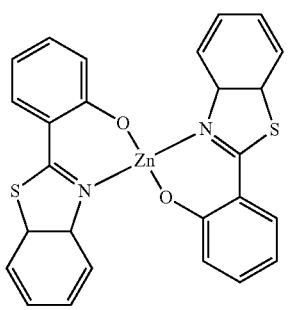

H49

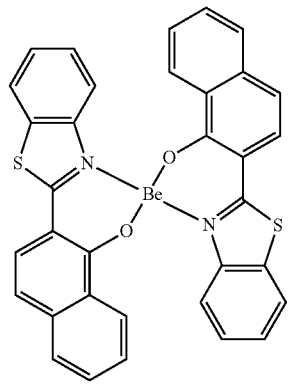

When the organic light-emitting device is a full color organic light-emitting device, the emission layer may be patterned into a red emission layer, a green emission layer, and a blue emission layer. According to another embodiment, due to a stack structure including a red emission layer, a green emission layer, and/or a blue emission layer, the emission layer may emit white light. A host in the red emission layer, the green emission layer, and the blue emission layer may include the condensed-cyclic compound represented by Formula 1. According to an embodiment, the host in the green emission layer may include the condensed-cyclic compound represented by Formula 1.

A dopant in the emission layer may be a fluorescent dopant that emits light according to a fluorescent emission mechanism or a phosphorescent dopant that emits light according to a phosphorescent emission mechanism.

According to an embodiment, the emission layer may include a host including the condensed-cyclic compound represented by Formula 1 and a phosphorescent dopant. The phosphorescent dopant may include an organometallic complex including a transition metal (for example, iridium (Ir), platinum (Pt), osmium (Os), or rhodium (Rh)).

The phosphorescent dopant may include at least one of Compounds PD1 to PD74 below, but is not limited thereto:

PD1

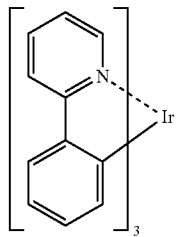

PD2

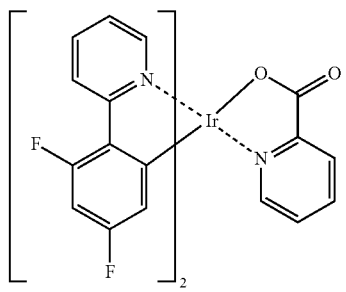

-continued
PD3
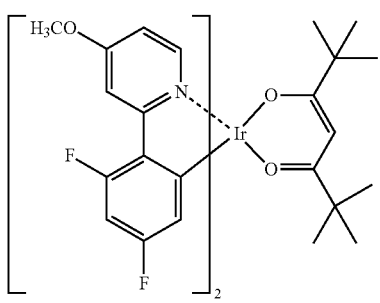
PD4
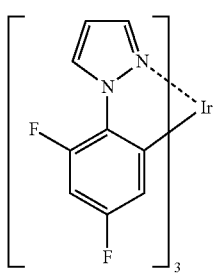
PD5
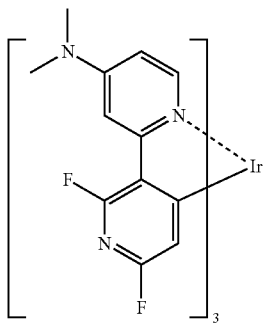
PD6
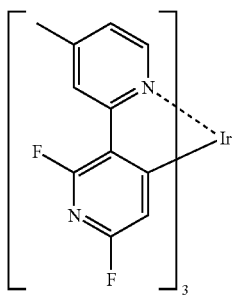
PD7
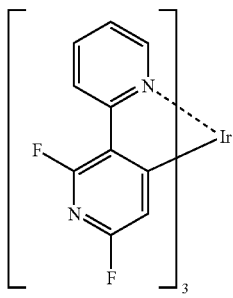
-continued
PD8
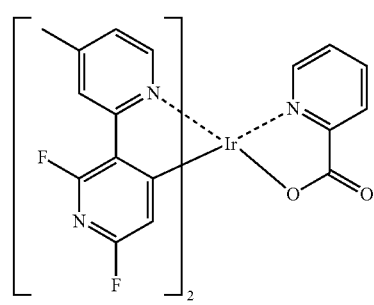
PD9
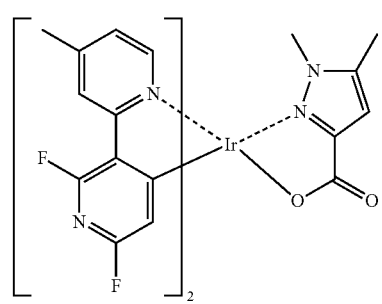
PD10
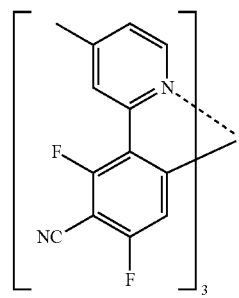
PD11
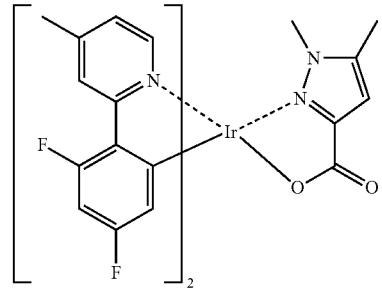
PD12
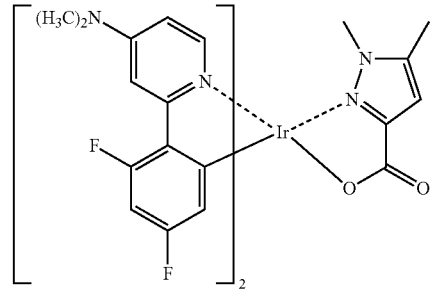

PD13 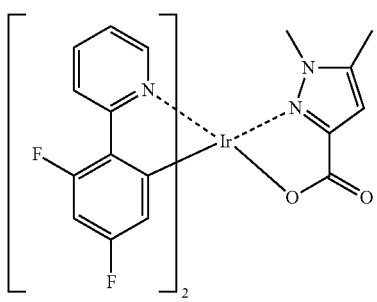
PD14 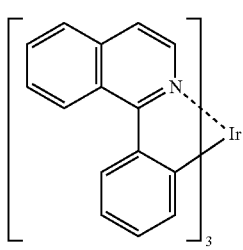
PD15 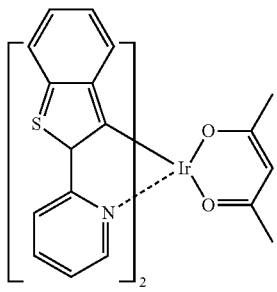
PD16 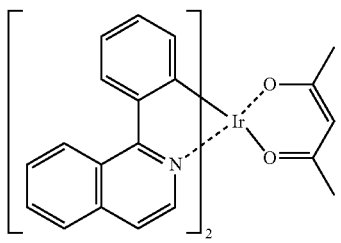
PD17 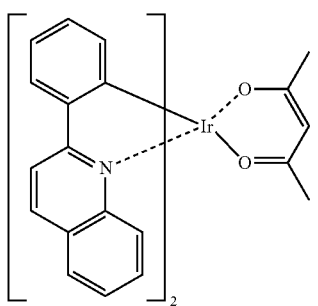
PD18 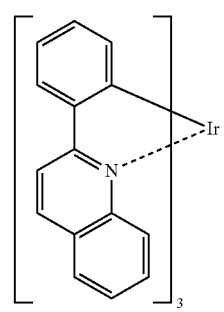
PD19 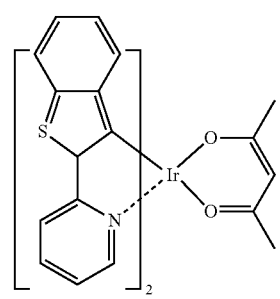
PD20 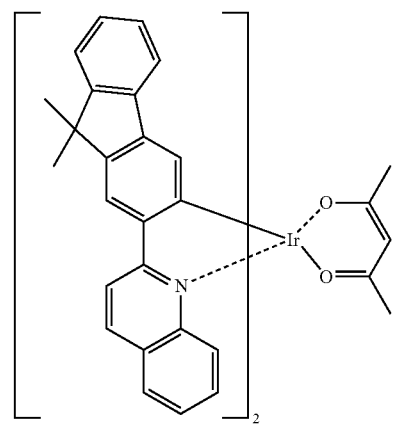
PD21 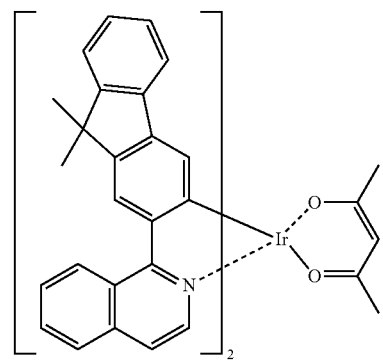
PD22 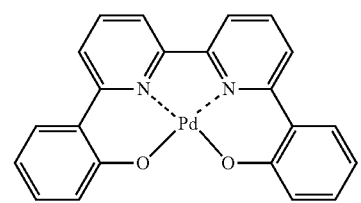

PD23 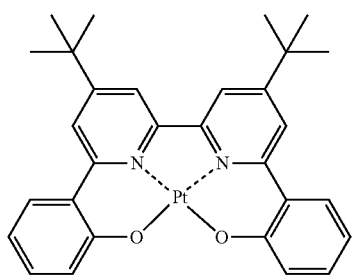
PD24 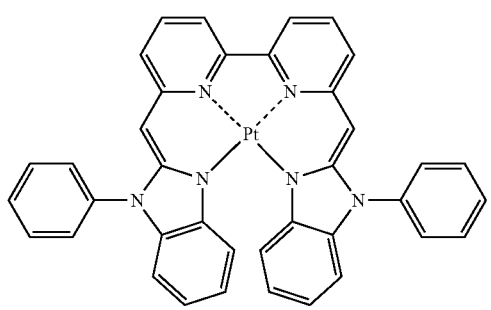
PD25 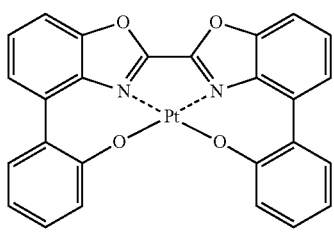
PD26 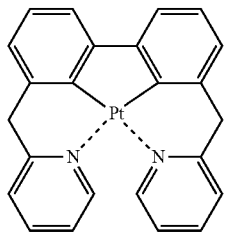
PD27 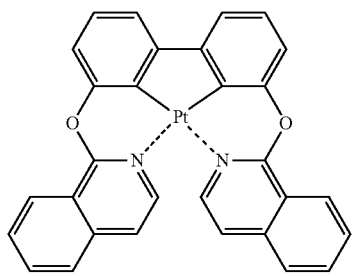
PD28 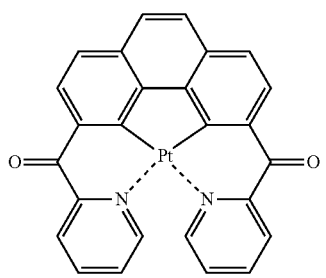
PD29 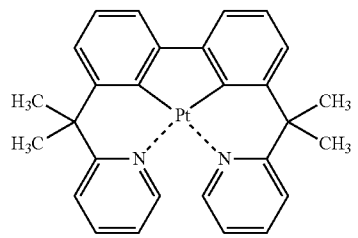
PD30 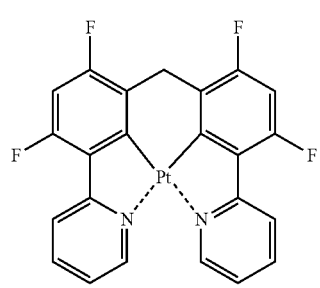
PD31 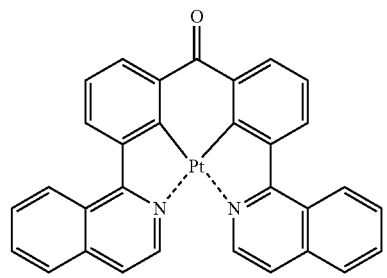
PD32 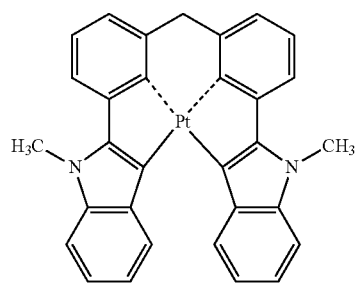
PD33 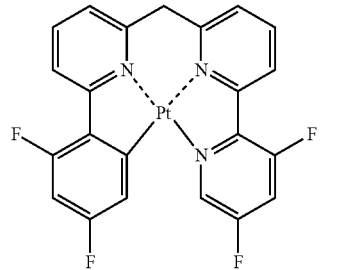
PD34 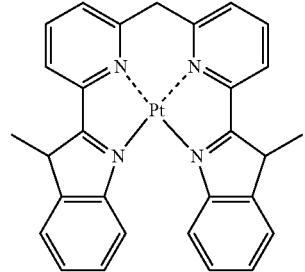

-continued
PD35
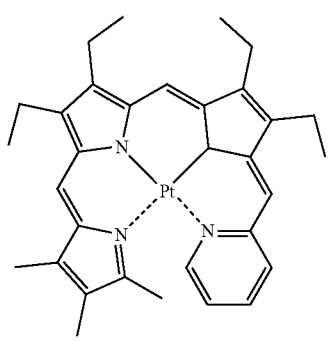
PD36
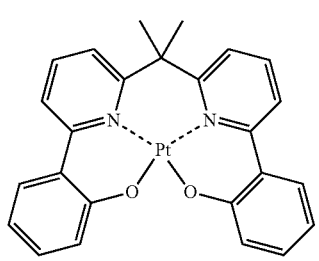
PD37
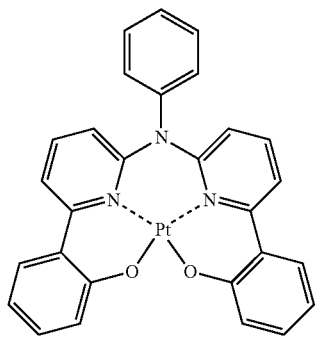
PD38
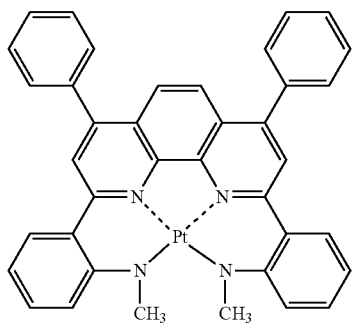
PD39
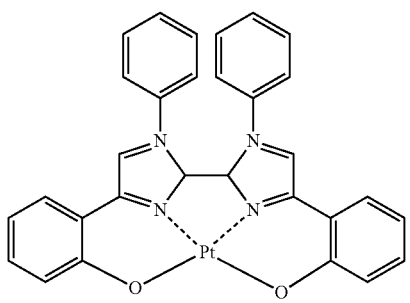
-continued
PD40
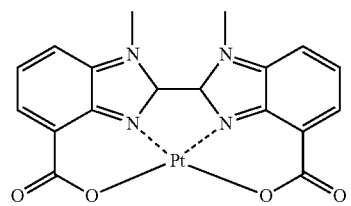
PD41
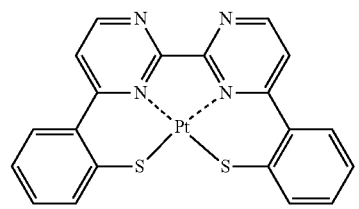
PD42
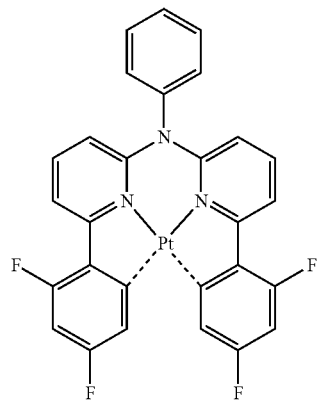
PD43
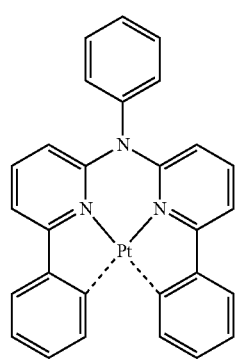
PD44
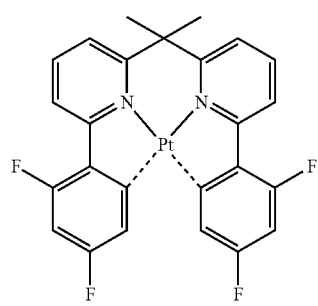

PD45 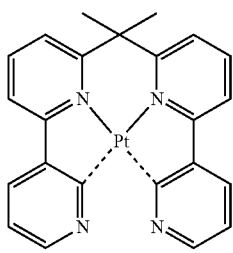
PD46 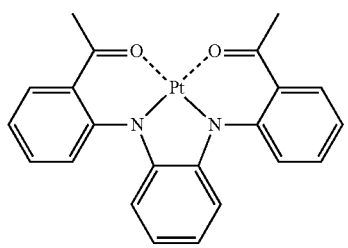
PD47 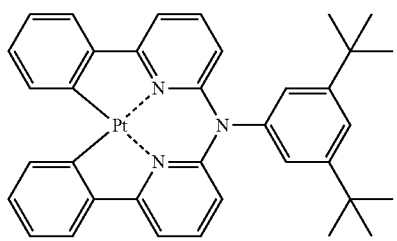
PD48 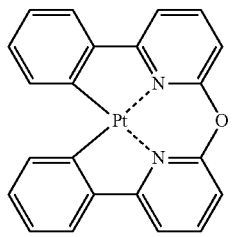
PD49 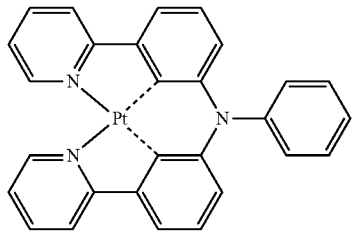
PD50 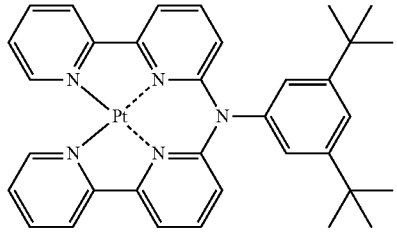
PD51 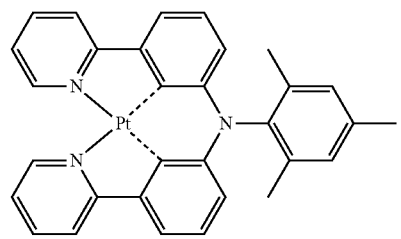
PD52 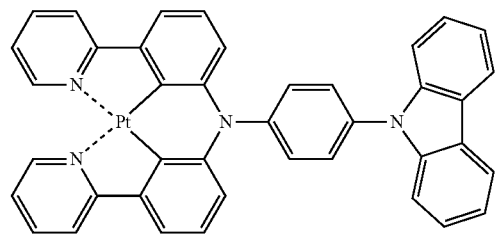
PD53 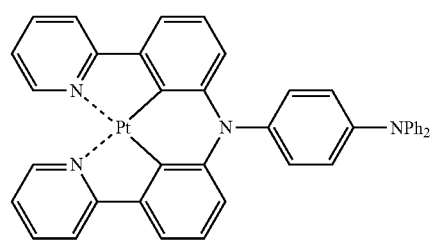
PD54 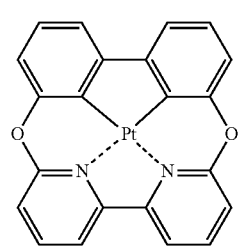
PD55 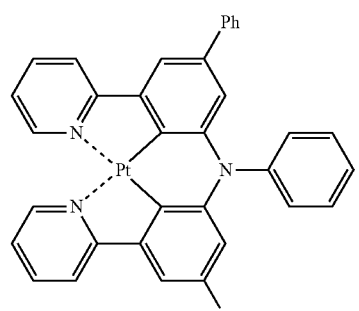
PD56 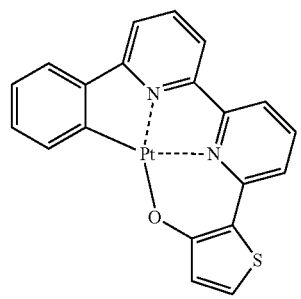

-continued
PD57
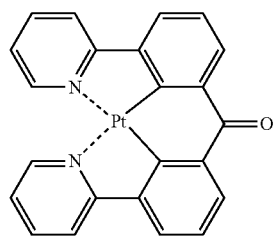
PD62
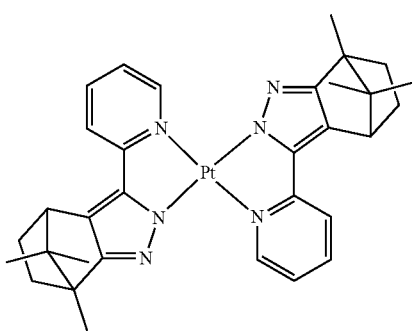
PD58
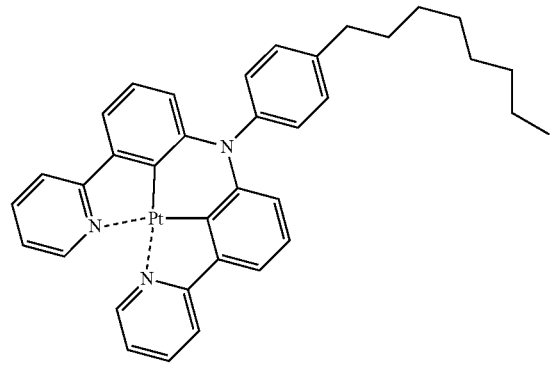
PD63
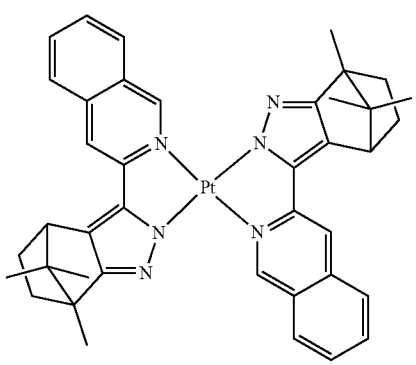
PD59
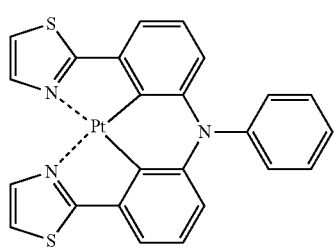
PD64
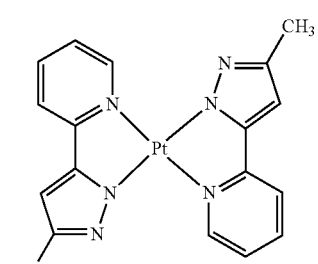
PD60
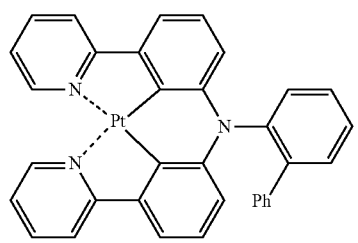
PD65
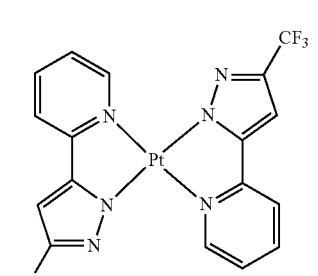
PD61
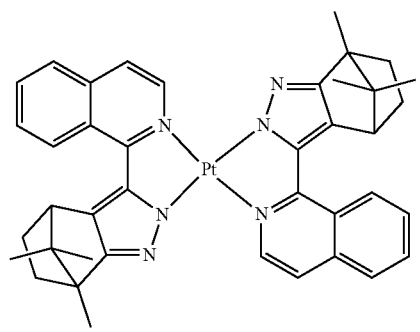
PD66
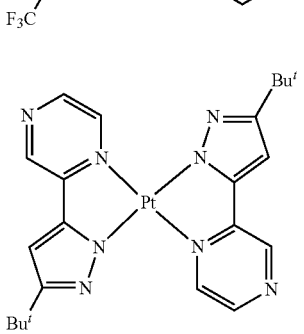

PD67 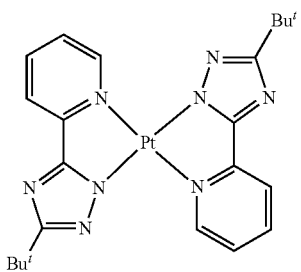
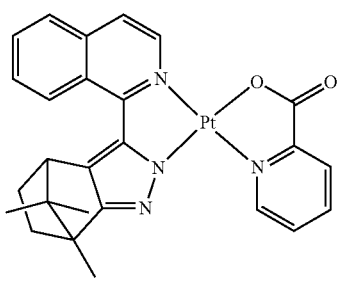
PD68 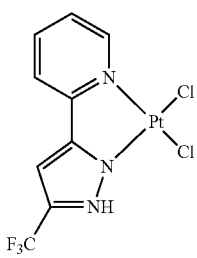
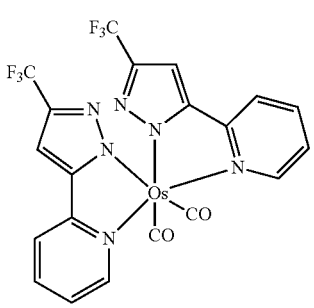
PD69
PD70 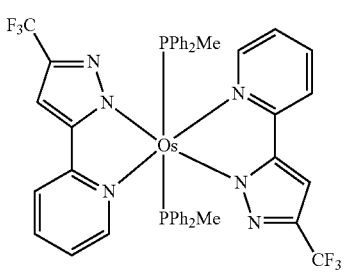
PD72 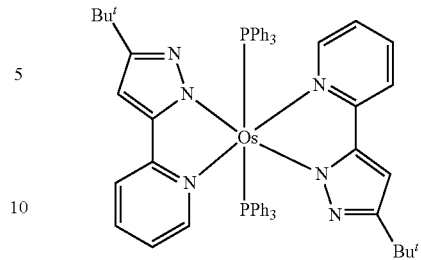
PD73 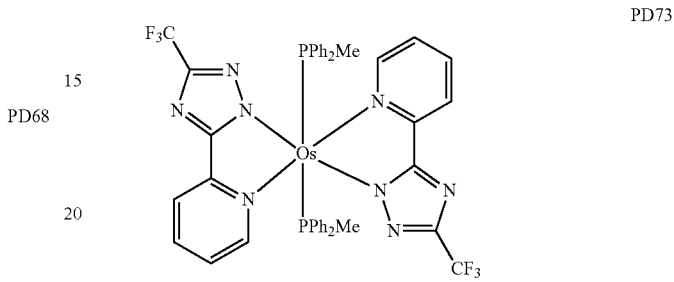
PD74 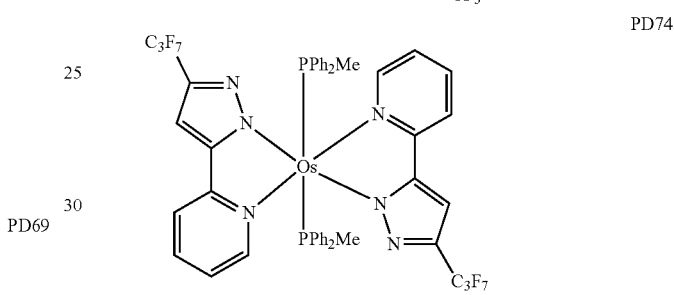
According to another embodiment, the phosphorescent dopant may include PtOEP or Compound PhGD illustrated below:
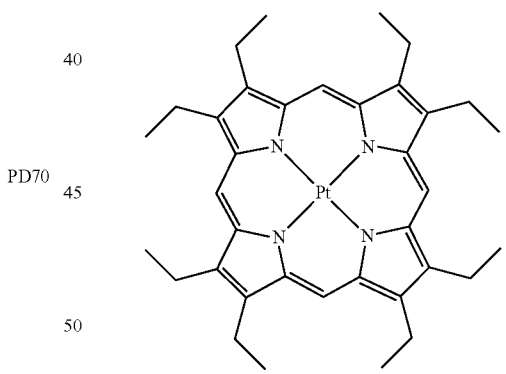
PtOEP
PD71 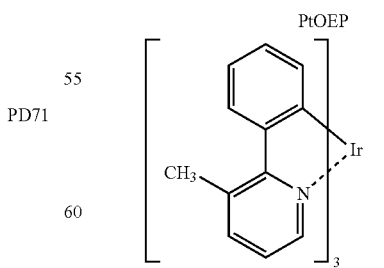
PhGD
The fluorescent dopant may include at least one compound selected from DPAVBi, BDAVBi, TBPe, DCM, DCJTB, Coumarin 6, and C545T.

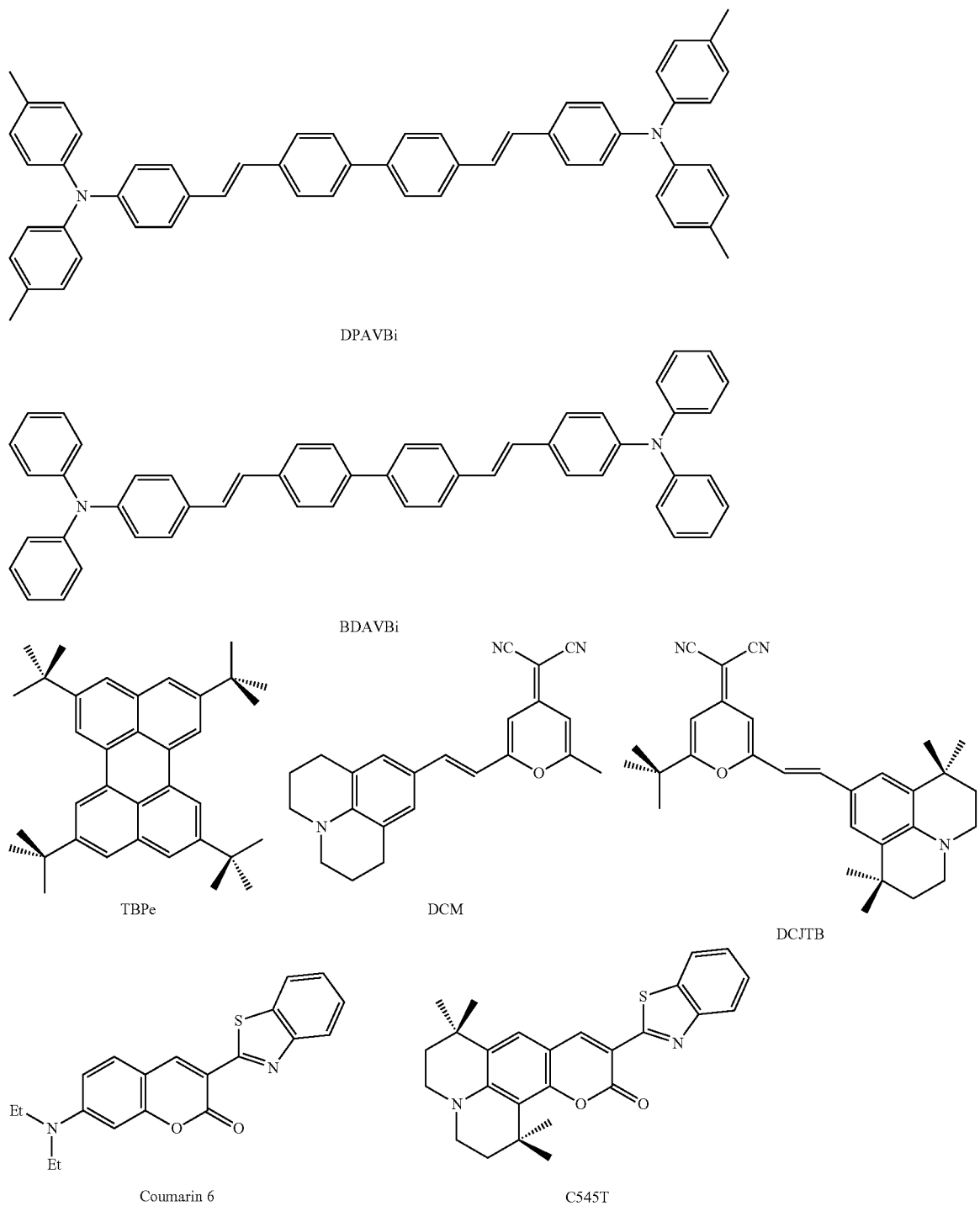

When the emission layer includes a host and a dopant, an amount of the dopant may be from about 0.01 to about 15 parts by weight based on about 100 parts by weight of the host. However, the amount of the dopant is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one region selected from a hole blocking layer, an electron transport layer, and an electron injection layer.

For example, the electron transport region may have a structure of electron transport layer, hole blocking layer/electron transport layer/electron injection layer, or electron transport layer/electron injection layer, but is not limited thereto. The electron transport layer may have a single-layered structure or a multi-layer structure including two or more different materials.

Conditions for forming the hole blocking layer, the electron transport layer, and the electron injection layer of the electron transport region may be understood by referring to the conditions for forming the hole injection layer.

When the electron transport layer includes a hole blocking layer, the hole blocking layer may include, for example, at least one of BCP and Bphen, but is not limited thereto.

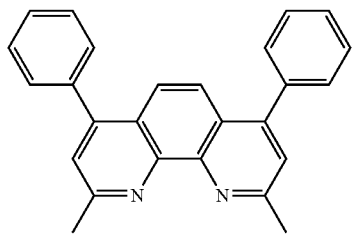

BCP

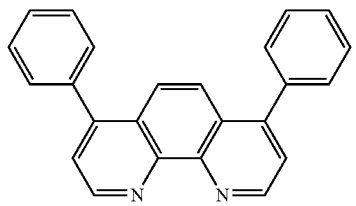

Bphen

A thickness of the hole blocking layer may be in a range of about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may further include, in addition to the condensed-cyclic compound represented by Formula 1, at least one compound selected from BCP, Bphen, and Alq$_3$, Balq, TAZ, and NTAZ.

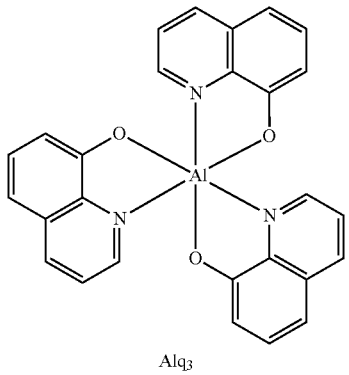

Alq$_3$

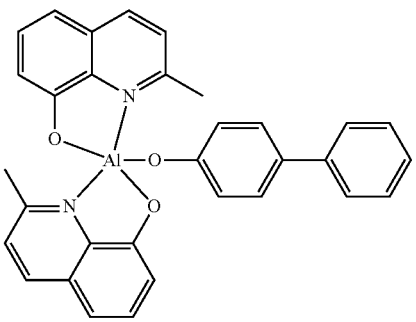

BAlq

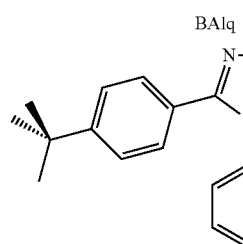

TAZ

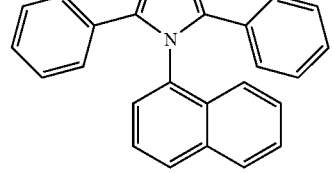

NTAZ

According to another embodiment, the electron transport layer may include at least one of ET1 and ET2, but is not limited thereto:

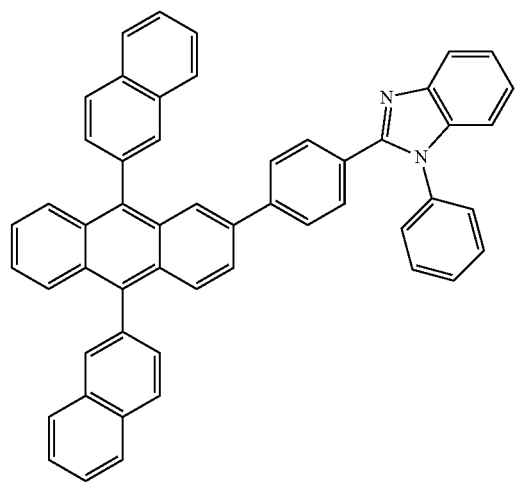

ET1

ET2

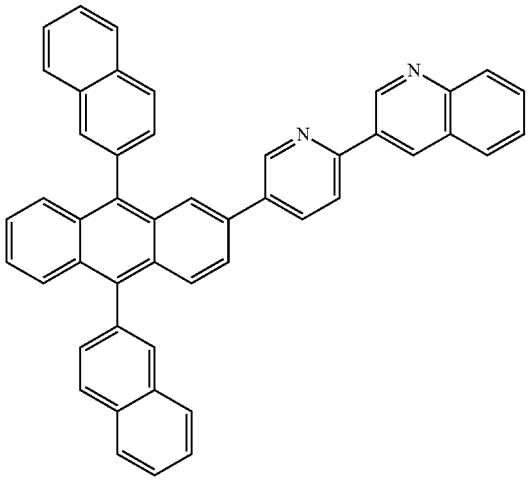

A thickness of the electron transport layer may be in a range of about 100 Å to about 1,000 Å, for example, about 150 Å to about 500 Å. When the thickness of the electron transport layer is within the range described above, the electron transport layer may have satisfactory electron transportation characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

ET-D1

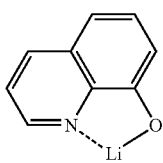

ET-D2

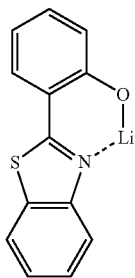

The electron transport region may include an electron injection layer that allows electrons to be easily provided from the second electrode 19.

The electron injection layer may include at least one compound selected from LiF, NaCl, CsF, $Li_2O$, and BaO.

A thickness of the electron injection layer may be in a range of about 1 Å to about 100 Å, for example, about 3 Å to about 90 Å. When the thickness of the electron injection layer is within the range described above, the electron injection layer may have satisfactory electron transportation characteristics without a substantial increase in driving voltage.

The second electrode 19 is disposed on the organic layer 15. The second electrode 19 may be a cathode. A material for forming the second electrode 19 may be metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top emission type light-emitting device, a transmissive electrode formed using ITO or IZO may be used as the second electrode 19.

Hereinbefore, the organic light-emitting device has been described with reference to FIG. 1, but is not limited thereto.

A $C_1$-$C_{60}$ alkyl group as used herein refers to a linear or branched aliphatic hydrocarbon monovalent group having 1 to 60 carbon atoms. Detailed examples thereof are methyl group, an ethyl group, a propyl group, an isobutyl group, a sec-butyl group, a tert-butyl group, a pentyl group, an iso-amyl group, and a hexyl group. A $C_1$-$C_{60}$ alkylene as used herein refers to a divalent group having the same structure as the $C_1$-$C_{60}$ alkyl.

A $C_1$-$C_{60}$ alkoxy group as used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group as used herein refers to a hydrocarbon group formed by substituting at least one pair of adjacent hydrogen atoms with a carbon-carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene as used herein refers to a divalent group having the same structure as the $C_2$-$C_{60}$ alkenyl.

A $C_2$-$C_{60}$ alkynyl group as used herein refers to a hydrocarbon group having at least one carbon-carbon triple bond in the middle or at the terminal of the $C_2$-$C_{60}$ alkyl group. Detailed examples thereof are an ethynyl group and a propynyl group. A $C_2$-$C_{60}$ alkynylene as used herein refers to a divalent group having the same structure as the $C_2$-$C_{60}$ alkynyl group.

A $C_3$-$C_{10}$ cycloalkyl group as used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene as used herein refers to a divalent group having the same structure as the $C_3$-$C_{10}$ cycloalkyl group.

A $C_3$-$C_{10}$ heterocycloalkyl group as used herein refers to a monovalent monocyclic group having at least one heteroatom selected from N, O, P, and S as a ring-forming atom and 3 to 10 carbon atoms. Detailed examples thereof are a tetrahydrofuranyl group and a tetrahydrothiophenyl group. A $C_3$-$C_{10}$ heterocycloalkylene group as used herein refers to a divalent group having the same structure as the $C_3$-$C_{10}$ heterocycloalkyl group.

A $C_3$-$C_{10}$ cycloalkenyl group as used herein refers to a monovalent non-aromatic monocyclic group that has 3 to 10 carbon atoms and at least one double bond in the ring thereof. Detailed examples thereof are a cyclopentenyl group, a cyclohexenyl group, and a cycloheptenyl group. A $C_3$-$C_{10}$ cycloalkenylene as used herein refers to a divalent group having the same structure as the $C_3$-$C_{10}$ cycloalkenyl group.

A $C_3$-$C_{10}$ heterocycloalkenyl group as used herein refers to a monovalent monocyclic group that has at least one heteroatom selected from N, O, P, and S as a ring-forming atom, 3 to 10 carbon atoms, and at least one double bond in its ring. Detailed examples of the $C_3$-$C_{10}$ heterocycloalkenyl group are a 2,3-dihydrofuranyl and a 2,3-dihydrothiophenyl group. A $C_3$-C10 heterocycloalkenylene group as used herein refers to a divalent group having the same structure as the $C_3$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene as used herein refers to a divalent group having a carbocyclic aromatic system having 6 to 60 carbon atoms. Detailed examples of the $C_6$-$C_{60}$ aryl are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other or connected to each other by a single bond.

A $C_2$-$C_{60}$ heteroaryl group as used herein refers to a monovalent group having a carbocyclic aromatic system that has at least one heteroatom selected from N, O, P, and S as a ring-forming atom, and 2 to 60 carbon atoms. A $C_2$-$C_{60}$ heteroarylene as used herein refers to a divalent group having a carbocyclic aromatic system that has at least one heteroatom selected from N, O, P, and S as a ring-forming atom, and 2 to 60 carbon atoms. Detailed examples of the $C_2$-$C_{60}$ heteroaryl are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other or connected to each other by a single bond.

The $C_6$-$C_{60}$ aryloxy group as used herein indicates —$OA_{102}$ (wherein $A_{102}$ is the $C_6$-$C_{60}$ aryl group), and the $C_6$-$C_{60}$ arylthio indicates —$SA_{103}$ (wherein $A_{103}$ is the $C_6$-$C_{60}$ aryl).

A monovalent non-aromatic condensed polycyclic group as used herein refers to a monovalent entirely non-aromatic group that has two or more rings condensed to each other, and only carbon atoms as a ring-forming atom. A detailed example of the monovalent non-aromatic condensed polycyclic group is a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group as used herein refers to a monovalent entirely non-aromatic group that has two or more rings condensed to each other, and a heteroatom selected from N, O P, and S, other than carbon atoms, as a ring-forming atom. A detailed example of the monovalent non-aromatic condensed heteropolycyclic group is a carbazolyl group. A divalent non-aromatic condensed heteropolycyclic group as used herein refers to a divalent group having the same structure as the monovalent non-aromatic condensed heteropolycyclic group.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that a molar equivalent of A was identical to a molar equivalent of B.

EXAMPLE

Synthesis Example 1

Synthesis of Compound 1

Synthesis of Intermediate A

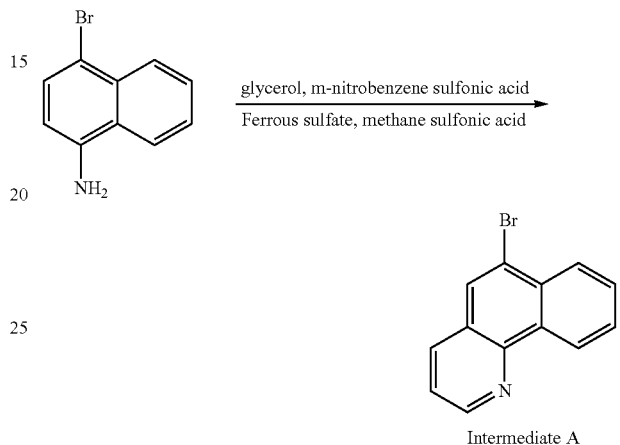

Intermediate A

In a 1 L round-bottomed flask, 75 g (337.72 mmol) of 1-amino-4-bromonaphthalene, 93.3 g (1013.15 mmol) of glycerol, 2.8 g (10.13 mmol) of ferrous sulfate, and 47.9 g (212.76 mmol) of m-nitrobenzene sulfonic acid were mixed with 200 ml of methane sulfonic acid, and then, the mixture was stirred at a temperature of 125 ° C. for 12 hours while heating. After the reaction stopped, 1 L of distilled water was added thereto, and then, sodium hydroxide was added thereto until a pH of the resultant solution reached 12. Subsequently, the reaction product was extracted three times by using 1 L of ethyl acetate, wherein 1 L of ethyl acetate was divided into three portions and each thereof was used for the extraction. An organic layer was filtered by using a celite filter, and concentrated, and then, 300 ml of methanol was added, and the produced solid was filtered and dried to obtain 40 g (yield: 46%) of Intermediate A.

1H-NMR (300 MHz, CDCl$_3$) δ 9.31 (m, 1H), 9.00 (m, 1H), 8.32 (m, 2H), 8.07 (m, 2H), 7.78 (m, 1H), 7.52 (m, 1H)

Synthesis of Intermediate B

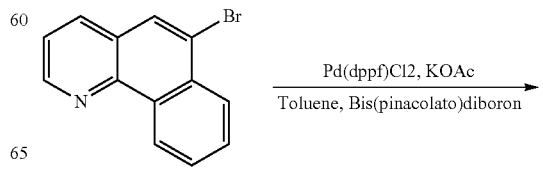

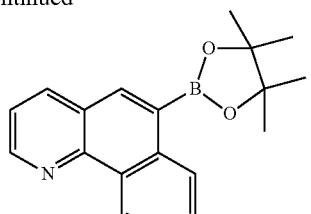

Intermediate B

In a 2 L round-bottomed flask, 40 g (154.97 mmol) of Intermediate A, 3.8 g (4.65 mmol) of Pd(dppf)Cl$_2$ ([1,1'-Bis(diphenylphosphino)ferrocene]dichloropalladium(II)), 47.2 g (185.97 mmol) of bis(pinacolato)diboron, and 45.63 g (464.92 mmol) of potassium acetate were mixed with 800 ml of toluene, and then, the mixture was refluxed for 12 hours while stirring. After the reaction stopped, the reaction solution was cooled to room temperature and filtered, and then the filtrate was concentrated. 300 ml of toluene was added to the result obtained therefrom, and then, charcoal was added thereto. The result was stirred for 30 minutes and filtered by using silica gel. The resultant filtrate was concentrated and then 300 ml of methanol was added thereto, thereby producing a solid. The solid was filtered and dried to obtain 40.5 g (yield: 86%) of Intermediate B.

Synthesis of Intermediate C

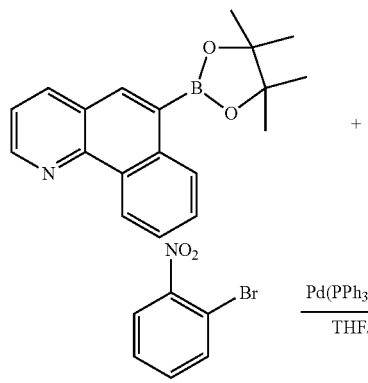

Intermediate C

In a 2 L round-bottomed flask, 40.5 g (132.71 mmol) of Intermediate B, 26.8 g (132.71 mmol) of 2-bromonitrobenzene, 4.6 g (3.98 mmol) of tetrakis(triphenylphosphine)palladium(0), and 36.68 g (265.42 mmol) of potassium carbonate were mixed with 700 ml of THF and 300 ml of distilled water, and then, the mixture was refluxed for 12 hours while stirring. After the reaction stopped, the reaction solution was cooled to room temperature and then extracted, and an organic layer was concentrated, extracted by using methylene chloride, and then filtered by using silica gel to produce a filtrate. 200 ml of methanol was added to the filtrate, thereby producing a solid. The solid was filtered and dried to obtain 37.50 g (yield: 94%) of Intermediate C.

Synthesis of Intermediate D

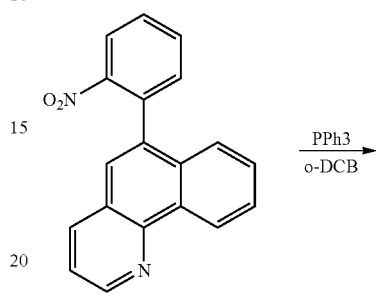

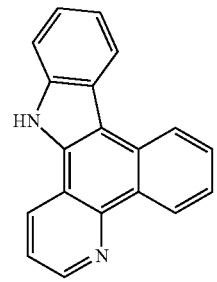

Intermediate D

In a 1 L round-bottomed flask, 37.5 g (124.87 mmol) of Intermediate C and 98.25 g (374.61 mmol) of triphenylphosphine were mixed with 300 ml of 1,2-dichlorobenzene, and then the mixture was refluxed while stirring. When the reaction stopped, the 1,2-dichlrorobenzene was removed under reduced pressure, and then, silica gel column chromatography (Hex:EA=1:1 volume/volume) was performed thereon to obtain 26 g (yield: 78%) of Intermediate D.

Synthesis of Compound 1

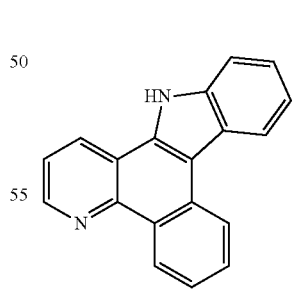

Intermediate D

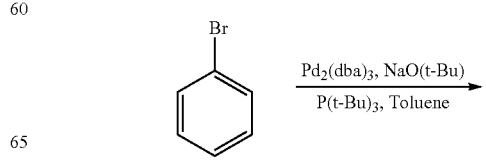

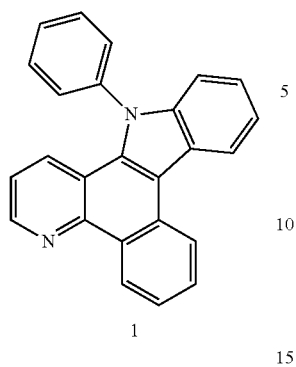

1

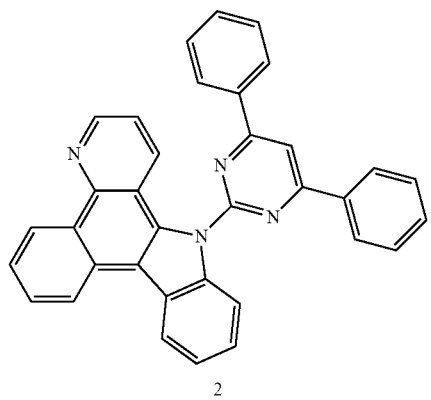

2

In a 1 L round-bottomed flask, 3.2 g (11.93 mmol) of Intermediate D, 2.25 g (14.31 mmol) of bromobenzene, 1.09 g (1.19 mmol) of tris(dibenzylideneacetone)dipalladium (0) (Pd$_2$(dba)$_3$), 3.44 g (35.78 mmol) of sodium tert-butoxide, and 0.241 g (1.19 mmol) of tri-tert-butylphosphine (50% in toluene) were mixed with 60 ml of toluene, and then, the mixture was refluxed for 12 hours while stirring. After the reaction stopped, the reaction solution was cooled to room temperature, and then, filtered by using silica gel, and the filtrate was concentrated. Silica gel chromatography (Hex: EA=3:1 volume/volume) was performed thereon to obtain 2.8 g (yield: 68%) of Compound 1.

1H-NMR (300 MHz, CDCl$_3$) δ 9.44 (d, 1H, J=6.96), 8.88 (dd, 2H), 8.65 (d, 1H, J=7.29), 7.87 (t, 1H, J=8.16), 7.67 (m, 5H), 7.44 (m, 4H), 7.18 (m, 2H)

Synthesis Example 2

Synthesis of Compound 2

In a 1 L round-bottomed flask, 13 g (48.45 mmol) of Intermediate D, which was prepared according to Synthesis Example 1, 14.22 g (53.30 mmol) of Intermediate E, 4.44 g (4.85 mmol) of Pd$_2$(dba)$_3$, 13.97 g (145.35 mmol) of sodium tert-butoxide, and 0.980 g (4.85 mmol) of tri-tert-butylphosphine (50% in toluene) were mixed with 250 ml of toluene, and then, the mixture was refluxed for 12 hours while stirring. After the reaction stopped, the reaction solution was cooled to room temperature, and then, added to 500 ml of methanol, and a produced solid was filtered therefrom. The result was dried, and then, added 360 ml of monochlorobenzene, and the resultant mixture was stirred while heating, followed by filtration with silica gel. The obtained filtrate was cooled to room temperature, and then, 500 ml of methanol was added thereto, thereby producing a solid. The solid was filtered to obtain 12.50 g (yield: 52%) of Compound 2.

1H-NMR (300 MHz, CDCl$_3$) δ 9.44 (d, 1H, J=7.20), 9.01 (m, 2H), 8.82 (m, 2H), 8.34 (m, 4H), 8.25 (m, 1H), 7.96 (m, 2H), 7.81 (t, 1H, J=7.23), 7.57 (m, 8H), 7.45 (m, 1H)

Synthesis Example 3

Synthesis of Compound 4

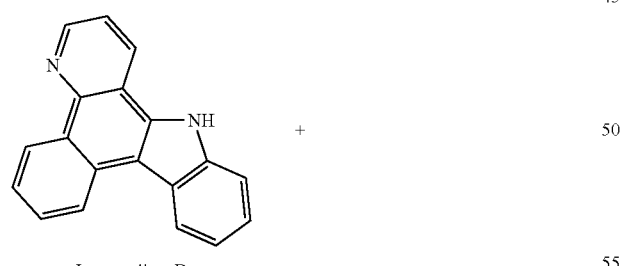

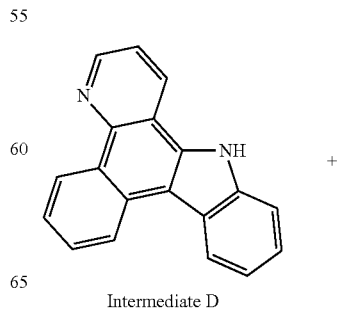

Intermediate D

-continued

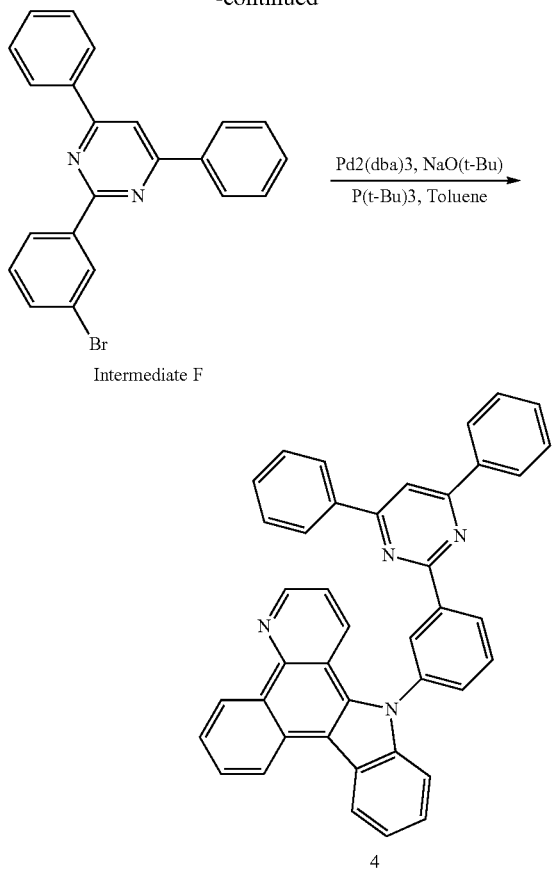

Intermediate F

4

In a 1 L round-bottomed flask, 13.6 g (50.69 mmol) of Intermediate D, which was prepared according to Synthesis Example 1, 21.59 g (55.76 mmol) of Intermediate F, 4.64 g (5.07 mmol) of $Pd_2(dba)_3$, 14.615 g (152.06 mmol) of sodium tert-butoxide, and 1.03 g (5.07 mmol) of tri-tert-butylphosphine (50% in toluene) were mixed with 250 ml of toluene, and then, the mixture was refluxed for 12 hours while stirring. After the reaction stopped, the reaction solution was cooled to room temperature, and then, added to 500 ml of methanol, and a produced solid was filtered therefrom. The result was dried, and then, added 360 ml of monochlorobenzene, and the resultant mixture was stirred while heating, followed by filtration with silica gel. The obtained filtrate was cooled to room temperature, and then, 500 ml of methanol was added thereto, thereby producing a solid. The solid was filtered to obtain 20.39 g (yield: 70%) of Compound 4.

1H-NMR (300 MHz, CDCl$_3$) δ 9.44 (d, 1H, J=7.20), 9.01 (m, 2H), 8.82 (m, 2H), 8.34 (m, 4H), 8.25 (m, 1H), 7.96 (m, 2H), 7.81 (t, 1H, J=7.23), 7.57 (m, 8H), 7.45 (m, 1H)

Evaluation Example 1

Evaluation on HOMO, LUMO and Triplet ($T_1$) Energy Level of Compounds 1, 2, and 4

According to the methods shown in Table 2, HOMO, LUMO and triplet ($T_1$) energy level of Compounds 1, 2, and 4 were measured, and results thereof are shown in Table 3.

TABLE 2

| | |
|---|---|
| HOMO energy level evaluation method | Each compound was diluted with CHCl$_3$ to a concentration of 1 × 10$^{-5}$M, and a UV absorption spectrum thereof was measured at room temperature by using a Shimadzu UV-350 spectrometer, and then, a HOMO energy level was measured from an edge of the absorption spectrum by using an optical band gap (Eg) |
| LUMO energy level evaluation method | Cyclic voltammetry (CV) (electrolyte: 0.1M Bu$_4$NClO$_4$/ solvent: CH$_2$Cl$_2$/electrode: 3 electrode system (working electrode: GC, reference electrode: Ag/AgCl, auxiliary electrode: Pt)) was used to obtain a potential (V)-current (A) graph of each compound, and then, from a reduction onset of the graph, a LUMO energy level of each compound was measured. |
| T1 energy level evaluation method | A mixture of toluene and each compound (1 mg of each compound in 3 cc of toluene) was placed in a quartz cell, and then placed in liquid nitrogen (77 K). A photoluminescence spectrum thereof was measured by using a photoluminescence tester, and the obtained spectrum was compared with a conventional room temperature photoluminescence spectrum to analyze peaks located only in a low temperature range to calculate a T1 energy level |

TABLE 3

| Compound No. | HOMO(eV) (cal.) | LUMO(eV) (cal.) | T1 energy level (eV) |
|---|---|---|---|
| Compound 1 | −5.792 | — | 2.540 |
| Compound 2 | −5.980 | −2.660 | 2.510 |
| Compound 4 | −5.847 | −2.610 | 2.540 |

From Table 3, it was confirmed that Compounds 1, 2, and 4 have electric characteristics suitable for use as a material for an organic light-emitting device.

Evaluation Example 2

Evaluation on Thermal Characteristics of Compounds 2 and 4

Thermal analysis (N2 atmosphere, temperature range: from room temperature to 800° C. (10° C./min)-TGA, from room temperature to 400° C.-DSC, Pan Type: Pt Pan in disposable Al Pan(TGA), disposable Al pan(DSC)) was performed on Compounds 2 and 4 by using thermo gravimetric analysis (TGA) and differential scanning calorimetry (DSC). TGA data of Compound 2, DSC data of Compound 2, TGA data of Compound 4, and DSC data of Compound 4 are respectively shown in FIGS. 2A, 2B, 3A, and 3B and shown in Table 4 below. According to FIGS. 2A, 2B, 3A, 3B, and Table 4, Compounds 2 and 4 have excellent thermal stability.

TABLE 4

| | Tc (° C.) | Tm (° C.) | Tg (° C.) |
|---|---|---|---|
| Compound 2 | — | 307.05 | — |
| Compound 4 | 271.34 | 291.26 | 131.42 |

Example 1

A glass substrate with a 1,500 Å-thick indium tin oxide (ITO) electrode (first electrode, anode) thereon was washed with distilled water ultrasonic waves. When the distilled water washing was finished, the glass substrate was ultrasonic-wave washed with a solvent, such as isopropyl alcohol, acetone, or methanol, and then dried.

Compound HT5 was vacuum deposited on the ITO electrode on the glass substrate to form a hole transport layer having a thickness of 1,200 Å to form a hole transport region.

Compound 1(host) and PhGD (dopant, 7 percent by weight, wt %) were co-deposited on the hole transport region to form an emission layer having a thickness of 300 Å.

BAlq was vacuum deposited on the emission layer to form a first electron transport layer having a thickness of 50 Å. $Alq_3$ was vacuum deposited on the first electron transport layer to form a second electron transport layer having a thickness of 250 Å, and then, LiF was deposited on the second electron transport layer to form an electron injection layer having a thickness of 5 Å. An Al second electrode (cathode) having a thickness of 1,000 Å is formed on the electron injection layer to manufacture an organic light-emitting device.

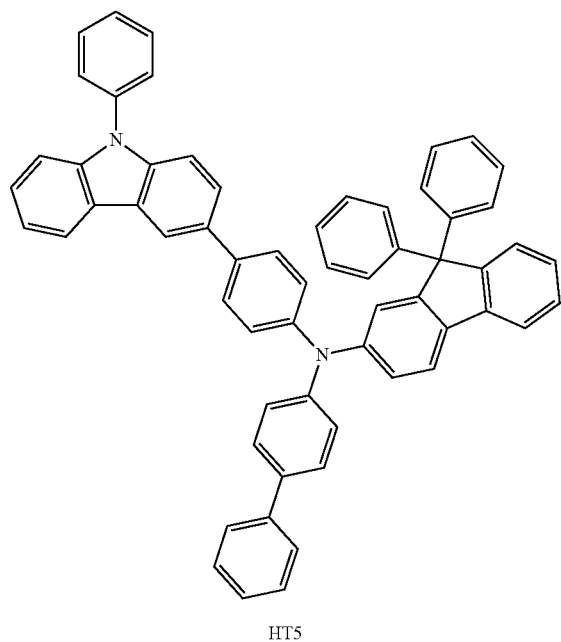

HT5

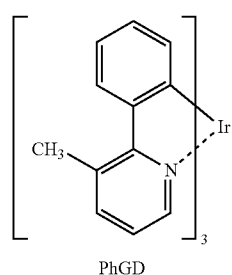

PhGD

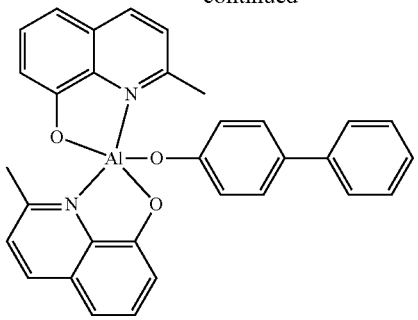

BAlq

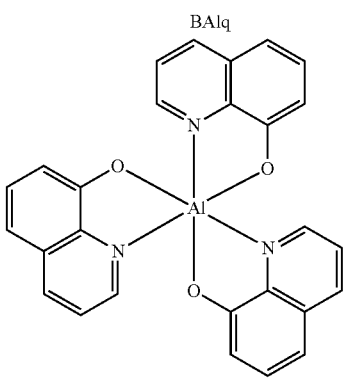

Alq₃

Example 2

An organic light-emitting device was manufactured in the same manner as in Example 1, except that as a host, Compound 2 was used instead of Compound 1.

Example 3

An organic light-emitting device was manufactured in the same manner as in Example 1, except that as a host, Compound 4 was used instead of Compound 1.

Comparative Example 1

An organic light-emitting device was manufactured in the same manner as in Example 1, except that as a host, CBP was used instead of Compound 1.

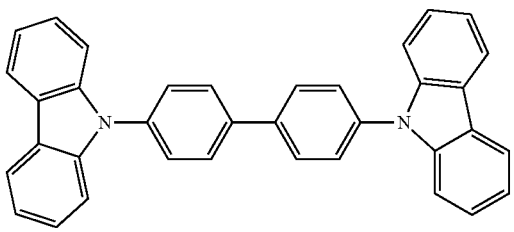

CBP

Evaluation Example 3

Evaluation on Characteristics of Organic Light-Emitting Device

Regarding the organic light-emitting devices manufactured according to Examples 1 to 3 and Comparative Example 1, a change in current density according to voltage, a change in brightness, and luminance efficiency was measured. A detailed measuring method is provided below and results thereof are shown in Table 5 below:

(1) Change in Current Density According to Voltage

Regarding the organic light-emitting devices, a current flowing through a unit device was measured by using a current-voltage system (Keithley 2400) while the voltage was increased from 0 volts (V) to 10 V, and current measurement values were divided by an area.

(2) Change in Brightness According to Voltage

Regarding the organic light-emitting devices, brightness was measured by using a current-voltage system (Keithley 2400) while the voltage was increased from 0 V to 10 V, and current measurement values were divided by an area.

(3) Luminance Efficiency Measurement

Current efficiency (cd/A) at the same current density (10 milliampere per square centimeter, $mA/cm^2$) was measured by using brightness values measured from (1) and (2), current density, and voltage.

TABLE 5

| | Host | Dopant | Driving voltage (V) | Efficiency (cd/A) | Color coordinate CIE x | CIE y |
|---|---|---|---|---|---|---|
| Example 1 | Compound 1 | PhGD | 7.5 | 40.5 | 0.33 | 0.62 |
| Example 2 | Compound 2 | PhGD | 6.5 | 47.6 | 0.34 | 0.62 |
| Example 3 | Compound 4 | PhGD | 6.1 | 46.2 | 0.34 | 0.62 |
| Comparative Example 1 | CBP | PhGD | 8.5 | 45.4 | 0.33 | 0.62 |

From Table 5, it was confirmed that the organic light-emitting devices manufactured according to Examples 1 to 3 have lower driving voltage and higher efficiency than the organic light-emitting device manufactured according to Comparative Example 1.

The condensed-cyclic compound according to embodiments has excellent electric characteristics and thermal stability. Accordingly, an organic light-emitting device including the condensed-cyclic compound may have a low driving voltage, high efficiency, high brightness, and a long lifespan.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A condensed-cyclic compound represented by Formula 1:

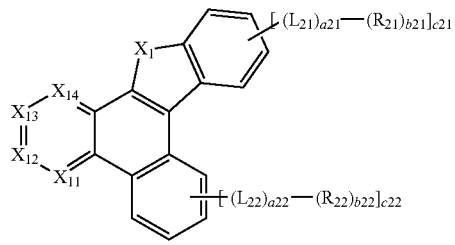

Formula 1 wherein, in Formula 1,
$X_1$ is selected from $N-[(L_1)_{a1}-(R_1)_{b1}]$, S, O, S(=O), $S(=O)_2$, and $Si(R_2)(R_3)$;
$X_{11}$ is N or $C-[(L_{11})_{a11}-(R_{11})_{b11}]$,
$X_{12}$ is N or $C-[(L_{12})_{a12}-(R_{12})_{b12}]$,
$X_{13}$ is N or $C-[(L_{13})_{a13}-(R_{13})_{b13}]$, and
$X_{14}$ is N or $C-[(L_{14})_{a14}-(R_{14})_{b14}]$, provided that at least one of $X_{11}$ to $X_{14}$ is N;
$L_1$, $L_{11}$, $L_{12}$, $L_{13}$, $L_{14}$, $L_{21}$, and $L_{22}$ are each independently selected from a substituted or unsubstituted $C_3$-$C_{10}$ cycloalkylene group, a substituted or unsubstituted $C_3$-$C_{10}$ heterocycloalkylene group, a substituted or unsubstituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic hetero-condensed polycyclic group;
a1, a11, a12, a13, a14, a21, and a22 are each independently selected from an integer of 0 to 5;
$R_1$, $R_2$, $R_3$, $R_{11}$, $R_{12}$, $R_{13}$, $R_{14}$, $R_{21}$, and $R_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic hetero-condensed polycyclic group, $—N(Q_1)(Q_2)$, $—Si(Q_3)(Q_4)(Q_5)$, and $—B(Q_6)(Q_7)$;
b1, b11, b12, b13, b14, b21, and b22 are each independently selected from an integer of 1 to 5;
c21 and c22 are each independently 1, 2, 3, or 4, provided that
when c21 is two or more, groups $*-(L_{21})_{a21}-(R_{21})_{b21}$ are identical or different, and
when c22 is two or more, groups $*-(L_{22})_{a22}-(R_{22})_{b22}$ are identical or different; and
at least one of the substituted $C_3$-$C_{10}$ cycloalkylene group, the substituted $C_3$-$C_{10}$ heterocycloalkylene group, the substituted $C_3$-$C_{10}$ cycloalkenylene group, the substituted $C_3$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic hetero-condensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_3$-$C_{10}$ heterocycloalkyl group, the substituted $C_3$-$C_{10}$ cycloalkenyl group, the substituted $C_3$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ hetero aryl group, the substituted monovalent non-aromatic condensed polycyclic group, and the substituted monovalent non-aromatic hetero-condensed polycyclic group is substituted with a group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a monovalent non-aromatic condensed polycyclic group, a monovalent non-aromatic hetero-condensed polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a monovalent non-aromatic condensed polycyclic group, and a monovalent non-aromatic hetero-condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a monovalent non-aromatic condensed polycyclic group, and a monovalent non-aromatic hetero-condensed polycyclic group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a C6-C60 aryloxy group, a C6-C60 arylthio group, a $C_2$-$C_{60}$ hetero aryl group, a monovalent non-aromatic condensed polycyclic group, a monovalent non-aromatic hetero-condensed polycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$); wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a C3-C10 cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a monovalent non-aromatic condensed polycyclic group, and a monovalent non-aromatic hetero-condensed polycyclic group.

2. The condensed-cyclic compound of claim 1, wherein $X_1$ is N-[($L_1$)$_{a1}$-$R_1$].

3. The condensed-cyclic compound of claim 1, wherein
$X_{11}$ is N,
$X_{12}$ is C-[($L_{12}$)$_{a12}$-$R_{12}$],
$X_{13}$ is C-[($L_{13}$)$_{a13}$-$R_{13}$], and
$X_{14}$ is C-[($L_{14}$)$_{a14}$-$R_{14}$].

4. The condensed-cyclic compound of claim 1, wherein $L_1$, $L_{11}$, $L_{12}$, $L_{13}$, $L_{14}$, $L_{21}$, and $L_{22}$ are each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, a oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, a oxadiazolylene group, a triazinylene group, a dibenzofuranylene group, a dibenzothiophenylene group, a benzocarbazolylene group, a dibenzocarbazolylene group, and an imidazopyridinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, a oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, a oxadiazolylene group, a triazinylene group, a dibenzofuranylene group, a dibenzothiophenylene group, a benzocarbazolylene group, a dibenzocarbazolylene group, and an imidazopyridinylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group.

5. The condensed-cyclic compound of claim 1, wherein $L_1$, $L_{11}$, $L_{12}$, $L_{13}$, $L_{14}$, $L_{21}$, and $L_{22}$ are each independently selected from Formulae 2-1 to 2-33:

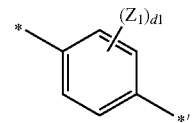
Formula 2-1

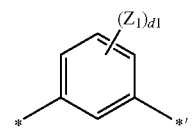
Formula 2-2

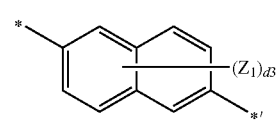
Formula 2-3

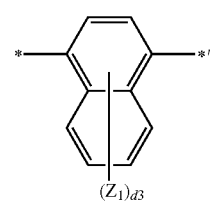
Formula 2-4

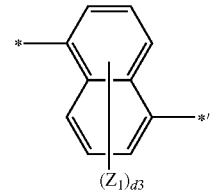
Formula 2-5

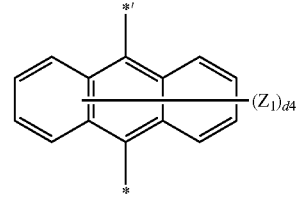
Formula 2-6

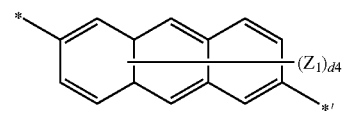
Formula 2-7

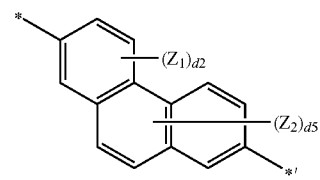
Formula 2-8

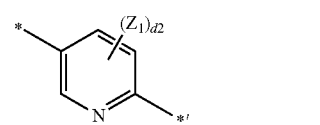
Formula 2-9

-continued
 Formula 2-10
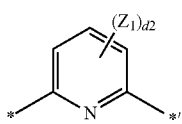 Formula 2-11
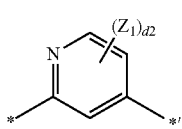 Formula 2-12
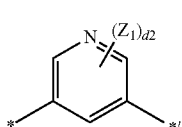 Formula 2-13
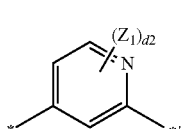 Formula 2-14
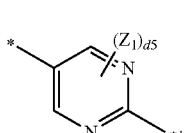 Formula 2-15
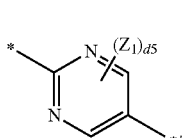 Formula 2-16
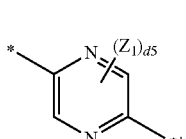 Formula 2-17
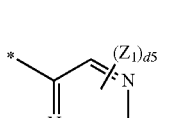 Formula 2-18
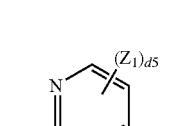 Formula 2-19
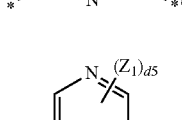 Formula 2-20
-continued
 Formula 2-21
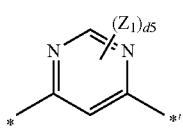 Formula 2-22
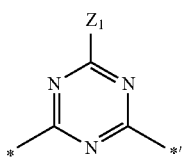 Formula 2-23
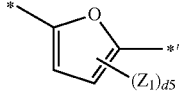 Formula 2-24
Formula 2-25
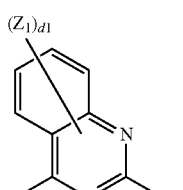 Formula 2-26
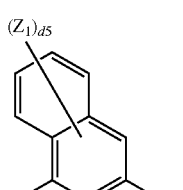 Formula 2-27
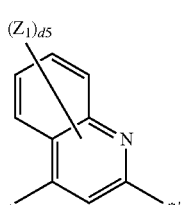 Formula 2-28
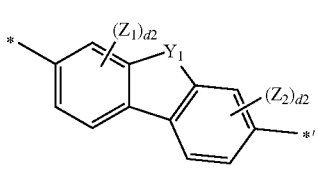 Formula 2-29

-continued

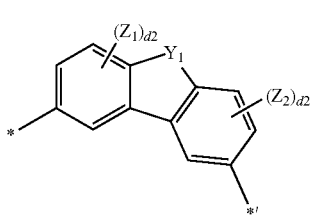
Formula 2-30

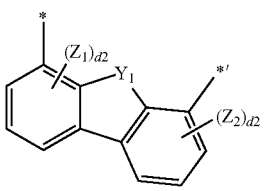
Formula 2-31

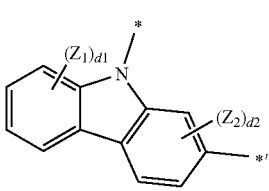
Formula 2-32

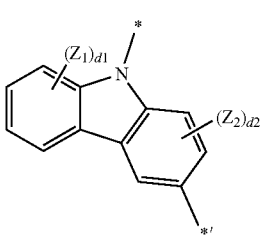
Formula 2-33 wherein, in Formulae 2-1 to 2-33, $Y_1$ is O, S, S(=O), S(=O)$_2$, C($Z_3$)($Z_4$), N($Z_5$), or Si($Z_6$)($Z_7$);

$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and —Si($Q_{33}$)($Q_{34}$)($Q_{35}$);

$Q_{33}$ to $Q_{35}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

d1 is an integer of 1 to 4;

d2 is an integer of 1 to 3;

d3 is an integer of 1 to 6;

d4 is an integer of 1 to 8;

d5 is 1 or 2;

d6 is an integer of 1 to 5; and

* and *' are binding sites to a neighboring atom.

6. The condensed-cyclic compound of claim 1, wherein $L_1$, $L_{11}$, $L_{12}$, $L_{13}$, $L_{14}$, $L_{21}$, and $L_{22}$ are each independently selected from Formulae 3-1 to 3-38:

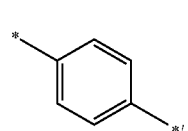
Formula 3-1

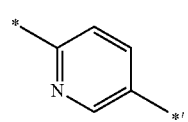
Formula 3-2

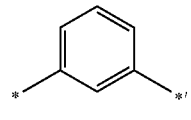
Formula 3-3

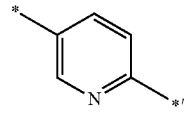
Formula 3-4

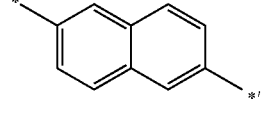
Formula 3-5

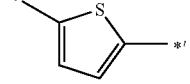
Formula 3-6

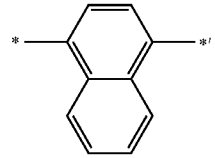
Formula 3-7

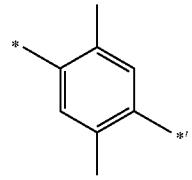
Formula 3-8

147
-continued
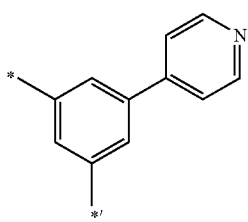
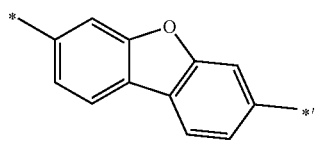
148
-continued
Formula 3-9
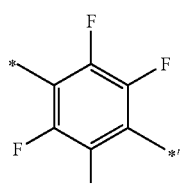
Formula 3-16
Formula 3-10
Formula 3-17
Formula 3-11
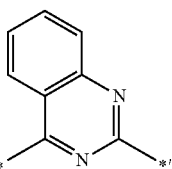
Formula 3-18
Formula 3-12
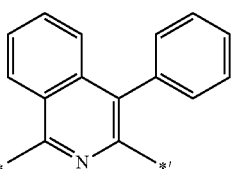
Formula 3-19
Formula 3-13
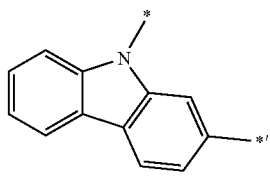
Formula 3-20
Formula 3-14
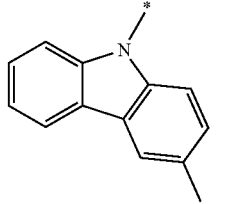
Formula 3-21
Formula 3-15
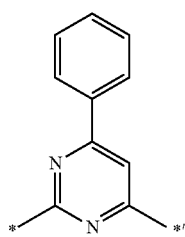
Formula 3-22

Formula 3-23
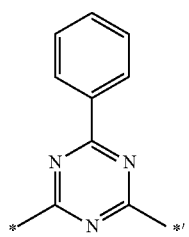
Formula 3-29
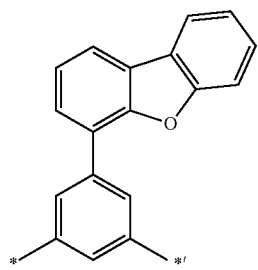
Formula 3-24
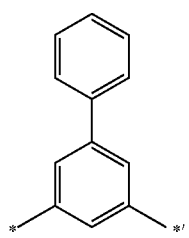
Formula 3-30
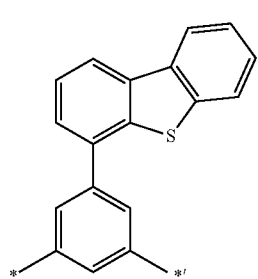
Formula 3-25
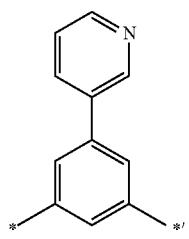
Formula 3-31
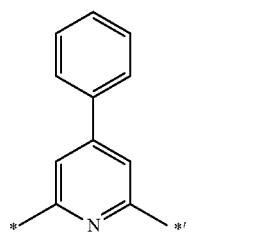
Formula 3-26
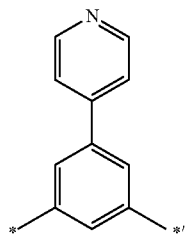
Formula 3-32
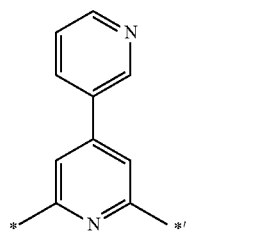
Formula 3-27
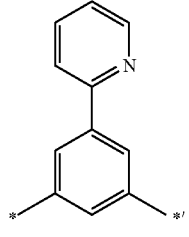
Formula 3-33
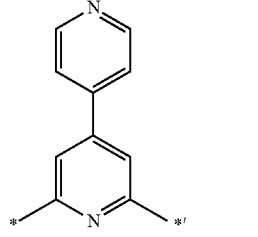
Formula 3-28
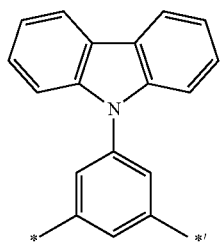
Formula 3-34
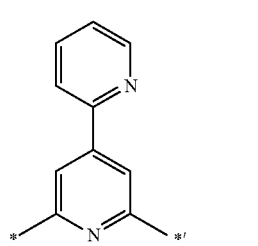

-continued

Formula 3-35

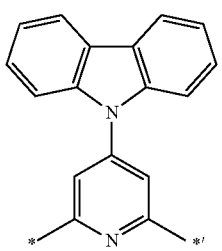

Formula 3-36

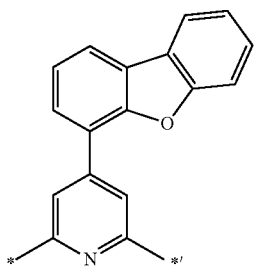

Formula 3-37

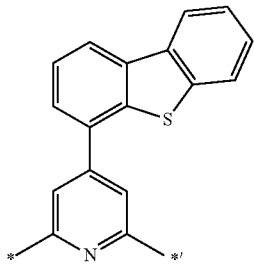

Formula 3-38

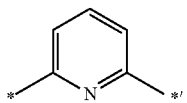

wherein, * and *' are binding sites to a neighboring atom.

7. The condensed-cyclic compound of claim 1, wherein a1, a11, a12, a13, a14, a21, and a22 are each independently 0, 1, or 2.

8. The condensed-cyclic compound of claim 1, wherein $R_1$ is selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_{33}$)($Q_{34}$)($Q_{35}$), a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group; wherein $Q_{33}$ to $Q_{35}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

9. The condensed-cyclic compound of claim 1, wherein $R_2$, $R_3$, $R_{11}$, $R_{12}$, $R_{13}$, $R_{14}$, $R_{21}$, and $R_{22}$ are each independently selected from a hydrogen, a deuterium, —F, —Cl, —Br, —I, a hydroxyl group, a cyano group, a nitro group, an amino group, an amidino group, a hydrazine group, a hydrazine group, a carboxylic acid or a salt thereof, a sulfonic acid or a salt thereof, a phosphoric acid or a salt thereof, a $C_1$-$C_{20}$ alkyl group, a $C_1$-$C_{20}$ alkenyl group, and a $C_1$-$C_{20}$ alkoxy group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a —Si($Q_{33}$)($Q_{34}$)($Q_{35}$), a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group; and —Si($Q_3$)($Q_4$)($Q_5$); wherein $Q_{33}$ to $Q_{35}$ and $Q_3$ to $Q_5$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

10. The condensed-cyclic compound of claim 1, wherein
$R_1$ is selected from Formulae 4-1 to 4-31;
$R_2$, $R_3$, $R_{11}$, $R_{12}$, $R_{13}$, $R_{14}$, $R_{21}$, and $R_{22}$ are each independently selected from
a hydrogen, a deuterium, —F, —Cl, —Br, —I, a hydroxyl group, a cyano group, a nitro group, an amino group, an amidino group, a hydrazine group, a hydrazine group, a carboxylic acid or a salt thereof, a sulfonic acid or a salt thereof, a phosphoric acid or a salt thereof, a $C_1$-$C_{20}$ alkyl group, a $C_1$-$C_{20}$ alkenyl group, and a $C_1$-$C_{20}$ alkoxy group;
Formulae 4-1 to 4-31; and
—Si($Q_3$)($Q_4$)($Q_5$); wherein
$Q_3$ to $Q_5$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group:

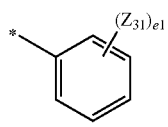

Formula 4-1

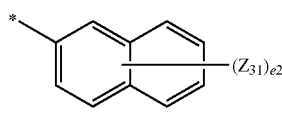

Formula 4-2

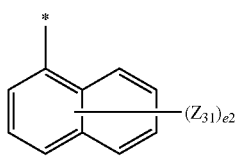

Formula 4-3

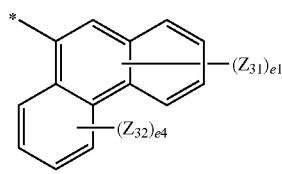

Formula 4-4

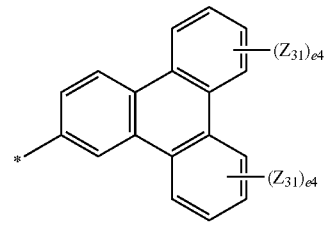

Formula 4-5

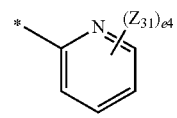

Formula 4-6

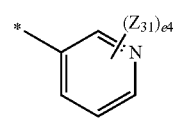

Formula 4-7

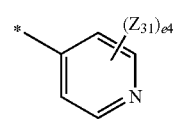

Formula 4-8

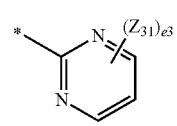

Formula 4-9

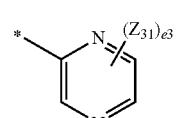

Formula 4-10

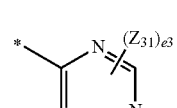

Formula 4-11

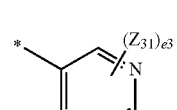

Formula 4-12

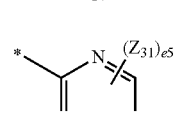

Formula 4-13

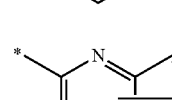

Formula 4-14

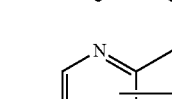

Formula 4-15

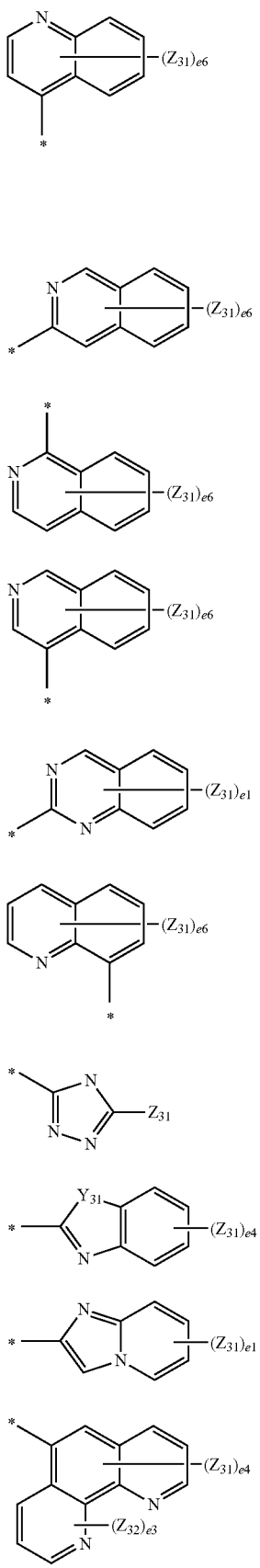
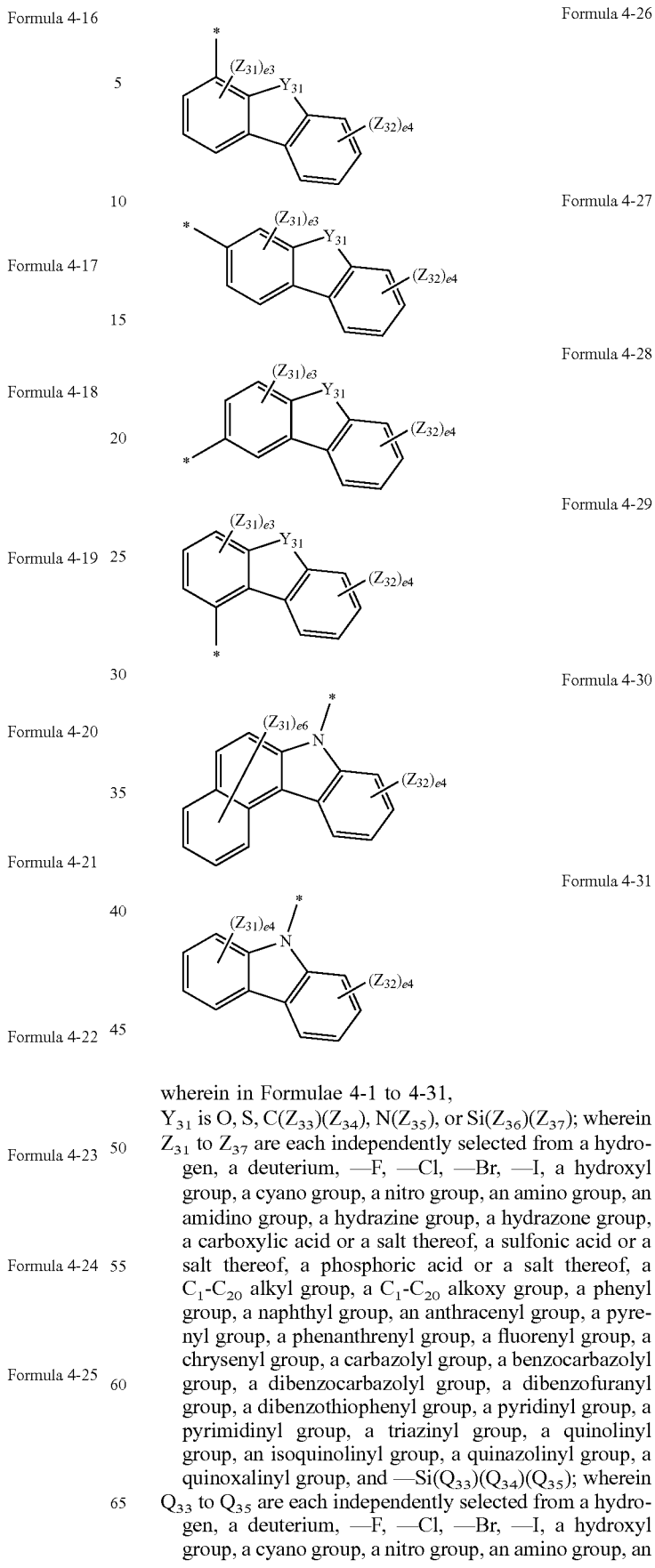

wherein in Formulae 4-1 to 4-31, $Y_{31}$ is O, S, $C(Z_{33})(Z_{34})$, $N(Z_{35})$, or $Si(Z_{36})(Z_{37})$; wherein $Z_{31}$ to $Z_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and —$Si(Q_{33})(Q_{34})(Q_{35})$; wherein $Q_{33}$ to $Q_{35}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

e1 is an integer of 1 to 5;
e2 is an integer of 1 to 7;
e3 is an integer of 1 to 3;
e4 is an integer of 1 to 4;
e5 is 1 or 2;
e6 is an integer of 1 to 6; and
* and *' are binding sites to a neighboring atom.

11. The condensed-cyclic compound of claim 1, wherein $R_1$ is selected from Formulae 5-1 to 5-80;
$R_2$, $R_3$, $R_{11}$, $R_{12}$, $R_{13}$, $R_{14}$, $R_{21}$, and $R_{22}$ are each independently selected from
a hydrogen, a deuterium, —F, —Cl, —Br, —I, a hydroxyl group, a cyano group, a nitro group, an amino group, an amidino group, a hydrazine group, a hydrazine group, a carboxylic acid or a salt thereof, a sulfonic acid or a salt thereof, a phosphoric acid or a salt thereof, a $C_1$-$C_{20}$ alkyl group, a $C_1$-$C_{20}$ alkenyl group, and a $C_1$-$C_{20}$ alkoxy group;
a $C_1$-$C_{20}$ alkyl and a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazine group, a carboxylic acid or a salt thereof, a sulfonic acid or a salt thereof, a phosphoric acid or a salt thereof, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;
Formulae 5-1 to 5-80; and
—Si($Q_3$)($Q_4$)($Q_5$); wherein
$Q_3$ to $Q_5$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

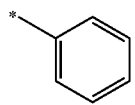

Formula 5-1

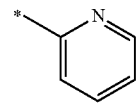

Formula 5-2

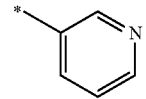

Formula 5-3

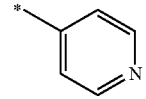

Formula 5-4

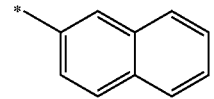

Formula 5-5

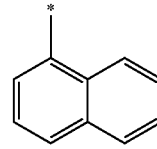

Formula 5-6

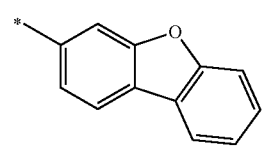

Formula 5-7

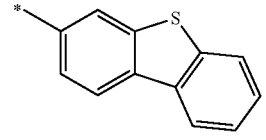

Formula 5-8

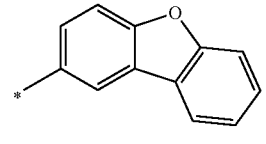

Formula 5-9

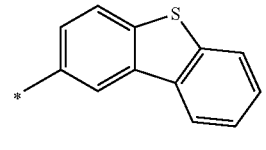

Formula 5-10

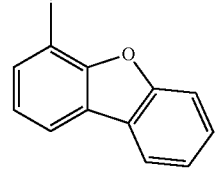

Formula 5-11

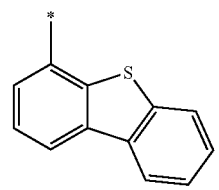

Formula 5-12

-continued
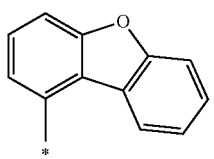
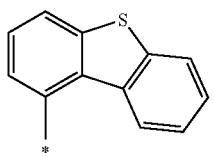
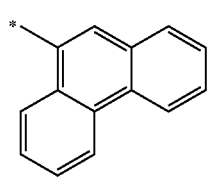
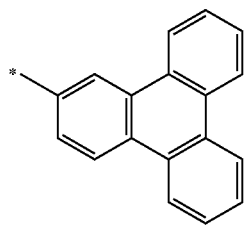
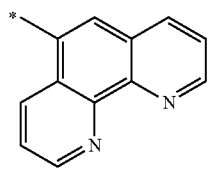
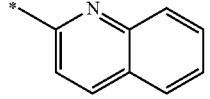
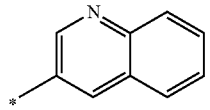
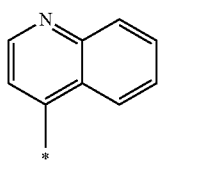
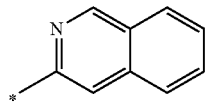
-continued
Formula 5-13
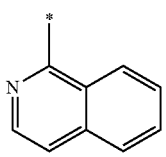
Formula 5-22
Formula 5-14
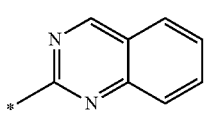
Formula 5-23
Formula 5-15
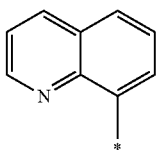
Formula 5-24
Formula 5-16
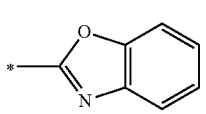
Formula 5-25
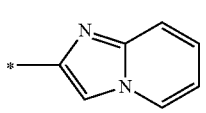
Formula 5-26
Formula 5-17
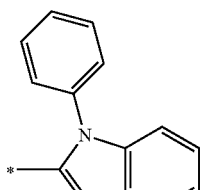
Formula 5-27
Formula 5-18
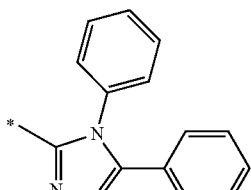
Formula 5-28
Formula 5-19
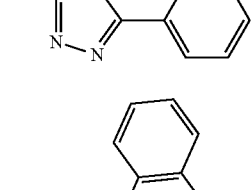
Formula 5-29
Formula 5-20
Formula 5-21
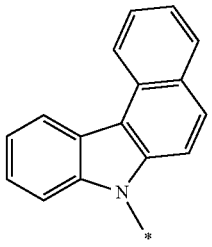
Formula 5-30

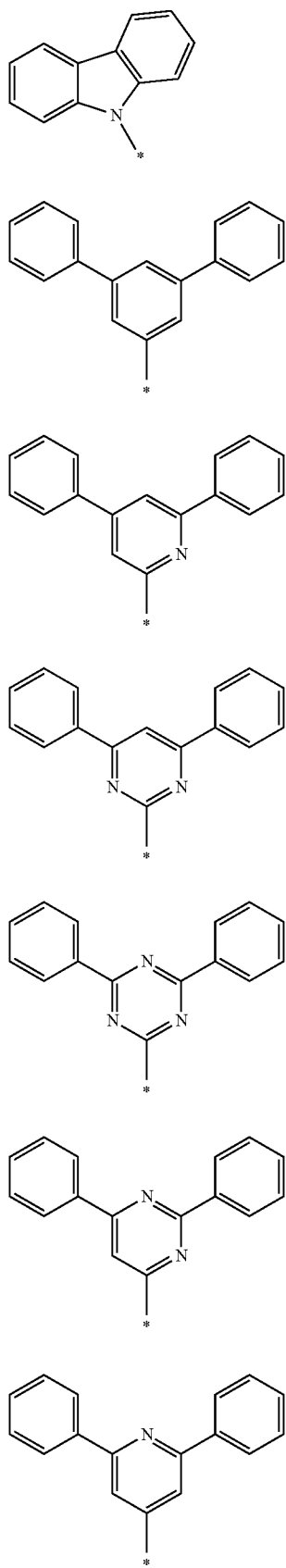

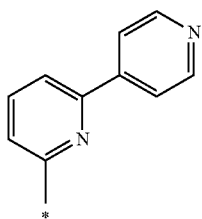
Formula 5-44
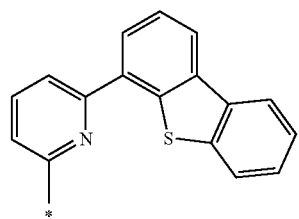
Formula 5-50
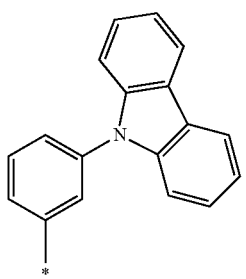
Formula 5-45
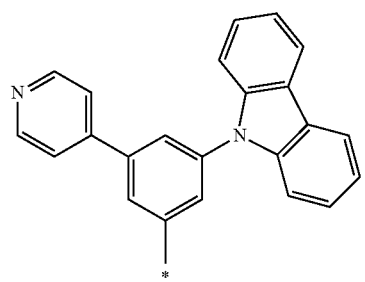
Formula 5-51
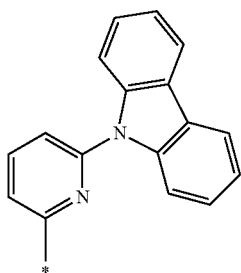
Formula 5-46
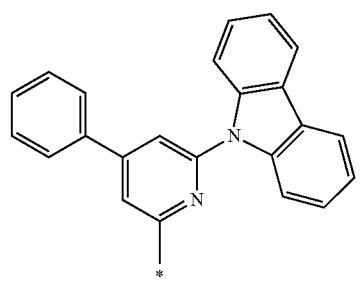
Formula 5-52
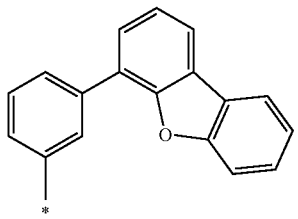
Formula 5-47
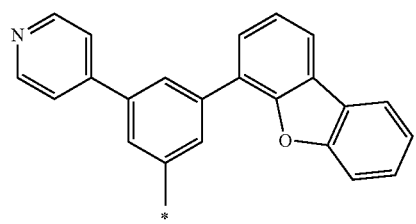
Formula 5-53
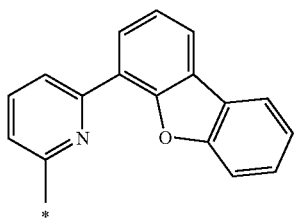
Formula 5-48
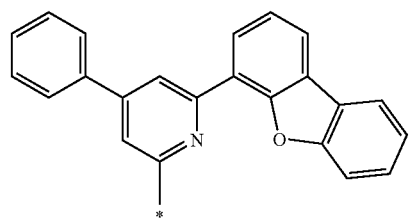
Formula 5-54
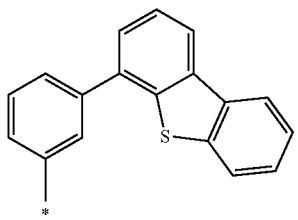
Formula 5-49
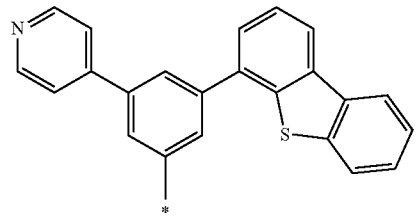
Formula 5-55

Formula 5-56
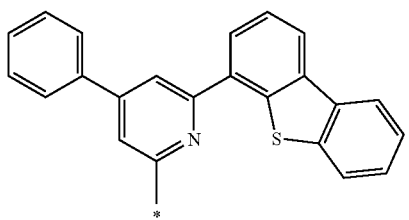
Formula 5-61
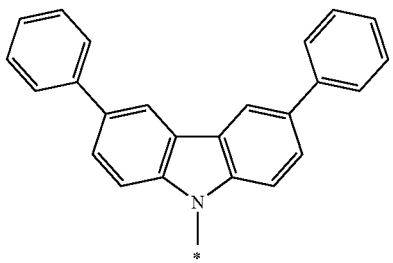
Formula 5-57
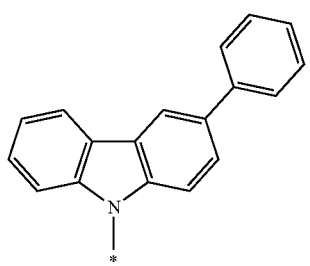
Formula 5-62
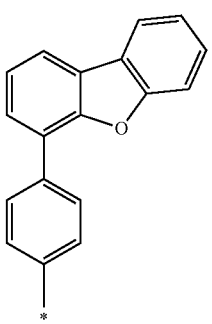
Formula 5-58
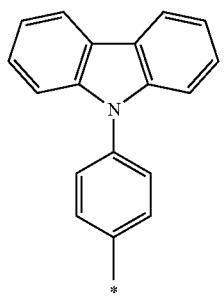
Formula 5-63
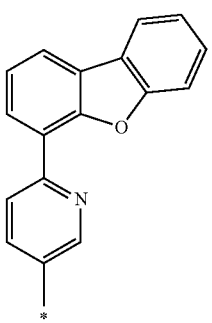
Formula 5-59
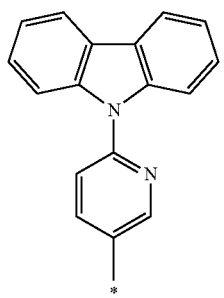
Formula 5-64
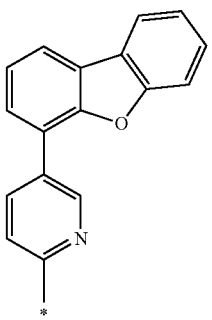
Formula 5-60
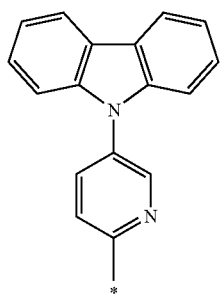
Formula 5-65
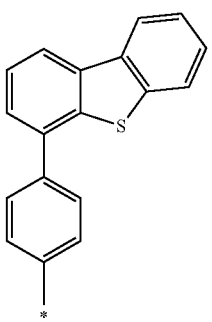

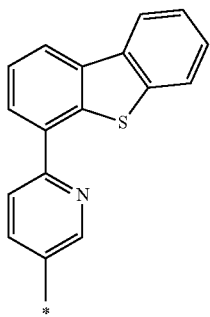
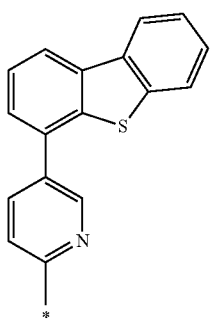
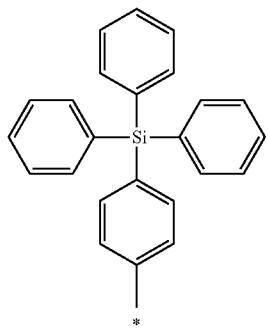
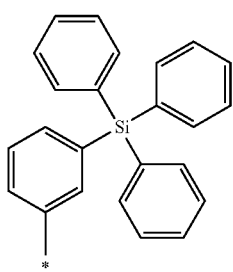
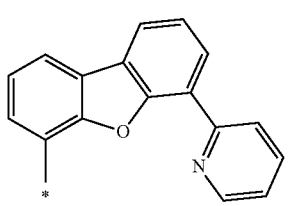
Formula 5-66
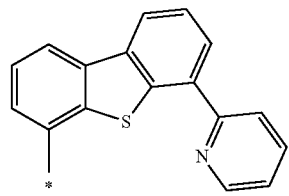
Formula 5-71
Formula 5-67
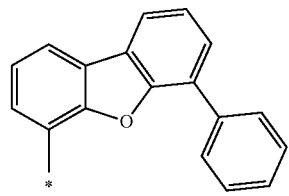
Formula 5-72
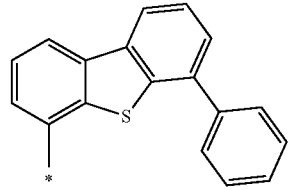
Formula 5-73
Formula 5-68
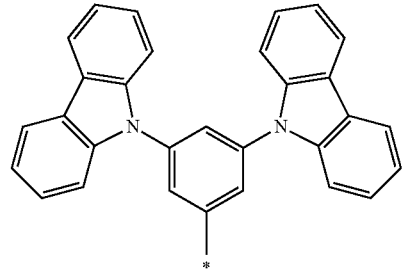
Formula 5-74
Formula 5-69
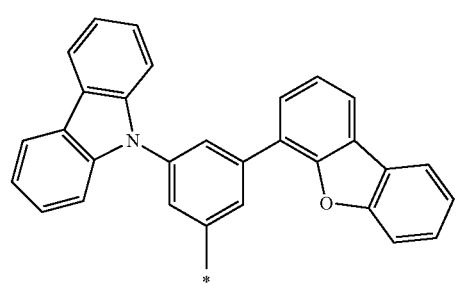
Formula 5-75
Formula 5-70
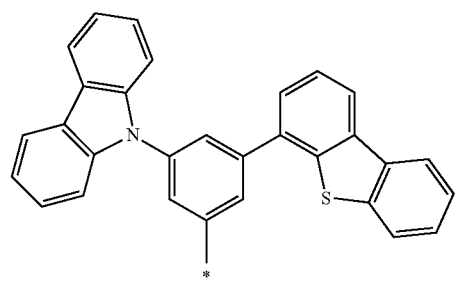
Formula 5-76

-continued
Formula 5-77
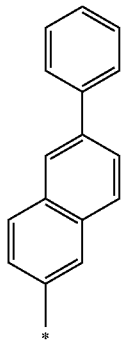
Formula 5-78
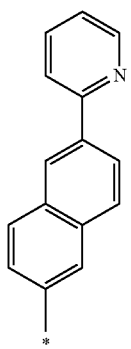
Formula 5-79
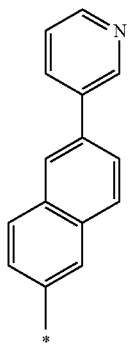
Formula 5-80
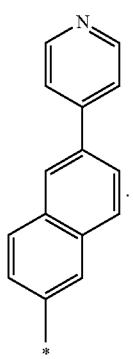
12. The condensed-cyclic compound of claim 1, represented by Formula 1A or 1B:
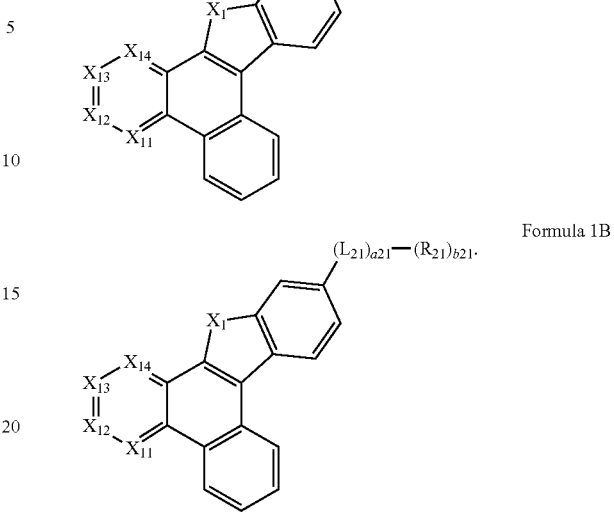
Formula 1A
Formula 1B
13. The condensed-cyclic compound of claim 1, represented by Formula 1A(1):
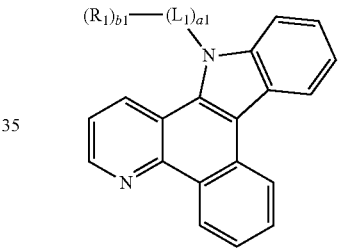
Formula 1A(1)
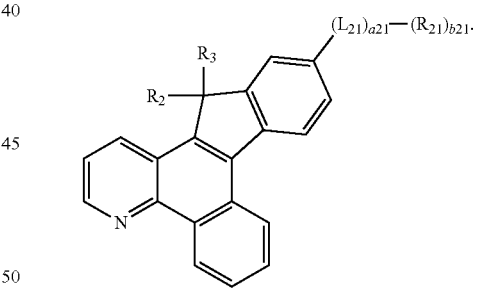
14. The condensed-cyclic compound of claim 13, wherein
$L_1$ is selected from Formulae 2-1 to 2-33;
a1 is 0 or 1; and
$R_1$ is selected from Formulae 4-1 to 4-31:
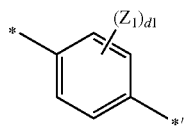
Formula 2-1

-continued
Formula 2-2
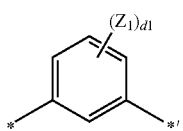
Formula 2-3
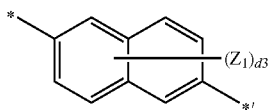
Formula 2-4
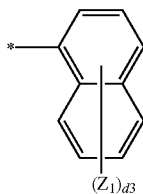
Formula 2-5
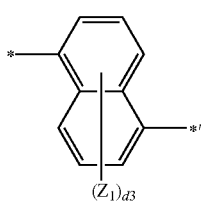
Formula 2-6
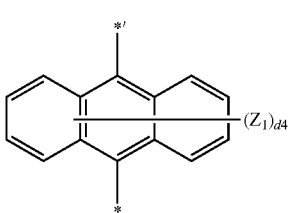
Formula 2-7
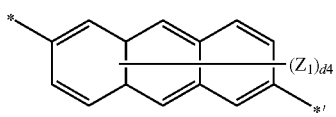
Formula 2-8
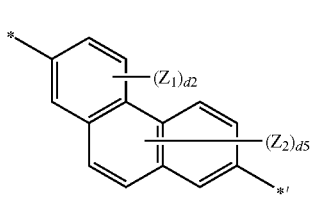
Formula 2-9
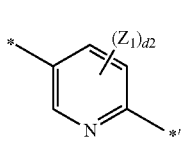
Formula 2-10
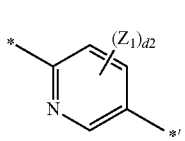
-continued
Formula 2-11
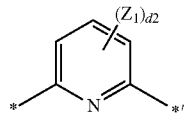
Formula 2-12
Formula 2-13
Formula 2-14
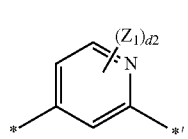
Formula 2-15
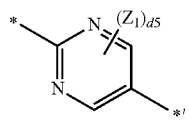
Formula 2-16
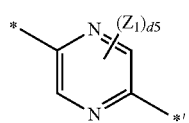
Formula 2-17
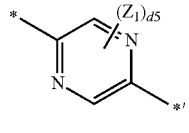
Formula 2-18
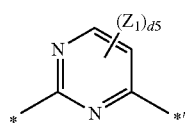
Formula 2-19
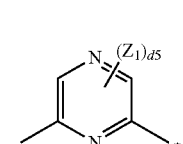
Formula 2-20
Formula 2-21

-continued

Formula 2-22
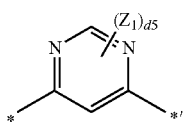

Formula 2-23
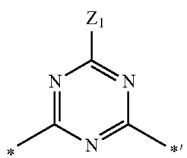

Formula 2-24
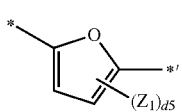

Formula 2-25
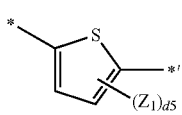

Formula 2-26
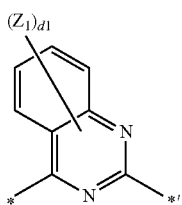

Formula 2-27
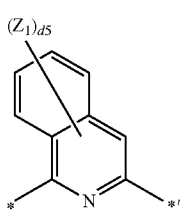

Formula 2-28
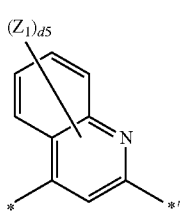

Formula 2-29
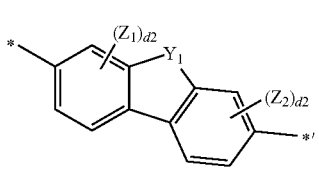

Formula 2-30
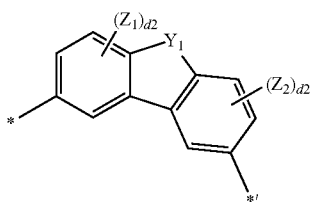

Formula 2-31
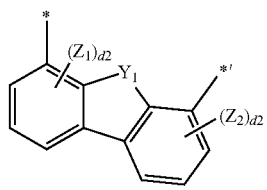

Formula 2-32
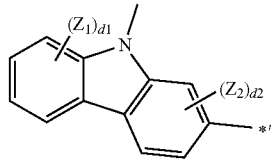

Formula 2-33
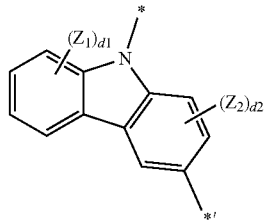

wherein in Formulae 2-1 to 2-33, $Y_1$ is O, S, S(=O), S(=O)$_2$, C($Z_3$)($Z_4$), N($Z_5$), or Si($Z_6$)($Z_7$);

$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and —Si($Q_{33}$)($Q_{34}$)($Q_{35}$); wherein $Q_{33}$ to $Q_{35}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

d1 is an integer of 1 to 4;
d2 is an integer of 1 to 3;
d3 is an integer of 1 to 6;

d4 is an integer of 1 to 8;
d5 is 1 or 2;
d6 is an integer of 1 to 5; and
* and *' are binding sites to a neighboring atom;
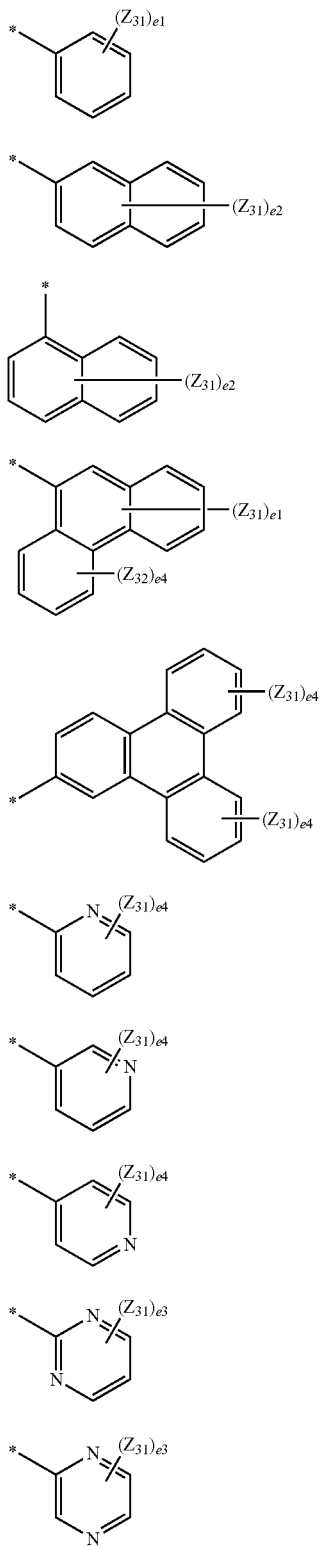
Formula 4-1
Formula 4-2
Formula 4-3
Formula 4-4
Formula 4-5
Formula 4-6
Formula 4-7
Formula 4-8
Formula 4-9
Formula 4-10
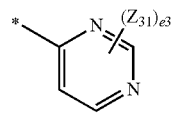
Formula 4-11
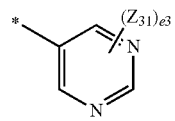
Formula 4-12
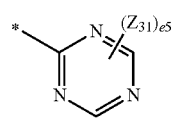
Formula 4-13
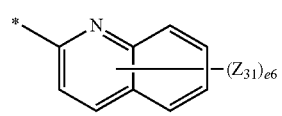
Formula 4-14
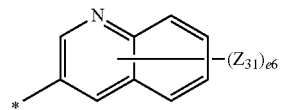
Formula 4-15
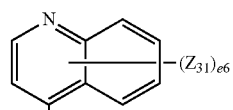
Formula 4-16
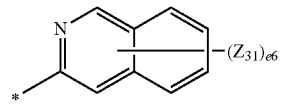
Formula 4-17
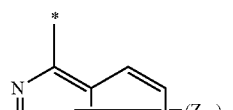
Formula 4-18
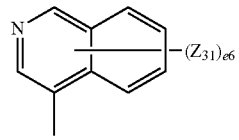
Formula 4-19
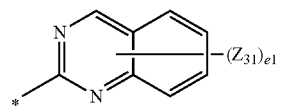
Formula 4-20
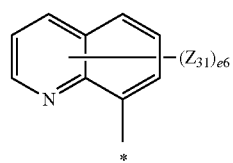
Formula 4-21

-continued

Formula 4-22

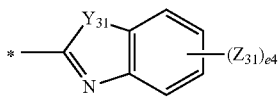

Formula 4-23

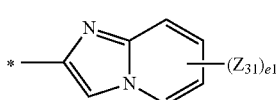

Formula 4-24

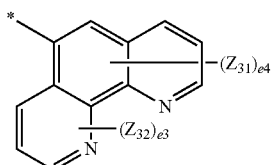

Formula 4-25

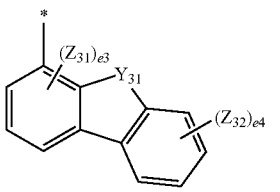

Formula 4-26

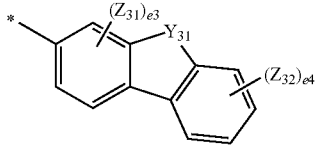

Formula 4-27

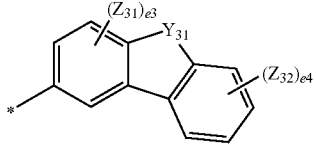

Formula 4-28

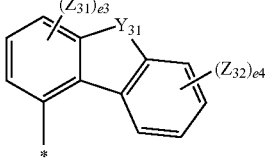

Formula 4-29

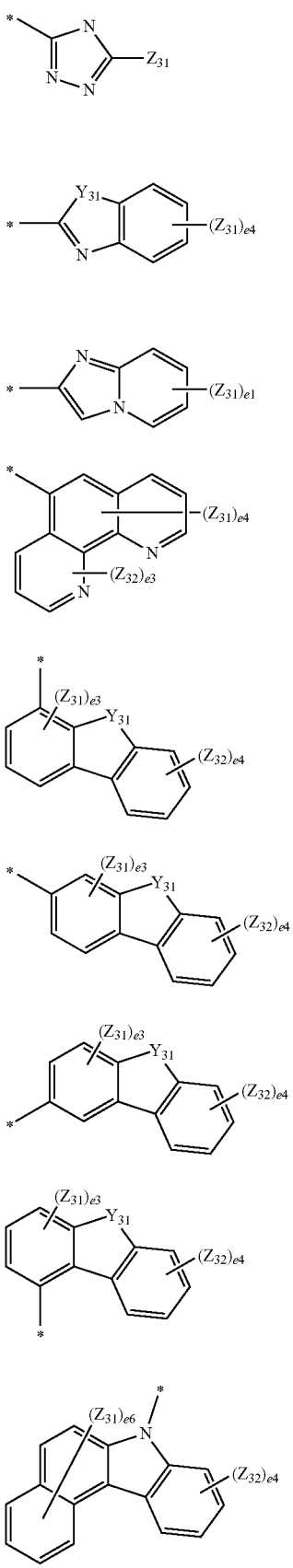

Formula 4-30

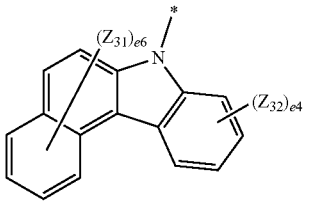

-continued

Formula 4-31

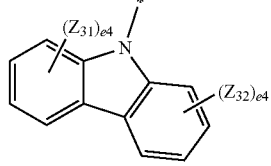

wherein in Formulae 4-1 to 4-31,
$Y_{31}$ is O, S, $C(Z_{33})(Z_{34})$, $N(Z_{35})$, or $Si(Z_{36})(Z_{37})$;
$Z_{31}$ to $Z_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;
e1 is an integer of 1 to 5;
e2 is an integer of 1 to 7;
e3 is an integer of 1 to 3;
e4 is an integer of 1 to 4;
e5 is 1 or 2;
e6 is an integer of 1 to 6; and
* and *' are binding sites to a neighboring atom.

15. A condensed-cyclic compound represented by one of Compounds 1 to 117:

1

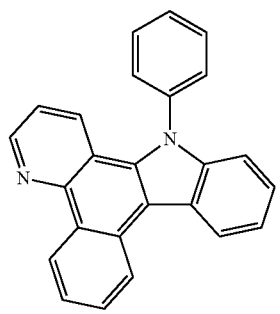

2

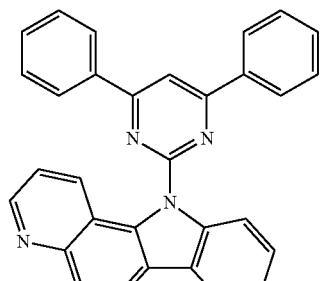

3
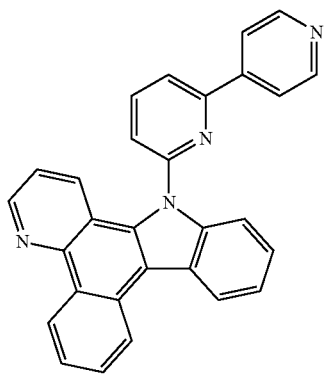
4
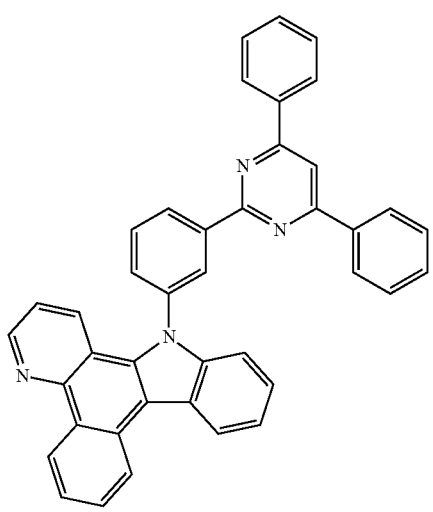
5
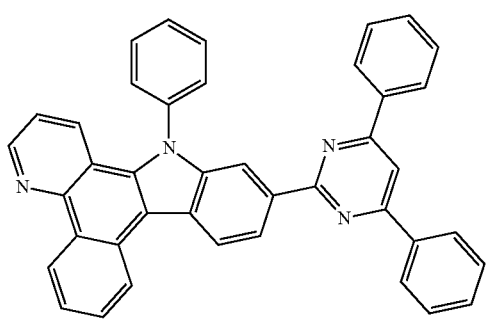
6
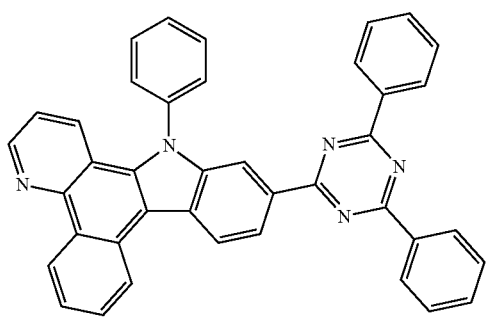
7
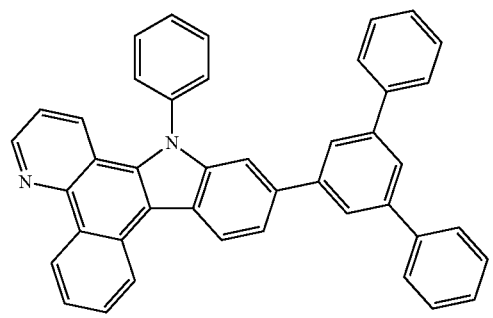
8
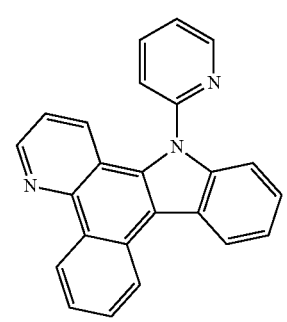
9
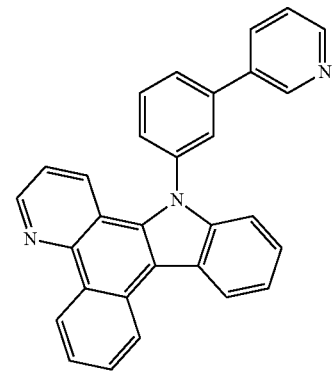
10
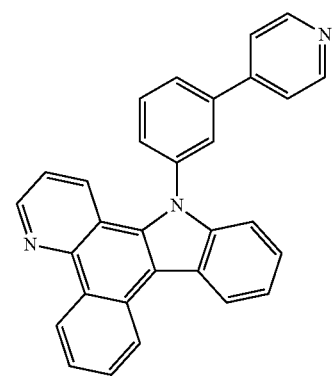

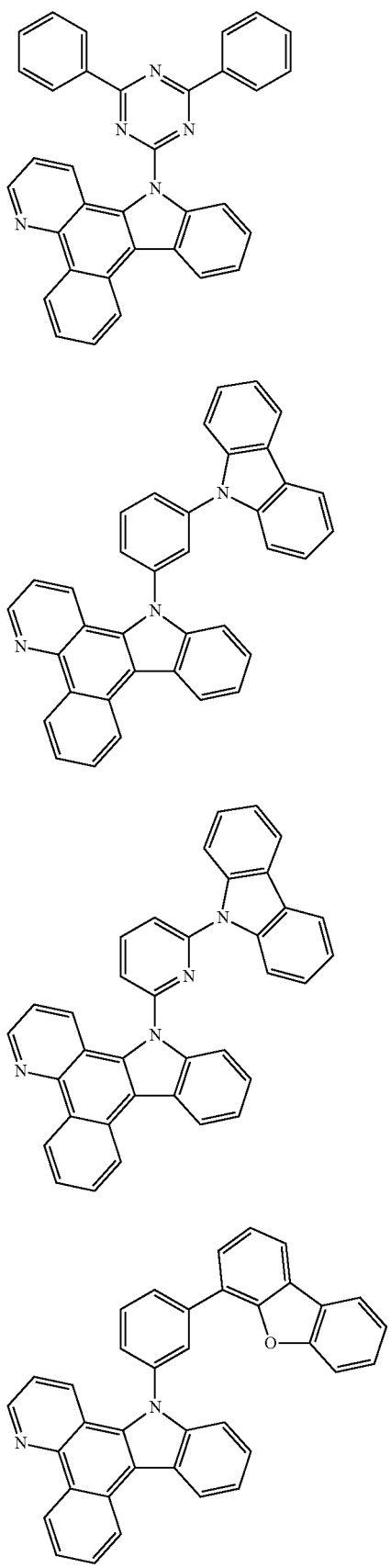
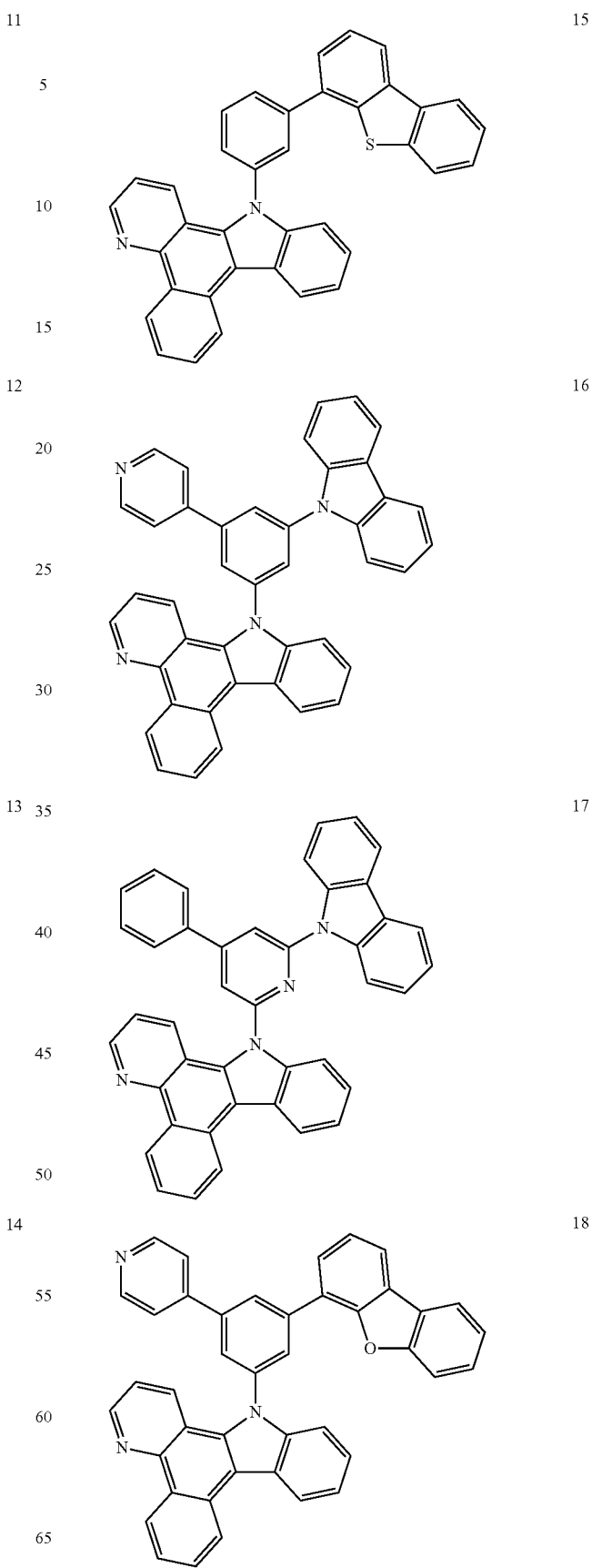

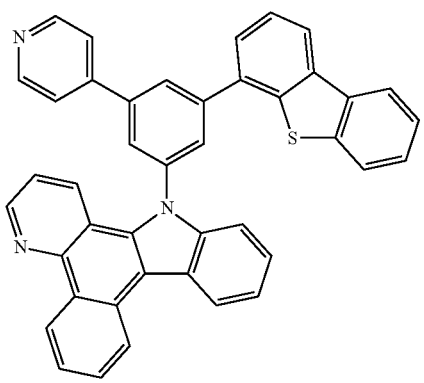
19
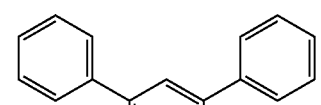
20
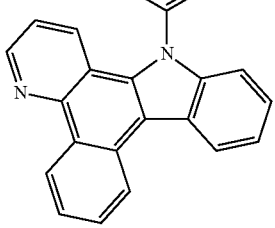
21
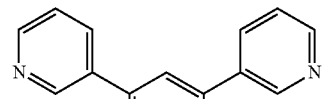
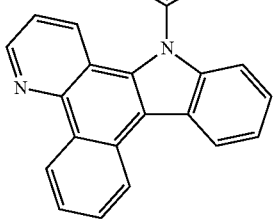
22
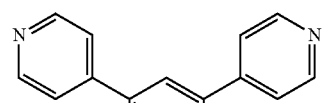
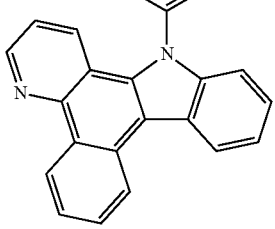
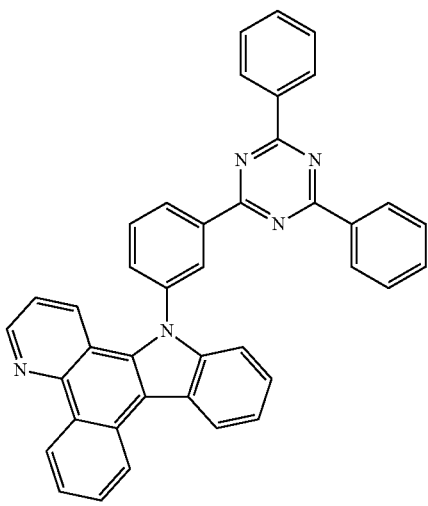
23
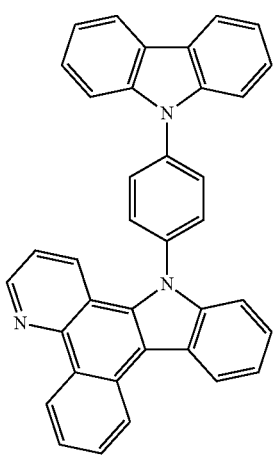
24
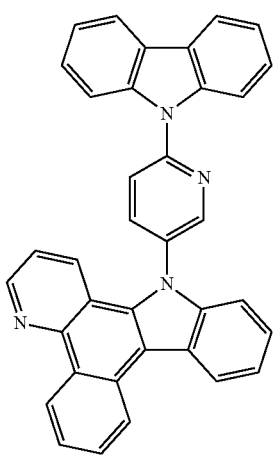
25

26
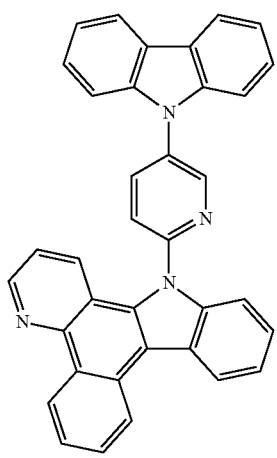
27
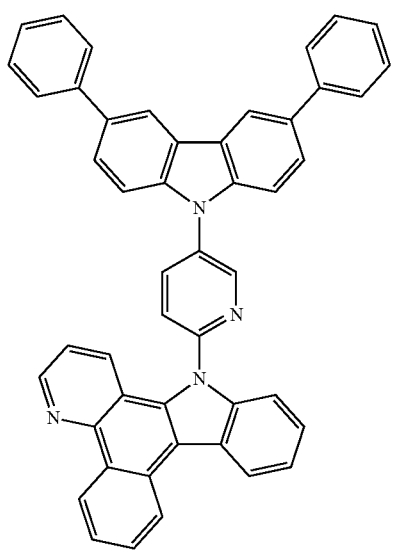
28
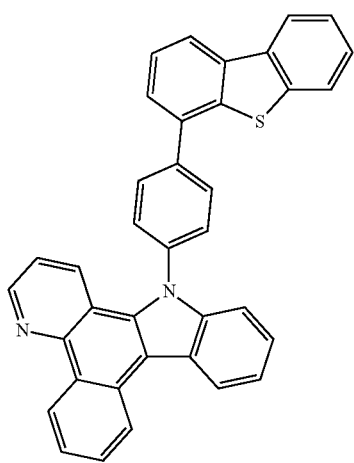
29
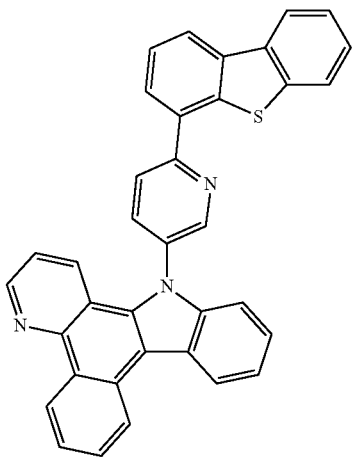
30
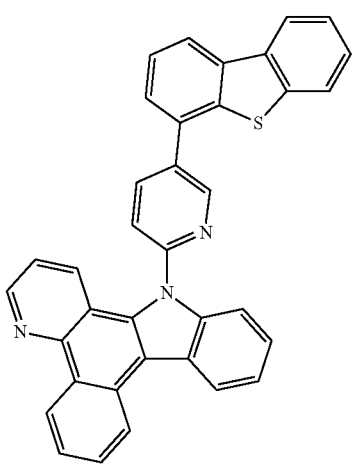
31
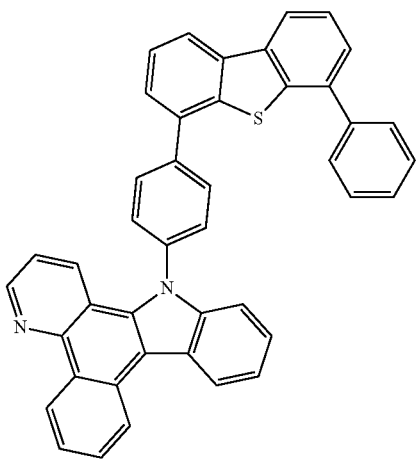

32
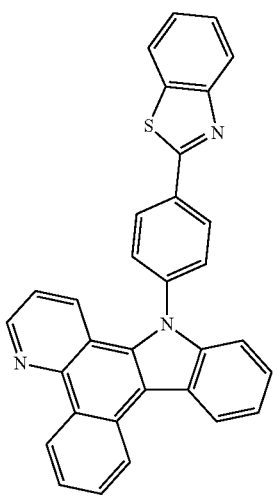
33
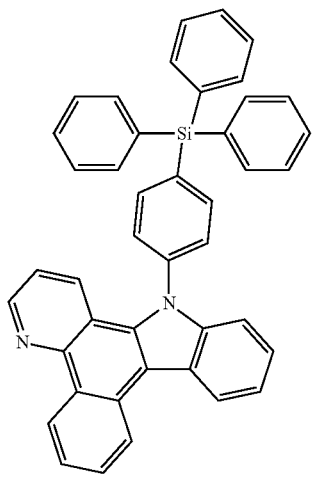
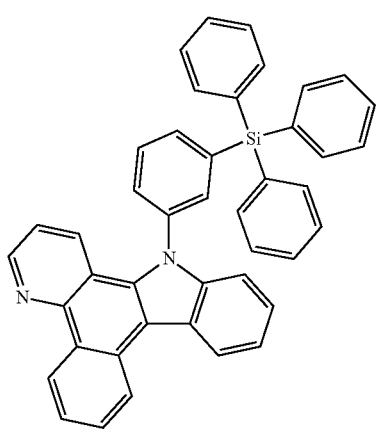
34
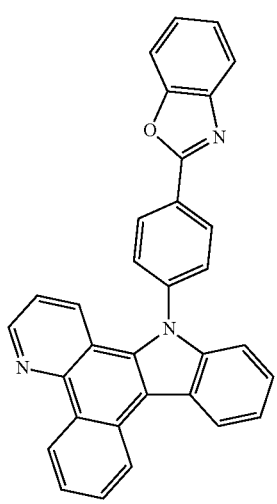
35
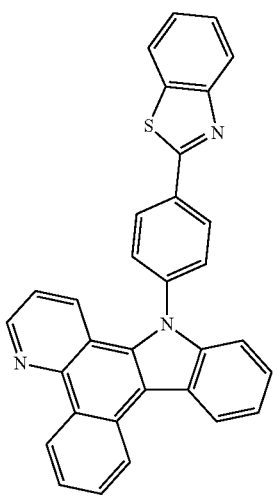
36
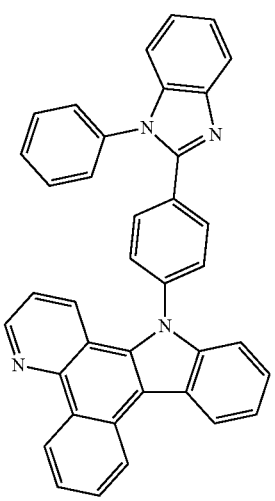
37
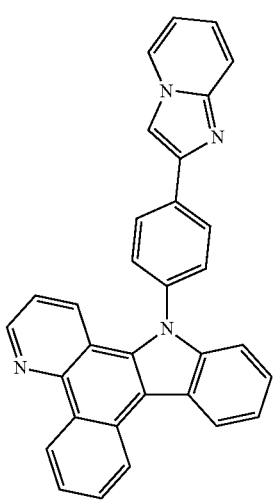

38
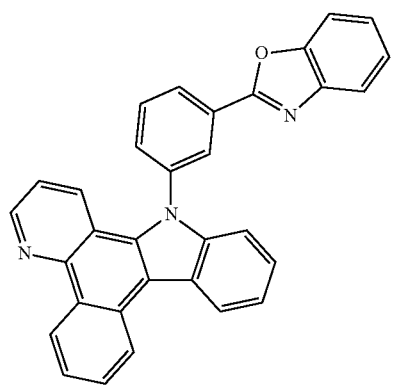
39
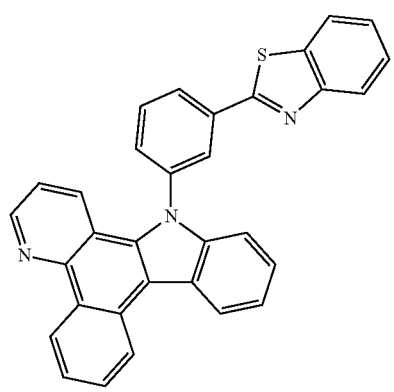
40
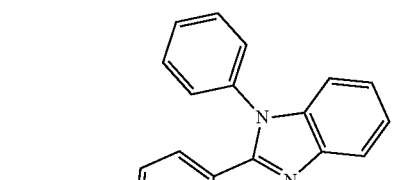
41
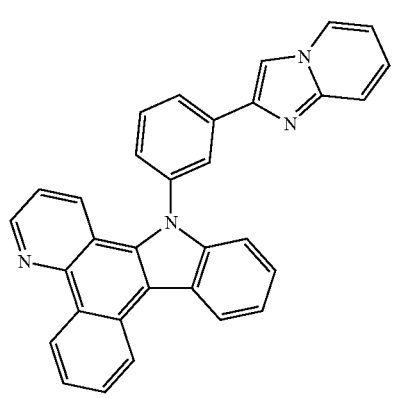
42
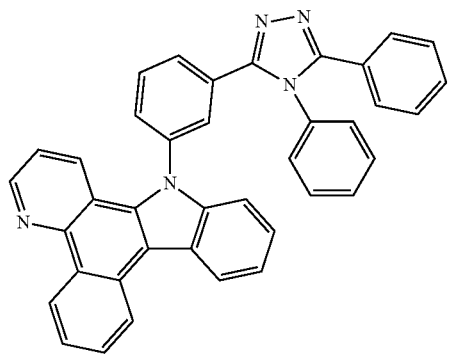
43
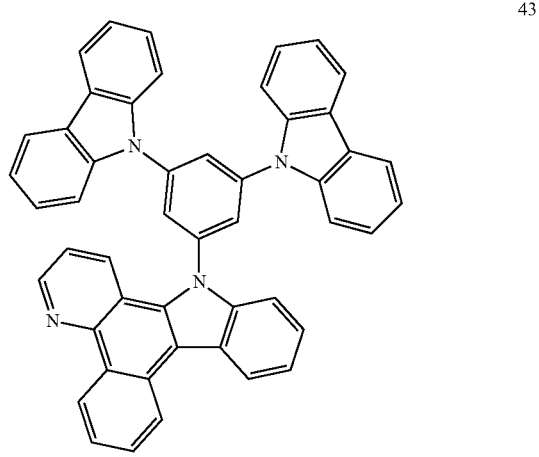
44
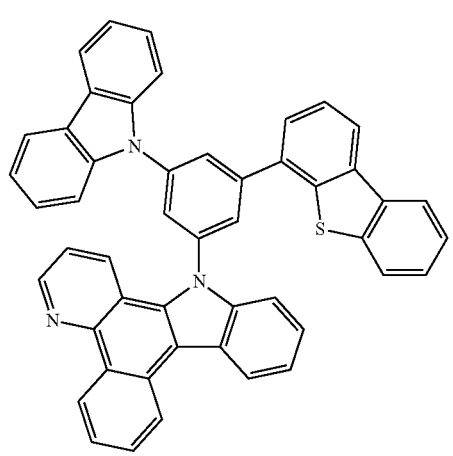

193
-continued
45
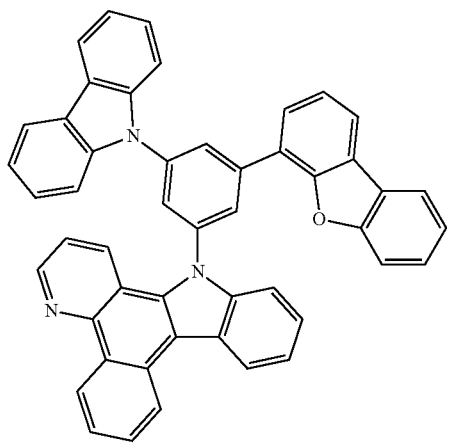
46
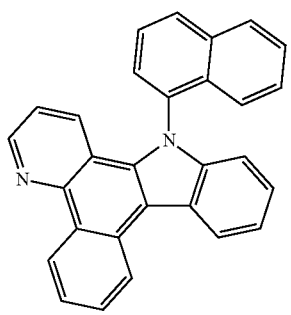
47
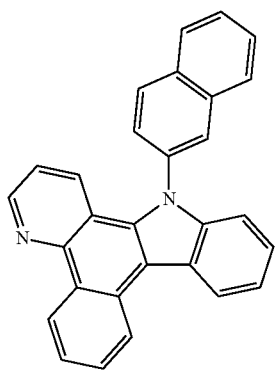
48
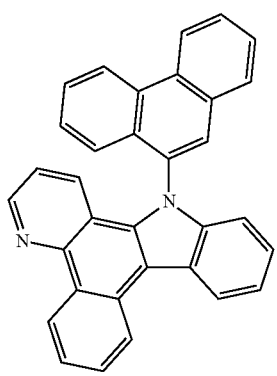
194
-continued
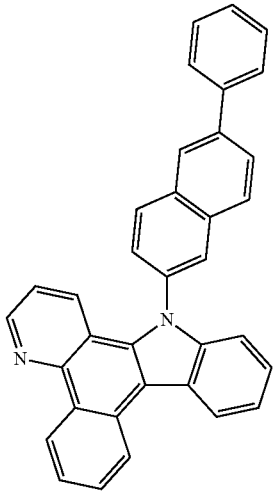
49
50
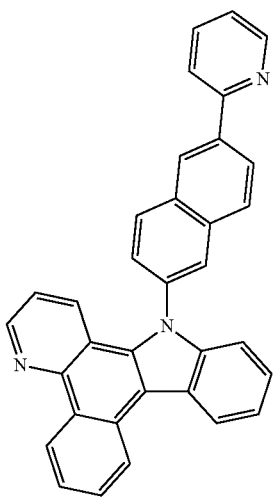
51
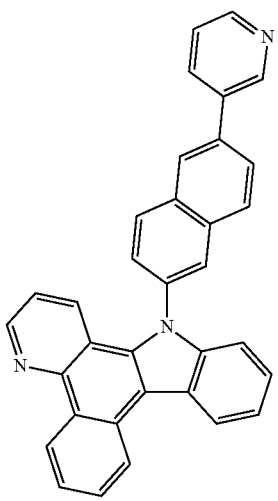

-continued
52
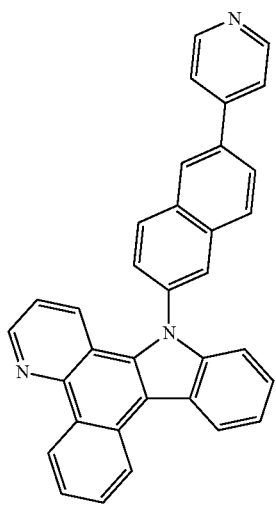
53
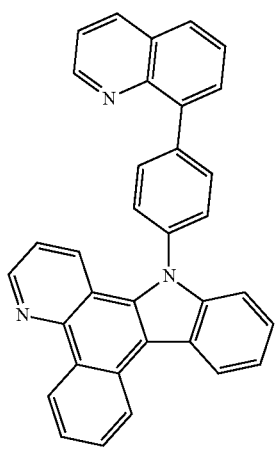
54
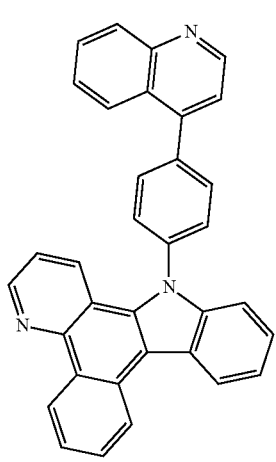
-continued
55
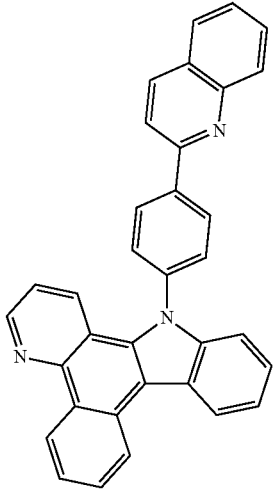
56
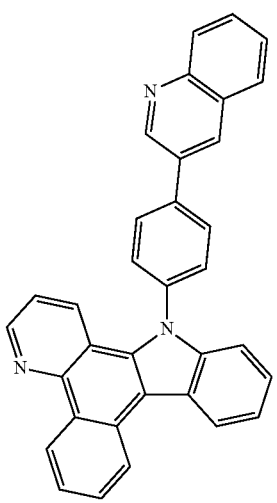
57
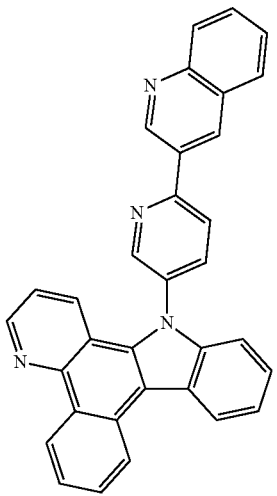

-continued
58
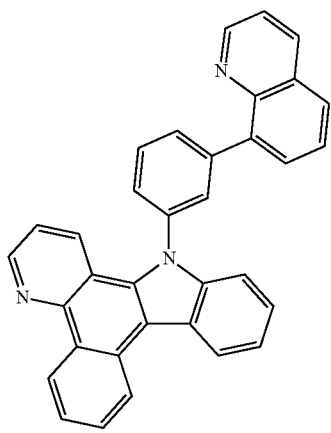
59
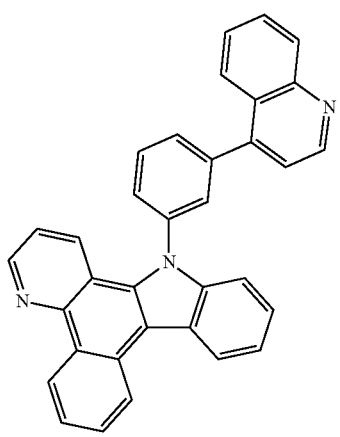
60
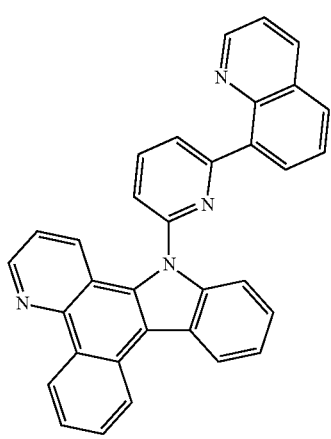
-continued
61
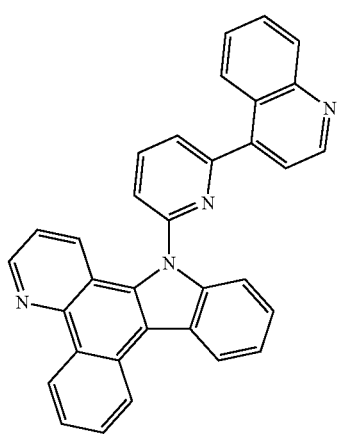
62
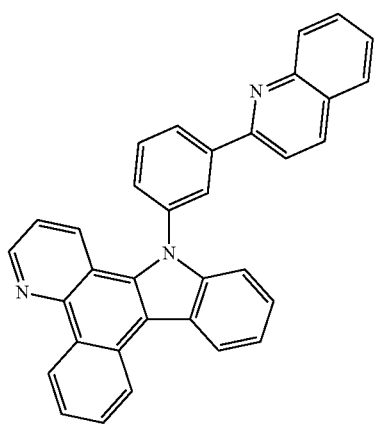
63
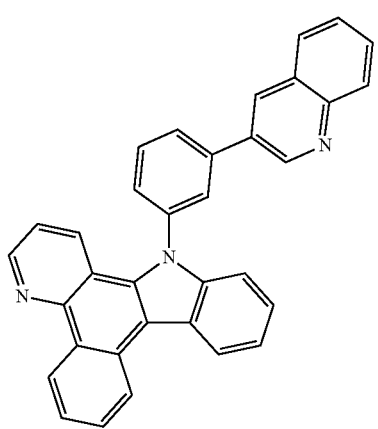

199
-continued
64
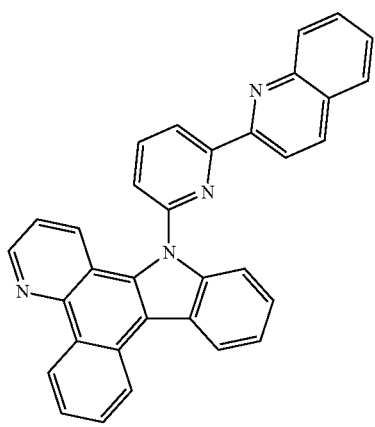
65
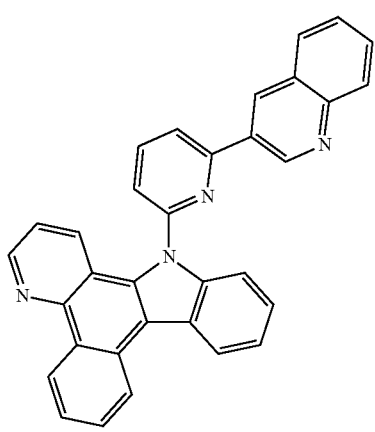
66
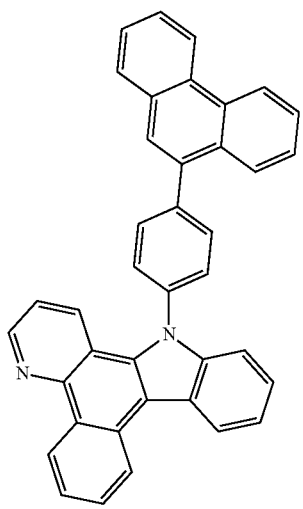
200
-continued
67
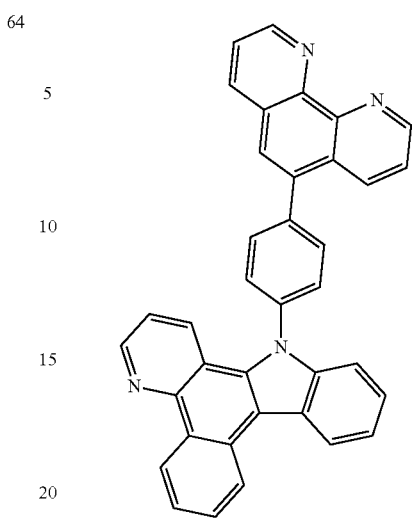
68
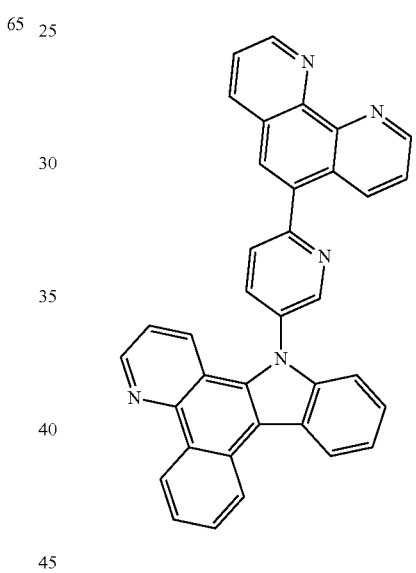
69
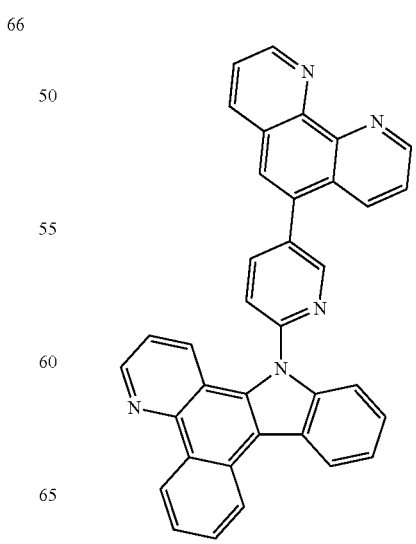

201
-continued
202
-continued
70
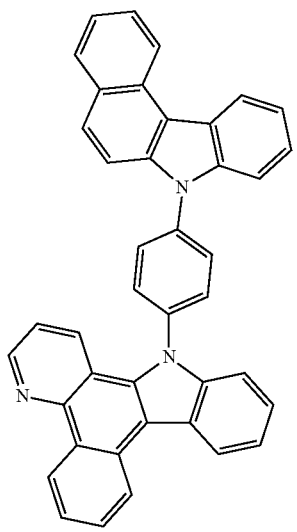
73
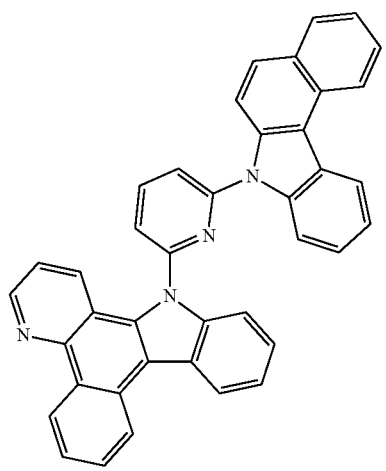
71
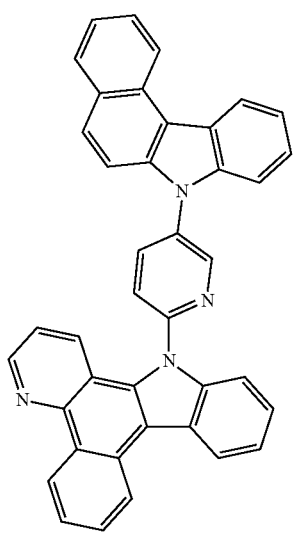
74
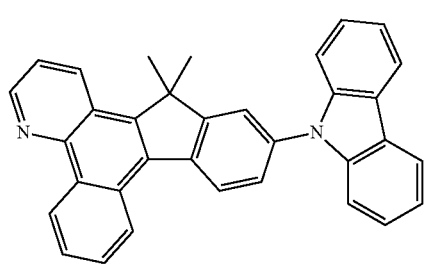
75
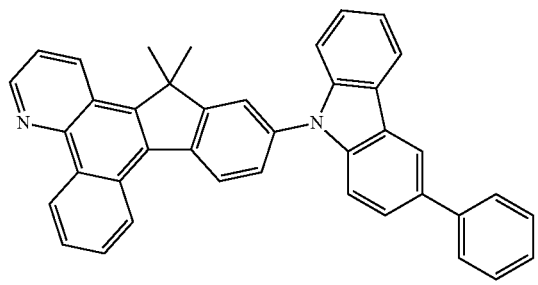
72
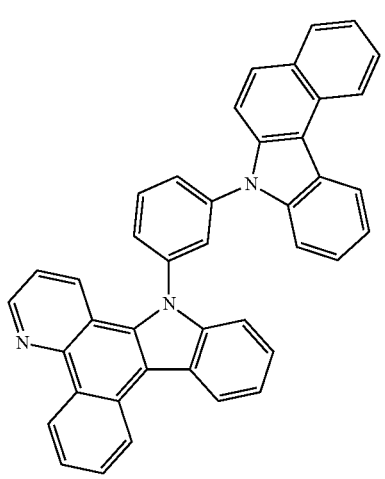
76
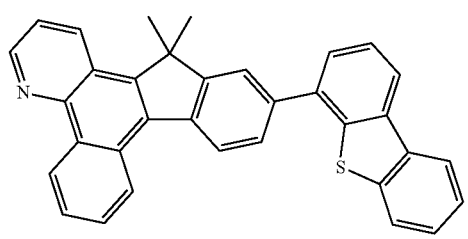
77
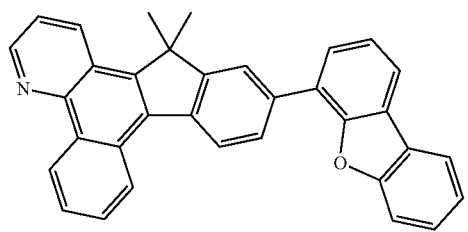

-continued

| | |
|---|---|
| 78 | 83 |
| 79 | 84 |
| 80 | 85 |
| 81 | 86 |
| 82 | 87 |

88
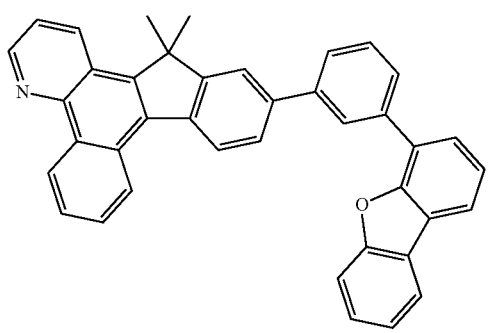
89
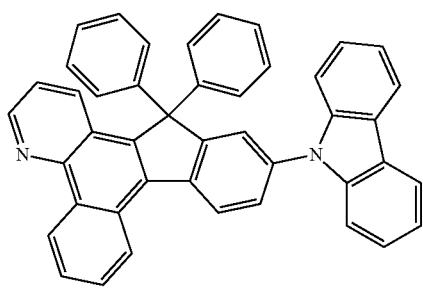
90
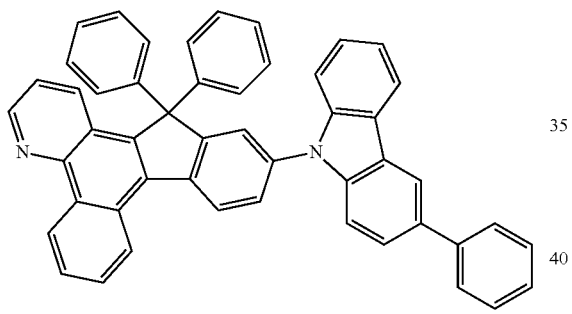
91
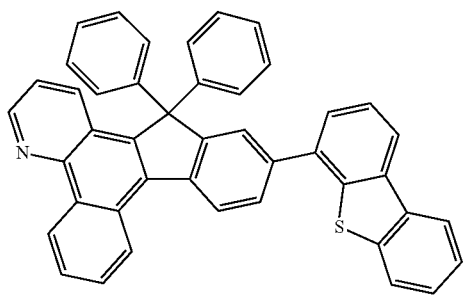
92
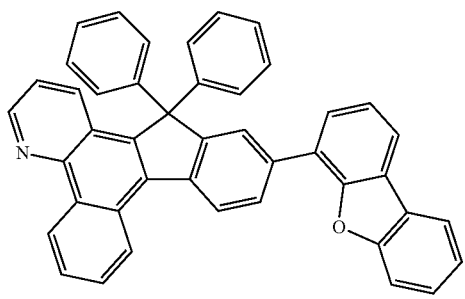
93
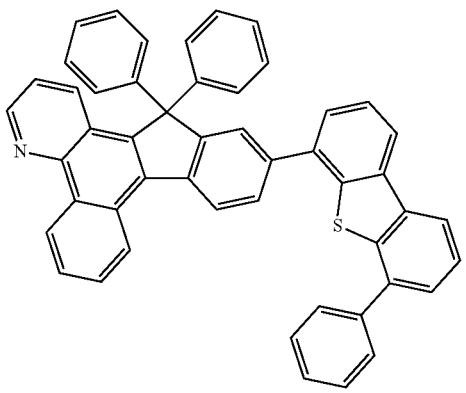
94
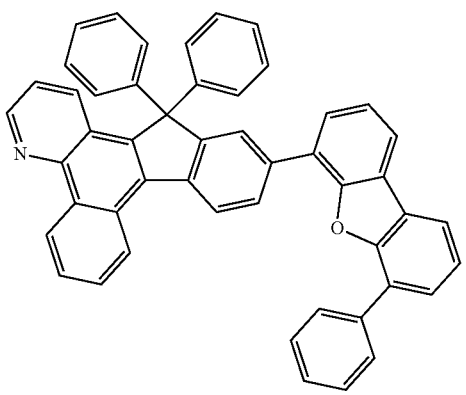
95
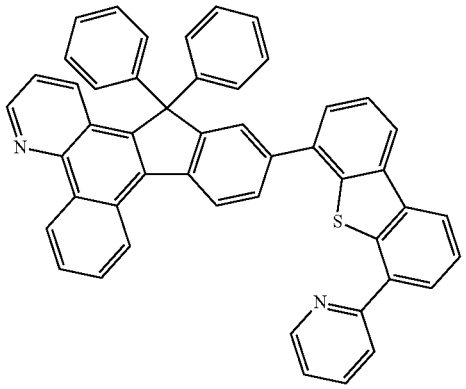
96
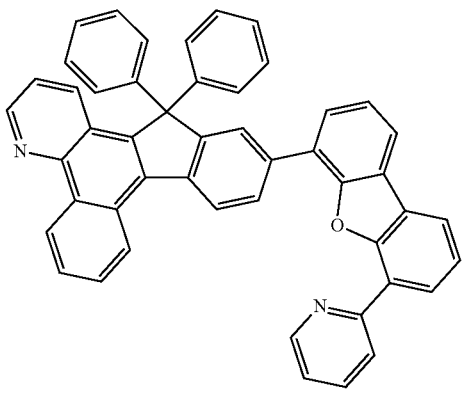

97
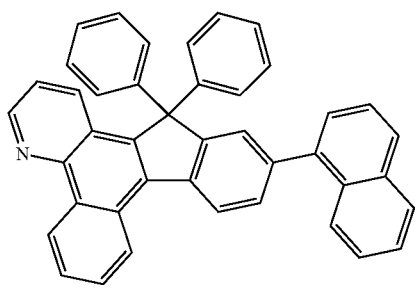
98
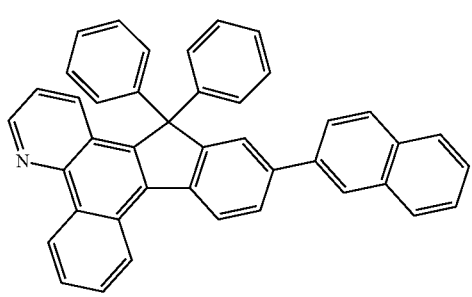
99
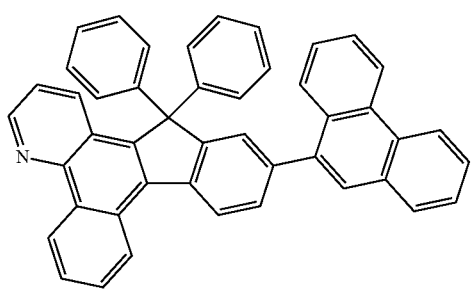
100
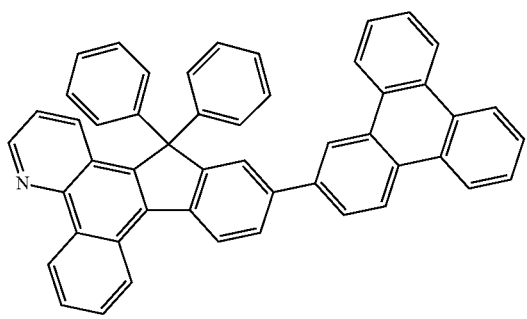
101
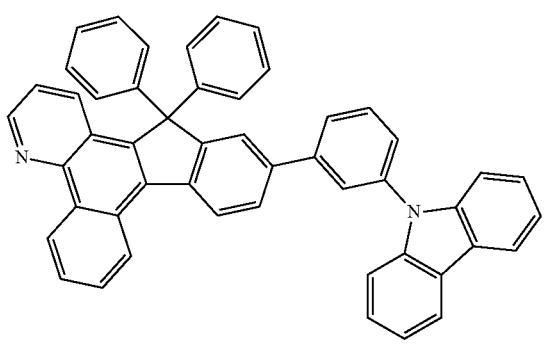
102
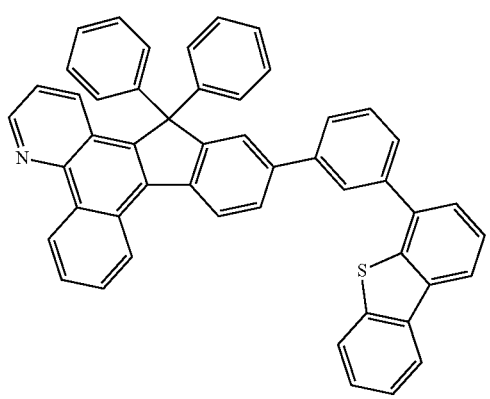
103
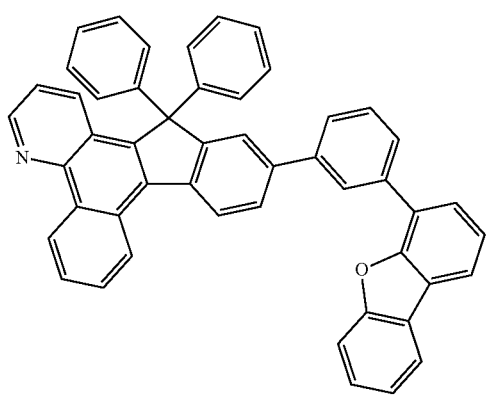
104
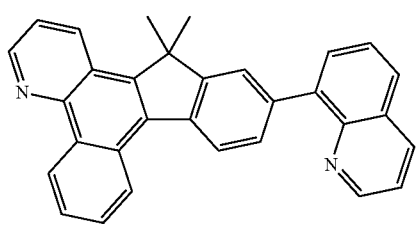
105
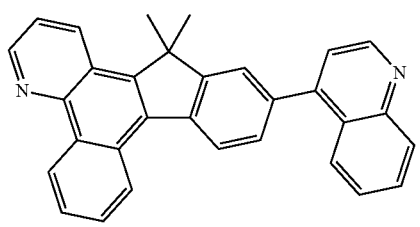
106
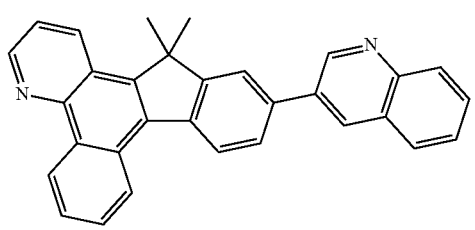

209
-continued
107
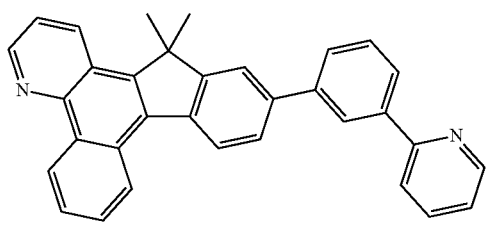
108
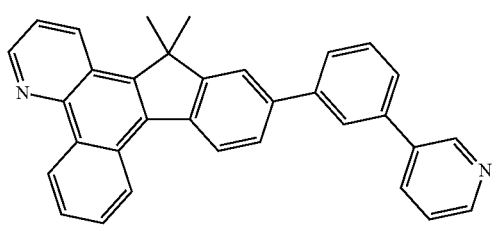
109
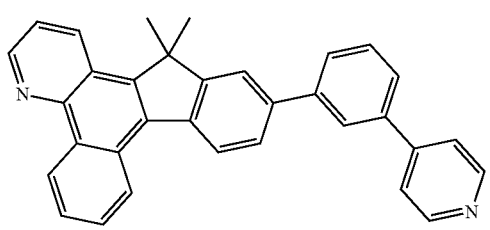
110
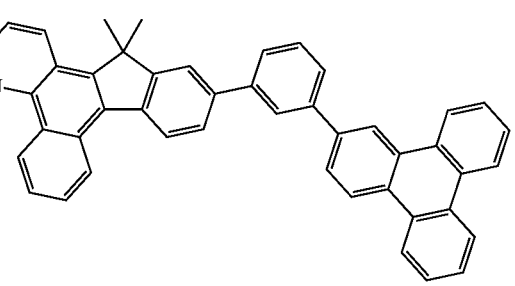
111
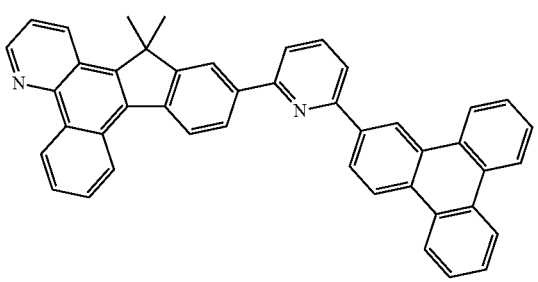
210
-continued
112
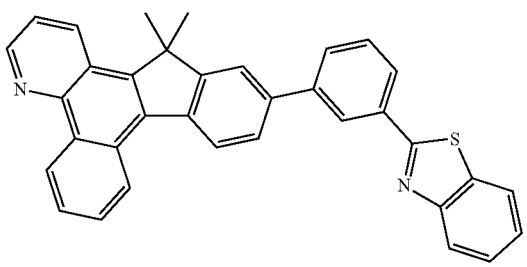
113
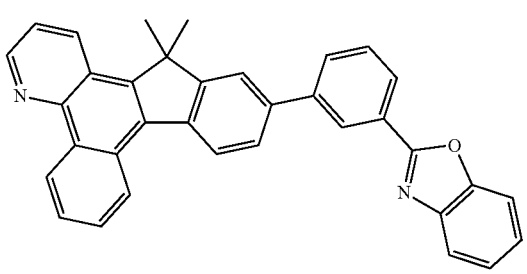
114
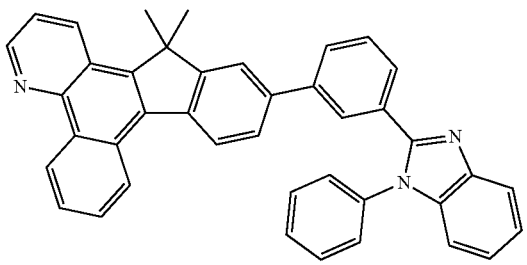
115
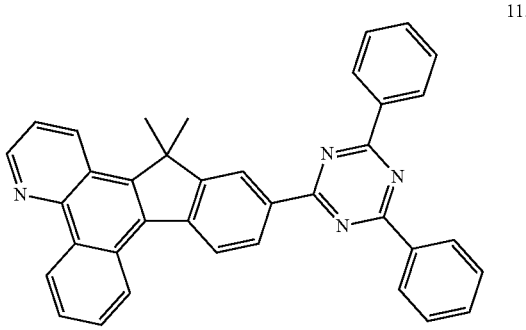
116
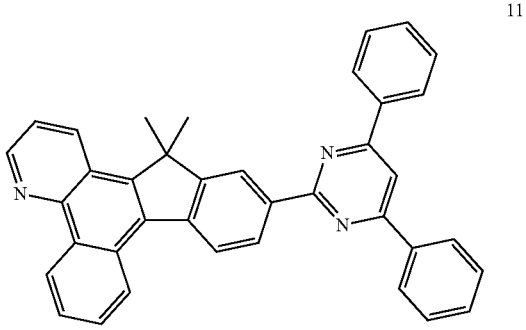

117

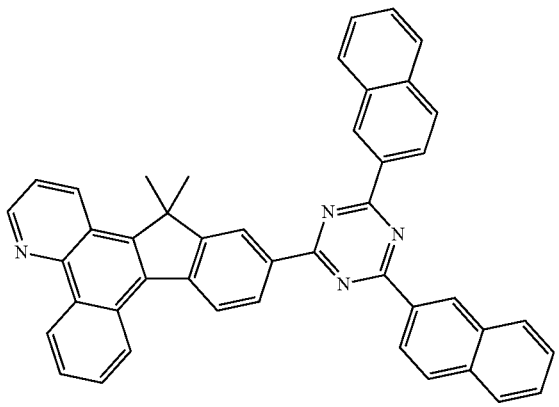

16. An organic light-emitting device comprising:
a first electrode;
a second electrode; and
an organic layer disposed between the first and second electrodes, wherein the organic layer comprises an emission layer and at least one of the condensed-cyclic compound of claim 1.

17. The organic light-emitting device of claim 16, wherein
the first electrode is an anode,
the second electrode is a cathode, and
the organic layer comprises
i) a hole transport region disposed between the first electrode and the emission layer and comprising at least one of a hole injection layer, a hole transport layer, and an electron blocking layer; and
ii) an electron transport region disposed between the emission layer and the second electrode and comprising at least one of a hole blocking layer, an electron transport layer, and an electron injection layer.

18. The organic light-emitting device of claim 16, wherein the emission layer comprises the condensed-cyclic compound.

19. The organic light-emitting device of claim 18, wherein the emission layer further comprises
a phosphorescent dopant, and
the condensed-cyclic compound,
wherein, the condensed-cyclic compound is a host.

20. A condensed-cyclic compound represented by Formula 1:

Formula 1

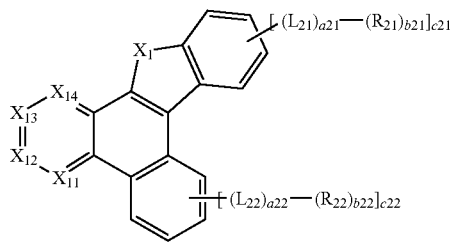

wherein, in Formula 1,
$X_1$ is $C(R_2)(R_3)$ and $R_2$ and $R_3$ do not form a ring;
$X_{11}$ is N or $C\text{-}[(L_{11})_{a11}\text{-}(R_{11})_{b11}]$,
$X_{12}$ is N or $C\text{-}[(L_{12})_{a12}\text{-}(R_{12})_{b12}]$,
$X_{13}$ is N or $C\text{-}[(L_{13})_{a13}\text{-}(R_{13})_{b13}]$, and
$X_{14}$ is N or $C\text{-}[(L_{14})_{a14}\text{-}(R_{14})_{b14}]$, provided that at least one of $X_{11}$ to $X_{14}$ is N;

$L_{11}$, $L_{12}$, $L_{13}$, $L_{14}$, $L_{21}$, and $L_{22}$ are each independently selected from a substituted or unsubstituted $C_3\text{-}C_{10}$ cycloalkylene group, a substituted or unsubstituted $C_3\text{-}C_{10}$ heterocycloalkylene group, a substituted or unsubstituted $C_3\text{-}C_{10}$ cycloalkenylene group, a substituted or unsubstituted $C_3\text{-}C_{10}$ heterocycloalkenylene group, a substituted or unsubstituted $C_6\text{-}C_{60}$ arylene group, a substituted or unsubstituted $C_2\text{-}C_{60}$ heteroarylene group, a substituted or unsubstituted divalent non-aromatic condensed polycyclic group, and a substituted or unsubstituted divalent non-aromatic hetero-condensed polycyclic group;

a11, a12, a13, a14, a21, and a22 are each independently selected from an integer of 0 to 5;

$R_2$, $R_3$, $R_{11}$, $R_{12}$, $R_{13}$, $R_{14}$, $R_{21}$, and $R_{22}$ are each independently selected from
a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1\text{-}C_{20}$ alkyl group, a $C_1\text{-}C_{20}$ alkenyl group, and a $C_1\text{-}C_{20}$ alkoxy group;

a $C_1\text{-}C_{20}$ alkyl and a $C_1\text{-}C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

Formulae 5-1 to 5-80; and
—$Si(Q_3)(Q_4)(Q_5)$; wherein $Q_3$ to $Q_5$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1\text{-}C_{20}$ alkyl group, a $C_1\text{-}C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

b11, b12, b13, b14, b21, and b22 are each independently selected from an integer of 1 to 5;

c21 and c22 are each independently 1, 2, 3, or 4, provided that
when c21 is two or more, groups *-$(L_{21})_{a21}$-$(R_{21})_{b21}$ are identical or different, and
when c22 is two or more, groups *-$(L_{22})_{a22}$-$(R_{R22})_{b22}$ are identical or different; and wherein when R₂ and R₃ are each independently selected from group represented by Formulae 5-1 to 5-80, a21 is selected from an integer of 1 to 5:
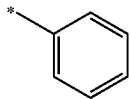
Formula 5-1
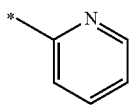
Formula 5-2
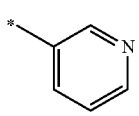
Formula 5-3
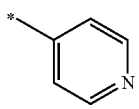
Formula 5-4
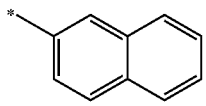
Formula 5-5
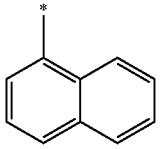
Formula 5-6
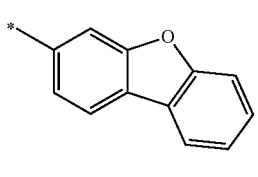
Formula 5-7
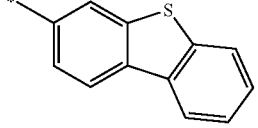
Formula 5-8
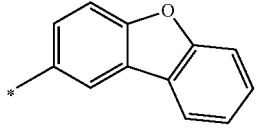
Formula 5-9
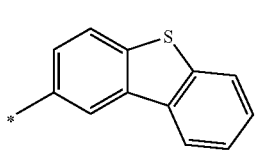
Formula 5-10
-continued
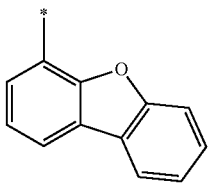
Formula 5-11
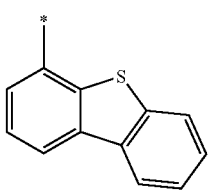
Formula 5-12
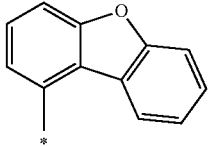
Formula 5-13
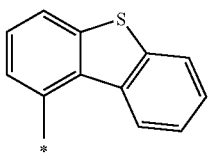
Formula 5-14
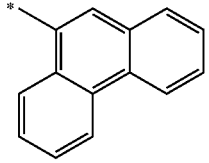
Formula 5-15
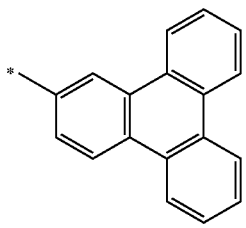
Formula 5-16
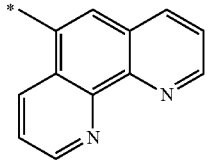
Formula 5-17
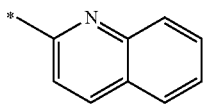
Formula 5-18
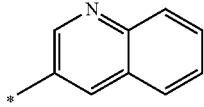
Formula 5-19

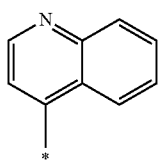
Formula 5-20
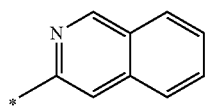
Formula 5-21
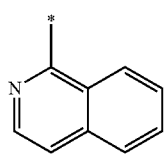
Formula 5-22
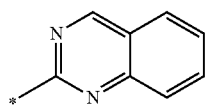
Formula 5-23
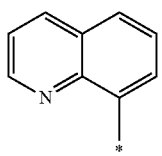
Formula 5-24
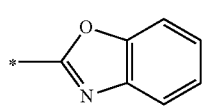
Formula 5-25
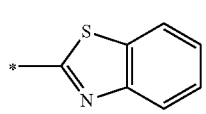
Formula 5-26
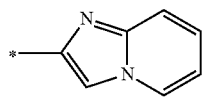
Formula 5-27
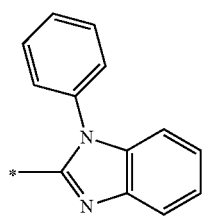
Formula 5-28
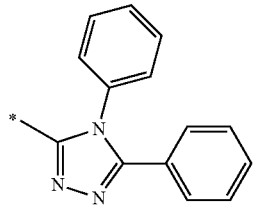
Formula 5-29
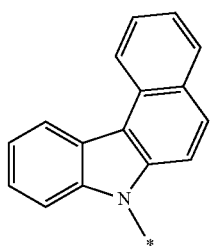
Formula 5-30
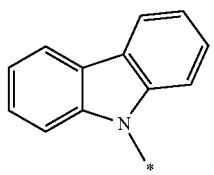
Formula 5-31
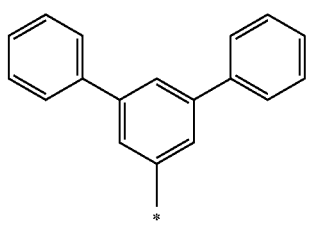
Formula 5-32
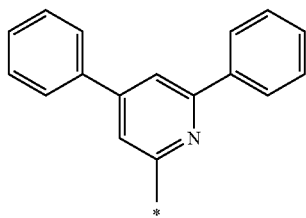
Formula 5-33
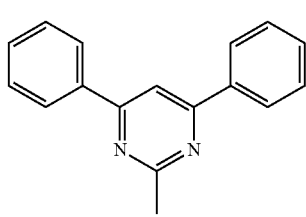
Formula 5-34
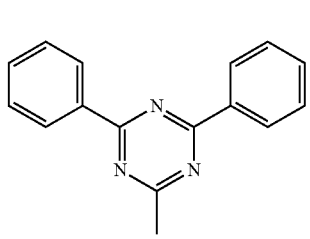
Formula 5-35
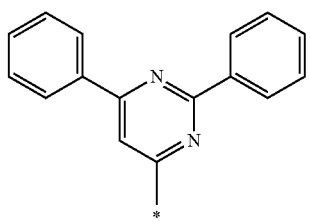
Formula 5-36

Formula 5-37

Formula 5-38

Formula 5-39

Formula 5-40

Formula 5-41

Formula 5-42

Formula 5-43

Formula 5-44

Formula 5-45

Formula 5-46

Formula 5-47

Formula 5-48

Formula 5-49
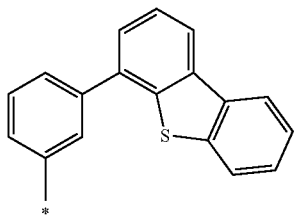
Formula 5-55
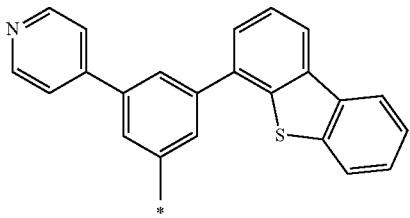
Formula 5-50
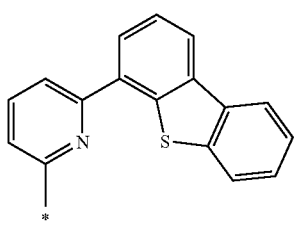
Formula 5-56
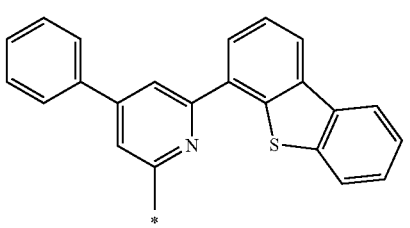
Formula 5-51
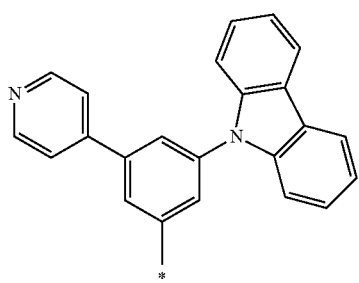
Formula 5-57
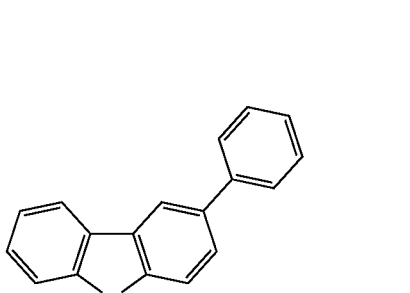
Formula 5-52
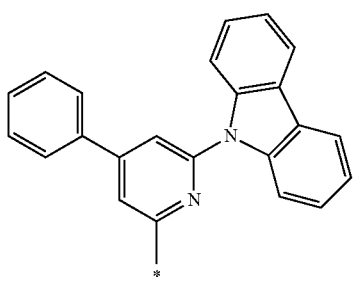
Formula 5-58
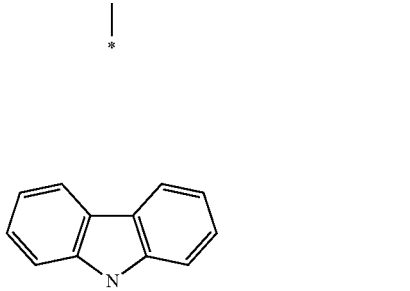
Formula 5-53
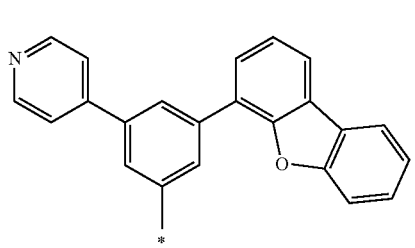
Formula 5-54
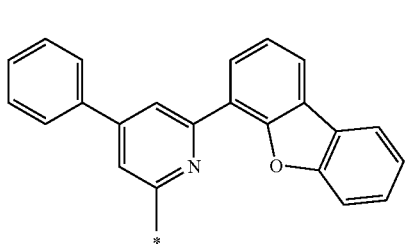
Formula 5-59
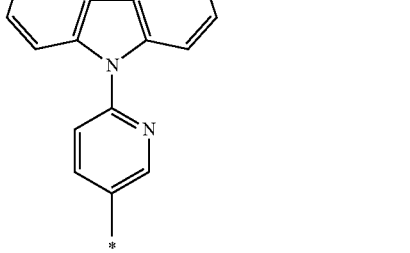

Formula 5-60
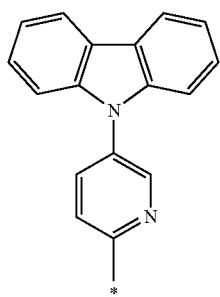
Formula 5-61
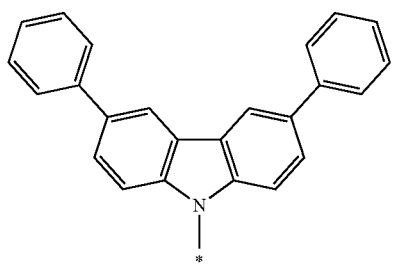
Formula 5-62
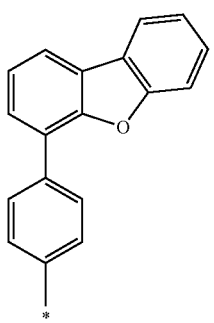
Formula 5-63
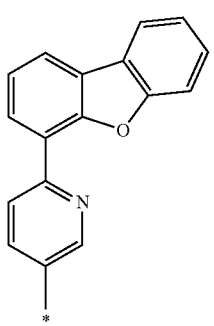
Formula 5-64
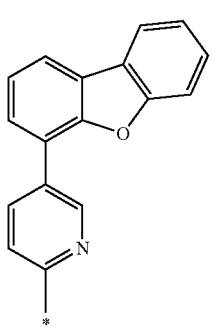
Formula 5-65
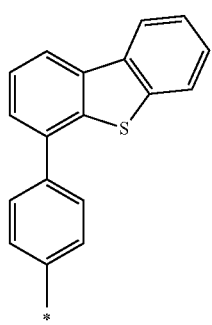
Formula 5-66
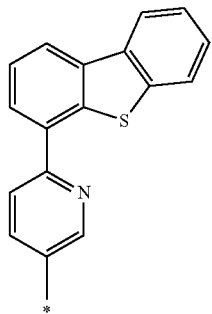
Formula 5-67
Formula 5-68
Formula 5-69

Formula 5-70
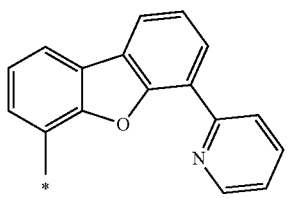
Formula 5-71
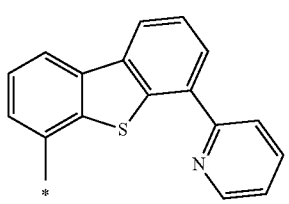
Formula 5-72
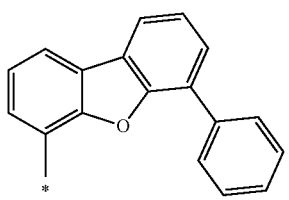
Formula 5-73
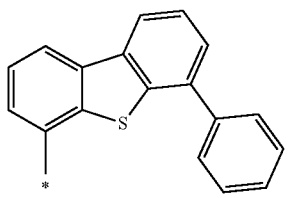
Formula 5-74
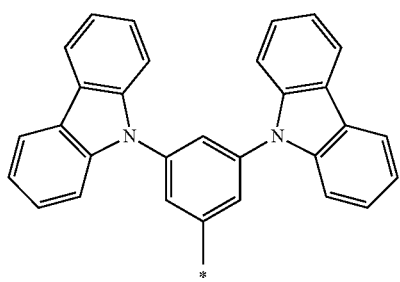
Formula 5-75
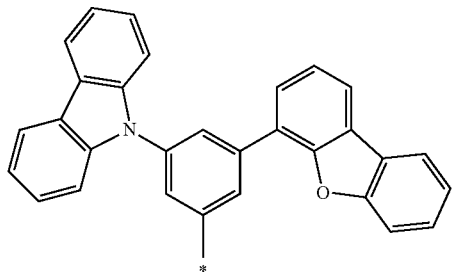
Formula 5-76
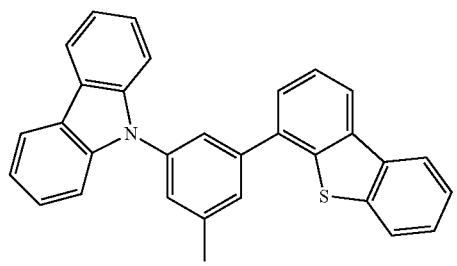
Formula 5-77
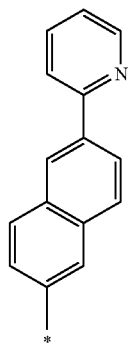
Formula 5-78
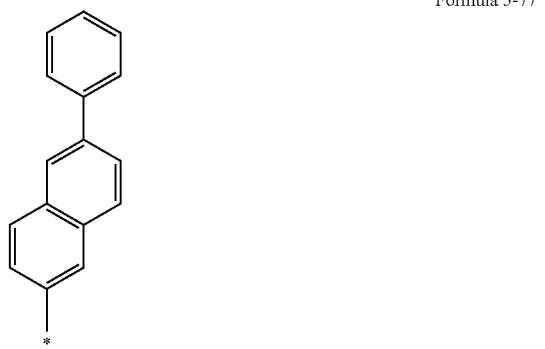
Formula 5-79
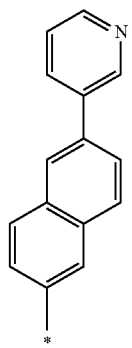

Formula 5-80
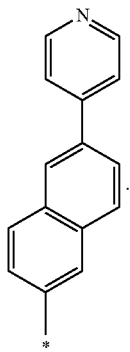
21. An organic light-emitting device comprising:
a first electrode;
a second electrode; and
an organic layer disposed between the first and second electrodes,
wherein the organic layer comprises an emission layer and at least one of the condensed-cyclic compound of claim 20.
* * * * *